(12) United States Patent
Darlak et al.

(10) Patent No.: US 9,845,287 B2
(45) Date of Patent: Dec. 19, 2017

(54) DISUBSTITUTED AMINO ACIDS AND METHODS OF PREPARATION AND USE THEREOF

(71) Applicant: Aileron Therapeutics, Inc., Cambridge, MA (US)

(72) Inventors: Krzysztof Darlak, Newton, MA (US); Noriyuki Kawahata, West Roxbury, MA (US); Sameer Ahmed Athamneh, Corvallis, OR (US)

(73) Assignee: AILERON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/278,824

(22) Filed: Sep. 28, 2016

(65) Prior Publication Data

US 2017/0066714 A1    Mar. 9, 2017

Related U.S. Application Data

(63) Continuation of application No. 14/070,306, filed on Nov. 1, 2013.

(60) Provisional application No. 61/721,457, filed on Nov. 1, 2012, provisional application No. 61/799,917, filed on Mar. 15, 2013.

(51) Int. Cl.
    C07C 271/34    (2006.01)
    C07C 269/08    (2006.01)
    C07K 1/00      (2006.01)
    C07C 271/22    (2006.01)

(52) U.S. Cl.
    CPC .......... *C07C 271/34* (2013.01); *C07C 269/08* (2013.01); *C07C 271/22* (2013.01); *C07K 1/006* (2013.01); *C07B 2200/07* (2013.01); *C07C 2603/18* (2017.05)

(58) Field of Classification Search
    None
    See application file for complete search history.

(56) References Cited

U.S. PATENT DOCUMENTS

| | | |
|---|---|---|
| 4,000,259 A | 12/1976 | Garsky |
| 4,191,754 A | 3/1980 | Nutt et al. |
| 4,270,537 A | 6/1981 | Romaine |
| 4,438,270 A | 3/1984 | Bey et al. |
| 4,518,586 A | 5/1985 | Rivier et al. |

(Continued)

FOREIGN PATENT DOCUMENTS

| | | |
|---|---|---|
| CA | 2761253 A1 | 6/2013 |
| CN | 1252808 A | 5/2000 |

(Continued)

OTHER PUBLICATIONS

Mohrig et al. Techniques in Organic Chemistry Third Edition 2010, p. 188.*

(Continued)

*Primary Examiner* — Clinton Brooks
(74) *Attorney, Agent, or Firm* — Wilson Sonsini Goodrich & Rosati

(57) ABSTRACT

Provided are crystalline α, α-disubstituted amino acids and their crystalline salts containing a terminal alkene on one of their side chains, as well as optionally crystalline halogenated and deuterated analogs of the α, α-disubstituted amino acids and their salts; methods of making these, and methods of using these.

25 Claims, 9 Drawing Sheets

(56) References Cited

U.S. PATENT DOCUMENTS

| | | |
|---|---|---|
| 4,596,556 A | 6/1986 | Morrow et al. |
| 4,683,195 A | 7/1987 | Mullis et al. |
| 4,683,202 A | 7/1987 | Mullis |
| 4,728,726 A | 3/1988 | Rivier et al. |
| 4,730,006 A | 3/1988 | Bohme et al. |
| 4,737,465 A | 4/1988 | Bond et al. |
| 4,790,824 A | 12/1988 | Morrow et al. |
| 4,880,778 A | 11/1989 | Bowers et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,036,045 A | 7/1991 | Thorner |
| 5,043,322 A | 8/1991 | Rivier et al. |
| 5,064,413 A | 11/1991 | McKinnon et al. |
| 5,094,951 A | 3/1992 | Rosenberg |
| 5,112,808 A | 5/1992 | Coy et al. |
| 5,120,859 A | 6/1992 | Webb |
| 5,141,496 A | 8/1992 | Dalto et al. |
| 5,169,932 A | 12/1992 | Hoeger et al. |
| 5,190,521 A | 3/1993 | Hubbard et al. |
| 5,245,009 A | 9/1993 | Kornreich et al. |
| 5,262,519 A | 11/1993 | Rivier et al. |
| 5,296,468 A | 3/1994 | Hoeger et al. |
| 5,310,910 A | 5/1994 | Drtina et al. |
| 5,312,335 A | 5/1994 | McKinnon et al. |
| 5,323,907 A | 6/1994 | Kalvelage |
| 5,328,483 A | 7/1994 | Jacoby |
| 5,334,144 A | 8/1994 | Alchas et al. |
| 5,339,163 A | 8/1994 | Homma et al. |
| 5,352,796 A | 10/1994 | Hoeger et al. |
| 5,364,851 A | 11/1994 | Joran |
| 5,371,070 A | 12/1994 | Koerber et al. |
| 5,383,851 A | 1/1995 | McKinnon, Jr. et al. |
| 5,384,309 A | 1/1995 | Barker et al. |
| 5,416,073 A | 5/1995 | Coy et al. |
| 5,417,662 A | 5/1995 | Hjertman et al. |
| 5,446,128 A | 8/1995 | Kahn |
| 5,453,418 A | 9/1995 | Anderson et al. |
| 5,466,220 A | 11/1995 | Brenneman |
| 5,480,381 A | 1/1996 | Weston |
| 5,503,627 A | 4/1996 | McKinnon et al. |
| 5,506,207 A | 4/1996 | Rivier et al. |
| 5,520,639 A | 5/1996 | Peterson et al. |
| 5,527,288 A | 6/1996 | Gross et al. |
| 5,552,520 A | 9/1996 | Kim et al. |
| 5,569,189 A | 10/1996 | Parsons |
| 5,580,957 A | 12/1996 | Hoeger et al. |
| 5,599,302 A | 2/1997 | Lilley et al. |
| 5,620,708 A | 4/1997 | Amkraut et al. |
| 5,622,852 A | 4/1997 | Korsmeyer |
| 5,629,020 A | 5/1997 | Leone-Bay et al. |
| 5,635,371 A | 6/1997 | Stout et al. |
| 5,643,957 A | 7/1997 | Leone-Bay et al. |
| 5,649,912 A | 7/1997 | Peterson |
| 5,650,133 A | 7/1997 | Carvalho et al. |
| 5,650,386 A | 7/1997 | Leone-Bay et al. |
| 5,656,721 A | 8/1997 | Albert et al. |
| 5,663,316 A | 9/1997 | Xudong |
| 5,672,584 A | 9/1997 | Borchardt et al. |
| 5,681,928 A | 10/1997 | Rivier et al. |
| 5,700,775 A | 12/1997 | Gutniak et al. |
| 5,702,908 A | 12/1997 | Picksley et al. |
| 5,704,911 A | 1/1998 | Parsons |
| 5,708,136 A | 1/1998 | Burrell et al. |
| 5,710,245 A | 1/1998 | Kahn |
| 5,710,249 A | 1/1998 | Hoeger et al. |
| 5,731,408 A | 3/1998 | Hadley et al. |
| 5,744,450 A | 4/1998 | Hoeger et al. |
| 5,750,499 A | 5/1998 | Hoeger et al. |
| 5,750,767 A | 5/1998 | Carpino et al. |
| 5,756,669 A | 5/1998 | Bischoff et al. |
| 5,770,377 A | 6/1998 | Picksley et al. |
| 5,792,747 A | 8/1998 | Schally et al. |
| 5,807,983 A | 9/1998 | Jiang et al. |
| 5,811,515 A | 9/1998 | Grubbs et al. |
| 5,817,752 A | 10/1998 | Yu |
| 5,817,789 A | 10/1998 | Heartlein et al. |
| 5,824,483 A | 10/1998 | Houston, Jr. et al. |
| 5,834,209 A | 11/1998 | Korsmeyer |
| 5,837,845 A | 11/1998 | Hosokawa et al. |
| 5,840,833 A | 11/1998 | Kahn |
| 5,846,936 A | 12/1998 | Felix et al. |
| 5,847,066 A | 12/1998 | Coy et al. |
| 5,854,216 A | 12/1998 | Gaudreau |
| 5,856,445 A | 1/1999 | Korsmeyer |
| 5,859,184 A | 1/1999 | Kahn et al. |
| 5,861,379 A | 1/1999 | Ibea et al. |
| 5,874,529 A | 2/1999 | Gilon et al. |
| 5,893,397 A | 4/1999 | Peterson et al. |
| 5,922,863 A | 7/1999 | Grubbs et al. |
| 5,939,386 A | 8/1999 | Ibea et al. |
| 5,939,387 A | 8/1999 | Broderick et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,020,311 A | 2/2000 | Brazeau et al. |
| 6,030,997 A | 2/2000 | Eilat et al. |
| 6,031,073 A | 2/2000 | Yu |
| 6,043,339 A | 3/2000 | Lin et al. |
| 6,046,289 A | 4/2000 | Komazawa et al. |
| 6,051,513 A | 4/2000 | Kumazawa et al. |
| 6,051,554 A | 4/2000 | Hornik et al. |
| 6,054,556 A | 4/2000 | Huby et al. |
| 6,060,513 A | 5/2000 | Leone-Bay et al. |
| 6,066,470 A | 5/2000 | Nishimura et al. |
| 6,071,510 A | 6/2000 | Leone-Bay et al. |
| 6,071,538 A | 6/2000 | Milstein et al. |
| 6,071,926 A | 6/2000 | Van et al. |
| 6,090,958 A | 7/2000 | Leone-Bay et al. |
| 6,100,298 A | 8/2000 | Leone-Bay et al. |
| 6,118,010 A | 9/2000 | Ueda et al. |
| 6,123,964 A | 9/2000 | Asgharnejad et al. |
| 6,127,341 A | 10/2000 | Hansen et al. |
| 6,127,354 A | 10/2000 | Peschke et al. |
| 6,127,391 A | 10/2000 | Hansen et al. |
| 6,153,391 A | 11/2000 | Picksley et al. |
| 6,169,073 B1 | 1/2001 | Halazonetis et al. |
| 6,177,076 B1 | 1/2001 | Lattime et al. |
| 6,177,542 B1 | 1/2001 | Ruoslahti et al. |
| 6,184,344 B1 | 2/2001 | Kent et al. |
| 6,190,699 B1 | 2/2001 | Luzzi et al. |
| 6,194,384 B1 | 2/2001 | Brazeau et al. |
| 6,194,402 B1 | 2/2001 | Bach et al. |
| 6,204,361 B1 | 3/2001 | Carpino et al. |
| 6,245,359 B1 | 6/2001 | Milstein et al. |
| 6,245,886 B1 | 6/2001 | Halazonetis et al. |
| 6,248,358 B1 | 6/2001 | Bologna et al. |
| 6,271,198 B1 | 8/2001 | Braisted et al. |
| 6,274,584 B1 | 8/2001 | Peschke et al. |
| 6,287,787 B1 | 9/2001 | Houghten et al. |
| 6,307,017 B1 | 10/2001 | Coy et al. |
| 6,309,859 B1 | 10/2001 | Nishimura et al. |
| 6,313,088 B1 | 11/2001 | Leone-Bay et al. |
| 6,313,133 B1 | 11/2001 | Van et al. |
| 6,326,354 B1 | 12/2001 | Gross et al. |
| 6,331,318 B1 | 12/2001 | Milstein |
| 6,344,213 B1 | 2/2002 | Leone-Bay et al. |
| 6,346,264 B1 | 2/2002 | White |
| 6,348,558 B1 | 2/2002 | Harris et al. |
| 6,368,617 B1 | 4/2002 | Hastings et al. |
| 6,420,118 B1 | 7/2002 | Halazonetis et al. |
| 6,420,136 B1 | 7/2002 | Riabowol et al. |
| 6,444,425 B1 | 9/2002 | Reed et al. |
| 6,458,764 B1 | 10/2002 | Gravel et al. |
| 6,461,634 B1 | 10/2002 | Marshall |
| 6,495,589 B2 | 12/2002 | Hay et al. |
| 6,495,674 B1 | 12/2002 | Lemke et al. |
| 6,514,685 B1 | 2/2003 | Moro |
| 6,548,501 B2 | 4/2003 | Hakkinen |
| 6,555,156 B1 | 4/2003 | Loughman |
| 6,555,570 B2 | 4/2003 | Hansen et al. |
| 6,569,993 B1 | 5/2003 | Sledeski et al. |

(56) References Cited

U.S. PATENT DOCUMENTS

| | | |
|---|---|---|
| 6,572,856 B1 | 6/2003 | Taylor et al. |
| 6,579,967 B1 | 6/2003 | Rivier et al. |
| 6,610,657 B1 | 8/2003 | Goueli |
| 6,613,874 B1 | 9/2003 | Mazur et al. |
| 6,617,360 B1 | 9/2003 | Bailey et al. |
| 6,620,808 B2 | 9/2003 | Van et al. |
| 6,635,740 B1 | 10/2003 | Enright et al. |
| 6,641,840 B2 | 11/2003 | Am Ende et al. |
| 6,686,148 B1 | 2/2004 | Shen et al. |
| 6,696,063 B1 | 2/2004 | Torres |
| 6,696,418 B1 | 2/2004 | Hay et al. |
| 6,703,382 B2 | 3/2004 | Wang et al. |
| 6,713,280 B1 | 3/2004 | Huang et al. |
| 6,720,330 B2 | 4/2004 | Hay et al. |
| 6,747,125 B1 | 6/2004 | Hoeger et al. |
| 6,784,157 B2 | 8/2004 | Halazonetis et al. |
| 6,849,428 B1 | 2/2005 | Evans et al. |
| 6,852,722 B2 | 2/2005 | Hakkinen |
| 6,875,594 B2 | 4/2005 | Muir et al. |
| 6,897,286 B2 | 5/2005 | Jaspers et al. |
| 6,939,880 B2 | 9/2005 | Hansen et al. |
| 7,019,109 B2 | 3/2006 | Rivier et al. |
| 7,034,050 B2 | 4/2006 | Deghenghi |
| 7,064,193 B1 | 6/2006 | Cory et al. |
| 7,083,983 B2 | 8/2006 | Lane et al. |
| 7,084,244 B2 | 8/2006 | Gilon et al. |
| 7,115,372 B2 | 10/2006 | Shen et al. |
| 7,144,577 B2 | 12/2006 | Torres |
| 7,166,461 B2 | 1/2007 | Schwartz et al. |
| 7,183,059 B2 | 2/2007 | Verdine et al. |
| 7,189,801 B2 | 3/2007 | Halazonetis et al. |
| 7,192,713 B1 | 3/2007 | Verdine et al. |
| 7,202,332 B2 | 4/2007 | Arora et al. |
| 7,238,775 B2 | 7/2007 | Rivier et al. |
| 7,247,700 B2 | 7/2007 | Korsmeyer et al. |
| 7,268,113 B2 | 9/2007 | Bridon et al. |
| 7,312,304 B2 | 12/2007 | Coy et al. |
| 7,316,997 B2 | 1/2008 | Abribat et al. |
| 7,414,107 B2 | 8/2008 | Larsen et al. |
| 7,425,542 B2 | 9/2008 | Maggio |
| 7,445,919 B2 | 11/2008 | Jaspers et al. |
| 7,476,653 B2 | 1/2009 | Hoveyda et al. |
| 7,485,620 B2 | 2/2009 | Ghigo et al. |
| 7,491,695 B2 | 2/2009 | Fraser et al. |
| 7,521,420 B2 | 4/2009 | Fraser et al. |
| 7,538,190 B2 | 5/2009 | Robinson et al. |
| 7,566,777 B2 | 7/2009 | Enright et al. |
| 7,638,138 B2 | 12/2009 | Oki et al. |
| 7,655,447 B2 | 2/2010 | Jaspers et al. |
| 7,666,983 B2 | 2/2010 | Halazonetis et al. |
| 7,705,118 B2 | 4/2010 | Arora et al. |
| 7,723,469 B2 | 5/2010 | Walensky et al. |
| 7,737,174 B2 | 6/2010 | Wang et al. |
| 7,745,573 B2 | 6/2010 | Robinson et al. |
| 7,759,383 B2 | 7/2010 | Wang et al. |
| 7,786,072 B2 | 8/2010 | Verdine et al. |
| 7,829,724 B2 | 11/2010 | Perrissoud et al. |
| RE42,013 E | 12/2010 | Hoveyda |
| 7,884,073 B2 | 2/2011 | Guyon et al. |
| 7,884,107 B2 | 2/2011 | Ma et al. |
| 7,888,056 B2 | 2/2011 | Sheppard et al. |
| 7,893,025 B2 | 2/2011 | Lussier et al. |
| 7,893,278 B2 | 2/2011 | Haley et al. |
| 7,927,813 B2 | 4/2011 | Geneste et al. |
| 7,932,397 B2 | 4/2011 | Hock et al. |
| 7,960,342 B2 | 6/2011 | Rivier et al. |
| 7,960,506 B2 | 6/2011 | Nash |
| 7,964,724 B2 | 6/2011 | Fotouhi et al. |
| 7,981,998 B2 | 7/2011 | Nash |
| 7,981,999 B2 | 7/2011 | Nash |
| RE42,624 E | 8/2011 | Fraser |
| 7,994,329 B2 | 8/2011 | Andersen et al. |
| 7,998,927 B2 | 8/2011 | Maggio |
| 7,998,930 B2 | 8/2011 | Guyon et al. |
| 8,017,607 B2 | 9/2011 | Bartkovitz et al. |
| 8,039,456 B2 | 10/2011 | Polvino et al. |
| 8,039,457 B2 | 10/2011 | Polvino |
| 8,058,269 B2 | 11/2011 | Chen et al. |
| 8,071,541 B2 | 12/2011 | Arora et al. |
| 8,076,290 B2 | 12/2011 | Maggio |
| 8,076,482 B2 | 12/2011 | Chen et al. |
| 8,084,022 B2 | 12/2011 | Maggio |
| 8,088,733 B2 | 1/2012 | Fraser et al. |
| 8,088,815 B2 | 1/2012 | Bartkovitz et al. |
| 8,088,931 B2 | 1/2012 | Wang et al. |
| 8,124,356 B2 | 2/2012 | Sheppard et al. |
| 8,124,726 B2 | 2/2012 | Robinson et al. |
| 8,129,561 B2 | 3/2012 | Marsault et al. |
| 8,133,863 B2 | 3/2012 | Maggio |
| 8,173,594 B2 | 5/2012 | Maggio |
| 8,192,719 B2 | 6/2012 | Larsen |
| 8,198,405 B2 | 6/2012 | Walensky et al. |
| 8,217,051 B2 | 7/2012 | Zhang et al. |
| 8,222,209 B2 | 7/2012 | Guyon et al. |
| 8,226,949 B2 | 7/2012 | Maggio |
| 8,314,066 B2 | 11/2012 | Abribat et al. |
| 8,324,428 B2 | 12/2012 | Verdine et al. |
| 8,334,256 B2 | 12/2012 | Marsault et al. |
| 8,343,760 B2 | 1/2013 | Lu et al. |
| 8,349,887 B2 | 1/2013 | Fraser et al. |
| 8,389,484 B2 | 3/2013 | Shen et al. |
| 8,399,405 B2 | 3/2013 | Nash et al. |
| 8,435,945 B2 | 5/2013 | Abribat et al. |
| 8,450,268 B2 | 5/2013 | Fraser et al. |
| 8,524,653 B2 | 9/2013 | Nash et al. |
| 8,583,380 B2 | 11/2013 | Stephan et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 | 10/2014 | Guerlavais et al. |
| 8,871,899 B2 | 10/2014 | Wang et al. |
| 8,889,632 B2 | 11/2014 | Bernal et al. |
| 8,895,699 B2 | 11/2014 | Verdine et al. |
| 8,927,500 B2 | 1/2015 | Guerlavais et al. |
| 8,957,026 B2 | 2/2015 | Verdine et al. |
| 8,987,414 B2 | 3/2015 | Guerlavais et al. |
| 9,023,988 B2 | 5/2015 | Nash |
| 9,096,684 B2 | 8/2015 | Kawahata et al. |
| 9,163,330 B2 | 10/2015 | Verdine et al. |
| 9,175,045 B2 | 11/2015 | Nash et al. |
| 9,175,047 B2 | 11/2015 | Nash et al. |
| 9,175,056 B2 | 11/2015 | Nash |
| 9,206,223 B2 | 12/2015 | Nash et al. |
| 9,273,031 B2 | 3/2016 | Errico et al. |
| 9,273,099 B2 | 3/2016 | Walensky et al. |
| 9,371,568 B2 | 6/2016 | Gaulis et al. |
| 9,381,228 B2 | 7/2016 | Robson et al. |
| 9,394,336 B2 | 7/2016 | Nash et al. |
| 9,408,885 B2 | 8/2016 | Marine et al. |
| 9,458,202 B2 | 10/2016 | Nash et al. |
| 9,464,115 B2 | 10/2016 | Walensky et al. |
| 9,486,445 B2 | 11/2016 | Higgins et al. |
| 9,493,509 B2 | 11/2016 | Nash et al. |
| 9,505,801 B2 | 11/2016 | Verdine et al. |
| 9,505,804 B2 | 11/2016 | Guerlavais et al. |
| 9,522,947 B2 | 12/2016 | Kawahata et al. |
| 9,527,896 B2 | 12/2016 | Bernal et al. |
| 9,556,227 B2 | 1/2017 | Verdine et al. |
| 9,604,919 B2 | 3/2017 | Darlak et al. |
| 9,675,661 B2 | 6/2017 | Nash et al. |
| 2001/0047030 A1 | 11/2001 | Hay et al. |
| 2002/0002198 A1 | 1/2002 | Parr |
| 2002/0013320 A1 | 1/2002 | Busch et al. |
| 2002/0016298 A1 | 2/2002 | Hay et al. |
| 2002/0028838 A1 | 3/2002 | MacLean et al. |
| 2002/0055156 A1 | 5/2002 | Jaspers et al. |
| 2002/0061838 A1 | 5/2002 | Holmquist et al. |
| 2002/0091090 A1 | 7/2002 | Cole et al. |
| 2002/0091125 A1 | 7/2002 | Hay et al. |
| 2002/0094992 A1 | 7/2002 | MacLean |
| 2002/0098580 A1 | 7/2002 | Nandabalan et al. |
| 2002/0103221 A1 | 8/2002 | Petrie et al. |

(56) References Cited

U.S. PATENT DOCUMENTS

| | | |
|---|---|---|
| 2002/0128206 A1 | 9/2002 | Hay et al. |
| 2002/0132977 A1 | 9/2002 | Yuan et al. |
| 2002/0137665 A1 | 9/2002 | Evans et al. |
| 2002/0173618 A1 | 11/2002 | Rivier et al. |
| 2003/0027766 A1 | 2/2003 | Ioannides et al. |
| 2003/0060432 A1 | 3/2003 | Tocque et al. |
| 2003/0074679 A1 | 4/2003 | Schwartz et al. |
| 2003/0083241 A1 | 5/2003 | Young |
| 2003/0105114 A1 | 6/2003 | Carpino et al. |
| 2003/0144331 A1 | 7/2003 | Gudkov et al. |
| 2003/0148948 A1 | 8/2003 | Schwartz et al. |
| 2003/0157717 A1 | 8/2003 | Draghia-Akli |
| 2003/0166138 A1 | 9/2003 | Kinsella et al. |
| 2003/0176318 A1 | 9/2003 | Gudkov et al. |
| 2003/0181367 A1 | 9/2003 | O'Mahony et al. |
| 2003/0186865 A1 | 10/2003 | Acosta et al. |
| 2003/0204063 A1 | 10/2003 | Gravel et al. |
| 2004/0018967 A1 | 1/2004 | Enright et al. |
| 2004/0023887 A1 | 2/2004 | Pillutla et al. |
| 2004/0038901 A1 | 2/2004 | Basler et al. |
| 2004/0038918 A1 | 2/2004 | Draghia-Akli et al. |
| 2004/0058877 A1 | 3/2004 | Hay et al. |
| 2004/0067503 A1 | 4/2004 | Tan et al. |
| 2004/0081652 A1 | 4/2004 | Zack et al. |
| 2004/0091530 A1 | 5/2004 | Am et al. |
| 2004/0106159 A1 | 6/2004 | Kern et al. |
| 2004/0106548 A1 | 6/2004 | Schmidt et al. |
| 2004/0115135 A1 | 6/2004 | Quay |
| 2004/0122062 A1 | 6/2004 | MacLean et al. |
| 2004/0146971 A1 | 7/2004 | Lane et al. |
| 2004/0152708 A1 | 8/2004 | Li et al. |
| 2004/0157834 A1 | 8/2004 | Hay et al. |
| 2004/0170653 A1 | 9/2004 | Stanislawski et al. |
| 2004/0170971 A1 | 9/2004 | Kinzler et al. |
| 2004/0171530 A1 | 9/2004 | Coy et al. |
| 2004/0171809 A1 | 9/2004 | Korsmeyer et al. |
| 2004/0195413 A1 | 10/2004 | Reed et al. |
| 2004/0204358 A1 | 10/2004 | Brown et al. |
| 2004/0208866 A1 | 10/2004 | Jaspers et al. |
| 2004/0228866 A1 | 11/2004 | Lu |
| 2004/0235746 A1 | 11/2004 | Hawiger et al. |
| 2004/0248198 A1 | 12/2004 | Kriwacki et al. |
| 2004/0248788 A1 | 12/2004 | Vickers et al. |
| 2004/0265931 A1 | 12/2004 | Gu et al. |
| 2005/0009739 A1 | 1/2005 | Wang et al. |
| 2005/0013820 A1 | 1/2005 | Holoshitz et al. |
| 2005/0014686 A1 | 1/2005 | Albert et al. |
| 2005/0031549 A1 | 2/2005 | Quay et al. |
| 2005/0037383 A1 | 2/2005 | Taremi et al. |
| 2005/0043231 A1 | 2/2005 | Cutfield et al. |
| 2005/0048618 A1 | 3/2005 | Jaspers et al. |
| 2005/0049177 A1 | 3/2005 | Bachovchin et al. |
| 2005/0054581 A1 | 3/2005 | Hay et al. |
| 2005/0059605 A1 | 3/2005 | Peri et al. |
| 2005/0065180 A1 | 3/2005 | Lee |
| 2005/0080007 A1 | 4/2005 | Ghigo et al. |
| 2005/0089511 A1 | 4/2005 | Roth et al. |
| 2005/0119167 A1 | 6/2005 | Abbenante et al. |
| 2005/0137137 A1 | 6/2005 | Lane et al. |
| 2005/0147581 A1 | 7/2005 | Zamiri et al. |
| 2005/0164298 A1 | 7/2005 | Golz et al. |
| 2005/0176075 A1 | 8/2005 | Jones et al. |
| 2005/0203009 A1 | 9/2005 | Pan et al. |
| 2005/0222224 A1 | 10/2005 | Gudkov et al. |
| 2005/0222427 A1 | 10/2005 | Sharpless et al. |
| 2005/0227932 A1 | 10/2005 | Lu et al. |
| 2005/0245438 A1 | 11/2005 | Rivier et al. |
| 2005/0245457 A1 | 11/2005 | Deghenghi |
| 2005/0245764 A1 | 11/2005 | Yamashita et al. |
| 2005/0250680 A1 | 11/2005 | Walensky et al. |
| 2005/0261201 A1 | 11/2005 | Polvino et al. |
| 2005/0277764 A1 | 12/2005 | Boyd et al. |
| 2006/0008848 A1 | 1/2006 | Verdine et al. |
| 2006/0014675 A1 | 1/2006 | Arora et al. |
| 2006/0025344 A1 | 2/2006 | Lange et al. |
| 2006/0058219 A1 | 3/2006 | Miller et al. |
| 2006/0058221 A1 | 3/2006 | Miller et al. |
| 2006/0073518 A1 | 4/2006 | Timmerman et al. |
| 2006/0100143 A1 | 5/2006 | Lu et al. |
| 2006/0111411 A1 | 5/2006 | Cooper et al. |
| 2006/0128615 A1 | 6/2006 | Gaudreau |
| 2006/0142181 A1 | 6/2006 | Miller et al. |
| 2006/0142182 A1 | 6/2006 | Miller et al. |
| 2006/0148715 A1 | 7/2006 | Tweardy |
| 2006/0149039 A1 | 7/2006 | Hunter et al. |
| 2006/0155107 A1 | 7/2006 | Rivier et al. |
| 2006/0189511 A1 | 8/2006 | Koblish et al. |
| 2006/0210641 A1 | 9/2006 | Shalaby |
| 2006/0217296 A1 | 9/2006 | Jansson |
| 2006/0233779 A1 | 10/2006 | Ben-Avraham et al. |
| 2006/0247170 A1 | 11/2006 | Guyon et al. |
| 2006/0293380 A1 | 12/2006 | Nantermet et al. |
| 2007/0004765 A1 | 1/2007 | Graffner-Nordberg et al. |
| 2007/0006332 A1 | 1/2007 | O'Neill |
| 2007/0020620 A1 | 1/2007 | Finn et al. |
| 2007/0025991 A1 | 2/2007 | Pothoulakis et al. |
| 2007/0032417 A1 | 2/2007 | Baell |
| 2007/0037857 A1 | 2/2007 | Perrissoud et al. |
| 2007/0041902 A1 | 2/2007 | Goodman et al. |
| 2007/0060512 A1 | 3/2007 | Sadeghi et al. |
| 2007/0129324 A1 | 6/2007 | Boyd et al. |
| 2007/0161544 A1 | 7/2007 | Wipf et al. |
| 2007/0161551 A1 | 7/2007 | De |
| 2007/0191283 A1 | 8/2007 | Polvino |
| 2007/0197772 A1 | 8/2007 | Arora et al. |
| 2007/0208061 A2 | 9/2007 | Perrissoud et al. |
| 2007/0238662 A1 | 10/2007 | Mintz |
| 2007/0274915 A1 | 11/2007 | Rao et al. |
| 2008/0015265 A1 | 1/2008 | Rubin et al. |
| 2008/0026993 A9 | 1/2008 | Guyon et al. |
| 2008/0032931 A1 | 2/2008 | Steward et al. |
| 2008/0081038 A1 | 4/2008 | Cho et al. |
| 2008/0085279 A1 | 4/2008 | Boyd et al. |
| 2008/0090756 A1 | 4/2008 | Coy et al. |
| 2008/0132485 A1 | 6/2008 | Wang et al. |
| 2008/0161426 A1 | 7/2008 | Gudkov et al. |
| 2008/0167222 A1 | 7/2008 | Lussier et al. |
| 2008/0171700 A1 | 7/2008 | Nilsson et al. |
| 2008/0194553 A1 | 8/2008 | Gillessen et al. |
| 2008/0194672 A1 | 8/2008 | Hoveyda et al. |
| 2008/0213175 A1 | 9/2008 | Kolb et al. |
| 2008/0234183 A1 | 9/2008 | Hallbrink et al. |
| 2008/0242598 A1 | 10/2008 | Fairlie et al. |
| 2008/0250515 A1 | 10/2008 | Reed |
| 2008/0260638 A1 | 10/2008 | Rivier et al. |
| 2008/0260820 A1 | 10/2008 | Borrelly et al. |
| 2008/0261873 A1 | 10/2008 | Geesaman |
| 2008/0262200 A1 | 10/2008 | Nash |
| 2008/0299040 A1 | 12/2008 | Rivier et al. |
| 2008/0300193 A1 | 12/2008 | Ahn et al. |
| 2008/0300194 A1 | 12/2008 | Mann et al. |
| 2008/0305490 A1 | 12/2008 | Burrell et al. |
| 2008/0311608 A1 | 12/2008 | Tocque et al. |
| 2009/0011985 A1 | 1/2009 | Abribat et al. |
| 2009/0047711 A1 | 2/2009 | Nash |
| 2009/0054331 A1 | 2/2009 | Chen et al. |
| 2009/0069245 A1 | 3/2009 | Bowers et al. |
| 2009/0081168 A1 | 3/2009 | Sheppard et al. |
| 2009/0088383 A1 | 4/2009 | Abribat et al. |
| 2009/0088553 A1 | 4/2009 | Nash |
| 2009/0131478 A1 | 5/2009 | Dong et al. |
| 2009/0149630 A1 | 6/2009 | Walensky et al. |
| 2009/0156483 A1 | 6/2009 | Dong et al. |
| 2009/0156795 A1 | 6/2009 | Jaspers et al. |
| 2009/0170757 A1 | 7/2009 | Fraser et al. |
| 2009/0175821 A1 | 7/2009 | Bridon et al. |
| 2009/0176964 A1 | 7/2009 | Walensky et al. |
| 2009/0198050 A1 | 8/2009 | Marsault et al. |
| 2009/0221512 A1 | 9/2009 | Acosta et al. |
| 2009/0221689 A1 | 9/2009 | Marsault et al. |
| 2009/0240027 A1 | 9/2009 | Marsault et al. |
| 2009/0253623 A1 | 10/2009 | Abribat et al. |
| 2009/0275511 A1 | 11/2009 | Dong |
| 2009/0275519 A1 | 11/2009 | Nash et al. |

(56) References Cited

U.S. PATENT DOCUMENTS

| | | |
|---|---|---|
| 2009/0275648 A1 | 11/2009 | Fraser et al. |
| 2009/0305300 A1 | 12/2009 | Larsen |
| 2009/0311174 A1 | 12/2009 | Allen |
| 2009/0326192 A1 | 12/2009 | Nash et al. |
| 2009/0326193 A1 | 12/2009 | Maggio et al. |
| 2010/0010065 A1 | 1/2010 | Smith |
| 2010/0081611 A1 | 4/2010 | Bradner et al. |
| 2010/0087366 A1 | 4/2010 | Abribat et al. |
| 2010/0087381 A1 | 4/2010 | Polvino |
| 2010/0093057 A1 | 4/2010 | Beattie et al. |
| 2010/0093086 A1 | 4/2010 | Lin et al. |
| 2010/0152114 A1 | 6/2010 | Schally et al. |
| 2010/0158923 A1 | 6/2010 | Morimoto et al. |
| 2010/0168388 A1 | 7/2010 | Bernal et al. |
| 2010/0179168 A1 | 7/2010 | Blaney et al. |
| 2010/0184628 A1 | 7/2010 | Nash |
| 2010/0184645 A1 | 7/2010 | Verdine et al. |
| 2010/0204118 A1 | 8/2010 | Bevec |
| 2010/0210515 A1 | 8/2010 | Nash et al. |
| 2010/0216688 A1 | 8/2010 | Nash et al. |
| 2010/0234563 A1 | 9/2010 | Arora et al. |
| 2010/0239589 A1 | 9/2010 | Woods et al. |
| 2010/0267636 A1 | 10/2010 | Marsolais |
| 2010/0273704 A1 | 10/2010 | Korsmeyer et al. |
| 2010/0286362 A1 | 11/2010 | Boyd et al. |
| 2010/0298201 A1 | 11/2010 | Nash et al. |
| 2010/0298393 A1 | 11/2010 | Vanderklish et al. |
| 2010/0303791 A1 | 12/2010 | Francis et al. |
| 2010/0303794 A1 | 12/2010 | Francis et al. |
| 2010/0323964 A1 | 12/2010 | Vitali et al. |
| 2010/0331343 A1 | 12/2010 | Perrissoud et al. |
| 2011/0020435 A1 | 1/2011 | Maggio |
| 2011/0021529 A1 | 1/2011 | Lain et al. |
| 2011/0028753 A1 | 2/2011 | Verdine et al. |
| 2011/0046043 A1 | 2/2011 | Wang et al. |
| 2011/0065915 A1 | 3/2011 | Malcolmson et al. |
| 2011/0097389 A1 | 4/2011 | Sobol et al. |
| 2011/0105389 A1 | 5/2011 | Hoveyda et al. |
| 2011/0105390 A1 | 5/2011 | Lussier et al. |
| 2011/0130331 A1 | 6/2011 | Guyon et al. |
| 2011/0143992 A1 | 6/2011 | Taub et al. |
| 2011/0144303 A1 | 6/2011 | Nash et al. |
| 2011/0144306 A1 | 6/2011 | Verdine et al. |
| 2011/0151480 A1 | 6/2011 | Sheppard et al. |
| 2011/0158973 A1 | 6/2011 | Madec et al. |
| 2011/0160135 A1 | 6/2011 | Johnstone et al. |
| 2011/0165137 A1 | 7/2011 | Madec et al. |
| 2011/0166063 A1 | 7/2011 | Bossard et al. |
| 2011/0171191 A1 | 7/2011 | Johnstone et al. |
| 2011/0183917 A1 | 7/2011 | Lu et al. |
| 2011/0195080 A1 | 8/2011 | Haffer et al. |
| 2011/0218155 A1 | 9/2011 | Walensky et al. |
| 2011/0223149 A1 | 9/2011 | Nash et al. |
| 2011/0230415 A1 | 9/2011 | Berlanga et al. |
| 2011/0243845 A1 | 10/2011 | Goodman et al. |
| 2011/0245159 A1 | 10/2011 | Hoveyda et al. |
| 2011/0245175 A1 | 10/2011 | Arora et al. |
| 2011/0245459 A1 | 10/2011 | Marsault et al. |
| 2011/0245477 A1 | 10/2011 | Hoveyda et al. |
| 2011/0250685 A1 | 10/2011 | Nash |
| 2011/0251252 A1 | 10/2011 | Wang et al. |
| 2011/0263815 A1 | 10/2011 | Nash |
| 2011/0269683 A1 | 11/2011 | Rivier et al. |
| 2011/0313167 A1 | 12/2011 | Doemling |
| 2012/0004174 A1 | 1/2012 | Abribat et al. |
| 2012/0010157 A1 | 1/2012 | Polvino et al. |
| 2012/0040889 A1 | 2/2012 | Nash et al. |
| 2012/0052548 A1 | 3/2012 | Steward et al. |
| 2012/0077745 A1 | 3/2012 | Polvino |
| 2012/0082636 A1 | 4/2012 | Walensky et al. |
| 2012/0083494 A1 | 4/2012 | Aicher et al. |
| 2012/0101047 A1 | 4/2012 | Nash et al. |
| 2012/0115783 A1 | 5/2012 | Nash et al. |
| 2012/0115793 A1 | 5/2012 | Nash et al. |
| 2012/0156197 A1 | 6/2012 | Errico et al. |
| 2012/0165566 A1 | 6/2012 | Marsault et al. |
| 2012/0172311 A1 | 7/2012 | Nash et al. |
| 2012/0178700 A1 | 7/2012 | Nash et al. |
| 2012/0226066 A1 | 9/2012 | Marsault et al. |
| 2012/0226067 A1 | 9/2012 | Marsault et al. |
| 2012/0226072 A1 | 9/2012 | Marsault et al. |
| 2012/0238507 A1 | 9/2012 | Fairlie et al. |
| 2012/0264674 A1 | 10/2012 | Nash et al. |
| 2012/0264738 A1 | 10/2012 | Sugimoto et al. |
| 2012/0270800 A1 | 10/2012 | Verdine et al. |
| 2012/0283269 A1 | 11/2012 | Blagosklonny et al. |
| 2012/0328692 A1 | 12/2012 | Lu et al. |
| 2013/0005943 A1 | 1/2013 | Arora et al. |
| 2013/0023646 A1 | 1/2013 | Nash et al. |
| 2013/0039851 A1 | 2/2013 | Maggio |
| 2013/0072439 A1 | 3/2013 | Nash et al. |
| 2013/0096050 A1 | 4/2013 | Shandler |
| 2013/0123169 A1 | 5/2013 | Kawahata et al. |
| 2013/0123196 A1 | 5/2013 | Arora et al. |
| 2013/0177979 A1 | 7/2013 | Turkson |
| 2013/0210743 A1 | 8/2013 | Guerlavais et al. |
| 2013/0211046 A1 | 8/2013 | Verdine et al. |
| 2013/0274205 A1 | 10/2013 | Guerlavais et al. |
| 2013/0330421 A1 | 12/2013 | Marine |
| 2013/0333419 A1 | 12/2013 | Koketsu et al. |
| 2014/0005118 A1 | 1/2014 | Verdine et al. |
| 2014/0011979 A1 | 1/2014 | Verdine et al. |
| 2014/0018302 A1 | 1/2014 | Walensky et al. |
| 2014/0051828 A1 | 2/2014 | Arora et al. |
| 2014/0128581 A1 | 5/2014 | Darlak et al. |
| 2014/0141980 A1 | 5/2014 | Stephan et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0296160 A1 | 10/2014 | Walensky et al. |
| 2014/0323701 A1 | 10/2014 | Nash et al. |
| 2014/0378390 A1 | 12/2014 | Guerlavais et al. |
| 2015/0004158 A1 | 1/2015 | Shipp et al. |
| 2015/0038430 A1 | 2/2015 | Nash et al. |
| 2015/0039946 A1 | 2/2015 | Rao et al. |
| 2015/0051155 A1 | 2/2015 | Guerlavais et al. |
| 2015/0056612 A1 | 2/2015 | Shen et al. |
| 2015/0119551 A1 | 4/2015 | Bernal et al. |
| 2015/0157603 A1 | 6/2015 | Higgins et al. |
| 2015/0183825 A1 | 7/2015 | Guerlavais et al. |
| 2015/0225471 A1 | 8/2015 | Liang et al. |
| 2015/0239937 A1 | 8/2015 | Verdine et al. |
| 2015/0284437 A1 | 10/2015 | Verdine et al. |
| 2015/0285810 A1 | 10/2015 | Lu et al. |
| 2015/0376227 A1 | 12/2015 | Verdine et al. |
| 2016/0024153 A1 | 1/2016 | Verdine et al. |
| 2016/0030433 A1 | 2/2016 | Koff et al. |
| 2016/0031936 A1 | 2/2016 | Nash |
| 2016/0038498 A1 | 2/2016 | Bussey et al. |
| 2016/0052970 A1 | 2/2016 | Guerlavais et al. |
| 2016/0068573 A1 | 3/2016 | Nash et al. |
| 2016/0095896 A1 | 4/2016 | Nash et al. |
| 2016/0096873 A1 | 4/2016 | Nash et al. |
| 2016/0101145 A1 | 4/2016 | Annis et al. |
| 2016/0108089 A1 | 4/2016 | Nash et al. |
| 2016/0115204 A1 | 4/2016 | Nash et al. |
| 2016/0115553 A1 | 4/2016 | Stephan et al. |
| 2016/0115554 A1 | 4/2016 | Stephan et al. |
| 2016/0115556 A1 | 4/2016 | Erlander et al. |
| 2016/0122830 A1 | 5/2016 | Stephan et al. |
| 2016/0137710 A1 | 5/2016 | Kawahata et al. |
| 2016/0193283 A1 | 7/2016 | Chen et al. |
| 2016/0250278 A1 | 9/2016 | Nash et al. |
| 2016/0251399 A1 | 9/2016 | Nash et al. |
| 2016/0257716 A1 | 9/2016 | Guerlavais et al. |
| 2016/0265065 A1 | 9/2016 | Bandla et al. |
| 2016/0287569 A1 | 10/2016 | Caenepeel et al. |
| 2016/0289274 A1 | 10/2016 | Nash |
| 2016/0289770 A1 | 10/2016 | Gaulis et al. |
| 2016/0304564 A1 | 10/2016 | Nash |
| 2016/0333049 A1 | 11/2016 | Chen et al. |
| 2016/0339023 A1 | 11/2016 | Li et al. |
| 2016/0362749 A1 | 12/2016 | Stephan et al. |
| 2017/0002042 A1 | 1/2017 | Annis et al. |

(56) References Cited

U.S. PATENT DOCUMENTS

| | | |
|---|---|---|
| 2017/0008930 A1 | 1/2017 | Walensky et al. |
| 2017/0015716 A1 | 1/2017 | Walensky et al. |
| 2017/0037086 A1 | 2/2017 | Kawahata et al. |
| 2017/0037105 A1 | 2/2017 | Samant |
| 2017/0066799 A1 | 3/2017 | Verdine et al. |
| 2017/0081379 A1 | 3/2017 | Bernal et al. |
| 2017/0088581 A1 | 3/2017 | Verdine et al. |

FOREIGN PATENT DOCUMENTS

| | | | |
|---|---|---|---|
| CN | 1583730 A | | 2/2005 |
| CN | 1906209 A | | 1/2007 |
| CN | 101636407 A | | 1/2010 |
| CN | 102223891 A | | 10/2011 |
| CN | 102399283 A | | 4/2012 |
| CN | 102399284 A | | 4/2012 |
| CZ | 9700369 A3 | | 9/1998 |
| EP | 0467699 A2 | | 1/1992 |
| EP | 0467699 A3 | | 2/1993 |
| EP | 0528312 A2 | | 2/1993 |
| EP | 0552417 A1 | | 7/1993 |
| EP | 0352014 B1 | | 3/1994 |
| EP | 0729972 A1 | | 9/1996 |
| EP | 0643726 B1 | | 8/1999 |
| EP | 0977580 B1 | | 4/2003 |
| EP | 1321474 A1 | | 6/2003 |
| EP | 1452868 A2 | | 9/2004 |
| EP | 1541692 A1 | | 6/2005 |
| EP | 1602663 A1 | | 12/2005 |
| EP | 1609802 A1 | | 12/2005 |
| EP | 1243923 B1 | | 3/2006 |
| EP | 1180016 B1 | | 9/2006 |
| EP | 0958305 B1 | | 6/2008 |
| EP | 2091552 A2 | | 8/2009 |
| EP | 2100901 A1 | | 9/2009 |
| EP | 2310407 A2 | | 4/2011 |
| EP | 1597585 B1 | | 6/2011 |
| EP | 2377849 A2 | | 10/2011 |
| EP | 2637680 A2 | | 9/2013 |
| EP | 3027212 A1 | | 6/2016 |
| EP | 2474624 B1 | | 8/2016 |
| EP | 3059322 A1 | | 8/2016 |
| EP | 2474625 B1 | | 11/2016 |
| EP | 2245464 B1 | | 12/2016 |
| JP | 2002524391 A | | 8/2002 |
| JP | 2008501623 A | | 1/2008 |
| JP | 2008096423 A | | 4/2008 |
| JP | 2010120881 A | | 6/2010 |
| JP | 2010519318 A | | 6/2010 |
| WO | WO-8909233 A1 | | 10/1989 |
| WO | WO-8912675 A1 | | 12/1989 |
| WO | WO-9206998 A1 | | 4/1992 |
| WO | WO-9213878 A2 | | 8/1992 |
| WO | WO-9301203 A1 | | 1/1993 |
| WO | WO-9307170 A1 | | 4/1993 |
| WO | WO-9422910 A1 | | 10/1994 |
| WO | WO-9425482 A1 | | 11/1994 |
| WO | WO-9500534 A1 | | 1/1995 |
| WO | WO-9522546 A1 | | 8/1995 |
| WO | WO-9602642 A1 | | 2/1996 |
| WO | WO-9620951 A1 | | 7/1996 |
| WO | WO-9628449 A1 | | 9/1996 |
| WO | WO-9632126 A1 | | 10/1996 |
| WO | WO-9634878 A1 | | 11/1996 |
| WO | WO-9700267 A1 | | 1/1997 |
| WO | WO-9713537 A1 | | 4/1997 |
| WO | WO-9714794 A1 | | 4/1997 |
| WO | WO-9726002 A1 | | 7/1997 |
| WO | WO-9730072 A1 | | 8/1997 |
| WO | WO-9737705 A1 | | 10/1997 |
| WO | WO-9801467 A2 | | 1/1998 |
| WO | WO-9817625 A1 | | 4/1998 |
| WO | WO-9846631 A1 | | 10/1998 |
| WO | WO-9847525 A1 | | 10/1998 |
| WO | WO-9914259 A1 | | 3/1999 |
| WO | WO-9934833 A1 | | 7/1999 |
| WO | WO-9934850 A1 | | 7/1999 |
| WO | WO-9963929 A2 | | 12/1999 |
| WO | WO-0006187 A2 | | 2/2000 |
| WO | WO-0006187 A3 | | 5/2000 |
| WO | WO-02064790 A2 | | 8/2002 |
| WO | WO-02070547 A1 | | 9/2002 |
| WO | WO-02072597 A2 | | 9/2002 |
| WO | WO-02064790 A3 | | 5/2003 |
| WO | WO-03054000 A1 | | 7/2003 |
| WO | WO-03059933 A2 | | 7/2003 |
| WO | WO-03070892 A2 | | 8/2003 |
| WO | WO-03102538 A2 | | 12/2003 |
| WO | WO-03106491 A2 | | 12/2003 |
| WO | WO-03059933 A3 | | 1/2004 |
| WO | WO-2004026896 A2 | | 4/2004 |
| WO | WO-2004037754 A2 | | 5/2004 |
| WO | WO-2004041275 A1 | | 5/2004 |
| WO | WO-2004058804 A1 | | 7/2004 |
| WO | WO-2004077062 A2 | | 9/2004 |
| WO | WO-2004037754 A3 | | 10/2004 |
| WO | WO-03070892 A3 | | 11/2004 |
| WO | WO-03106491 A3 | | 12/2004 |
| WO | WO-2004077062 A3 | | 1/2005 |
| WO | WO-2005007675 A2 | | 1/2005 |
| WO | WO-2004077062 B1 | | 2/2005 |
| WO | WO-2005012335 A1 | | 2/2005 |
| WO | WO-2005035568 A1 | | 4/2005 |
| WO | WO-2005040202 A2 | | 5/2005 |
| WO | WO-2005044839 A2 | | 5/2005 |
| WO | WO-2005040202 A3 | | 6/2005 |
| WO | WO-2005007675 A3 | | 7/2005 |
| WO | WO-2005044839 A3 | | 7/2005 |
| WO | WO-2005074521 A2 | | 8/2005 |
| WO | WO-2005085457 A2 | | 9/2005 |
| WO | WO-2005090388 A1 | | 9/2005 |
| WO | WO-2005097173 A2 | | 10/2005 |
| WO | WO-2005118620 A2 | | 12/2005 |
| WO | WO-2005118625 A1 | | 12/2005 |
| WO | WO-2005118634 A2 | | 12/2005 |
| WO | WO-2006009645 A1 | | 1/2006 |
| WO | WO-2006009674 A1 | | 1/2006 |
| WO | WO-2006042408 A1 | | 4/2006 |
| WO | WO-2005118634 A3 | | 5/2006 |
| WO | WO-2005118620 A3 | | 6/2006 |
| WO | WO-2006078161 A1 | | 7/2006 |
| WO | WO-2006103666 A2 | | 10/2006 |
| WO | WO-2006137974 A2 | | 12/2006 |
| WO | WO-2006103666 A3 | | 3/2007 |
| WO | WO-2007141533 A2 | | 12/2007 |
| WO | WO-2008013454 A2 | | 1/2008 |
| WO | WO-2008014216 A1 | | 1/2008 |
| WO | WO-2008045238 A2 | | 4/2008 |
| WO | WO-2008061192 A2 | | 5/2008 |
| WO | WO-2008074895 A1 | | 6/2008 |
| WO | WO-2008076904 A1 | | 6/2008 |
| WO | WO-2007141533 A3 | | 7/2008 |
| WO | WO-2008061192 A3 | | 7/2008 |
| WO | WO-2008092281 A1 | | 8/2008 |
| WO | WO-2008095063 A1 | | 8/2008 |
| WO | WO-2008104000 A2 | | 8/2008 |
| WO | WO-2008106507 A2 | | 9/2008 |
| WO | WO-2008121767 A2 | | 10/2008 |
| WO | WO-2008130464 A1 | | 10/2008 |
| WO | WO-2008137633 A2 | | 11/2008 |
| WO | WO-2008121767 A3 | | 1/2009 |
| WO | WO-2009009727 A2 | | 1/2009 |
| WO | WO-2009031916 A1 | | 3/2009 |
| WO | WO-2009033667 A2 | | 3/2009 |
| WO | WO-2009033668 A2 | | 3/2009 |
| WO | WO-2009042237 A2 | | 4/2009 |
| WO | WO-2009009727 A3 | | 5/2009 |
| WO | WO-2009089004 A1 | | 7/2009 |
| WO | WO-2009033667 A3 | | 8/2009 |
| WO | WO-2009033668 A3 | | 8/2009 |
| WO | WO-2009099677 A2 | | 8/2009 |
| WO | WO-2009110952 A2 | | 9/2009 |
| WO | WO-2009126292 A2 | | 10/2009 |
| WO | WO-2009129311 A2 | | 10/2009 |

(56) References Cited

FOREIGN PATENT DOCUMENTS

| | | |
|---|---|---|
| WO | WO-2009137532 A1 | 11/2009 |
| WO | WO-2009149214 A2 | 12/2009 |
| WO | WO-2009149339 A2 | 12/2009 |
| WO | WO-2010011313 A2 | 1/2010 |
| WO | WO-2010013011 A1 | 2/2010 |
| WO | WO-2010033617 A2 | 3/2010 |
| WO | WO-2010033879 A2 | 3/2010 |
| WO | WO-2010034026 A1 | 3/2010 |
| WO | WO-2010034028 A1 | 3/2010 |
| WO | WO-2010034029 A1 | 3/2010 |
| WO | WO-2010034031 A1 | 3/2010 |
| WO | WO-2010034032 A2 | 3/2010 |
| WO | WO-2010034034 A1 | 3/2010 |
| WO | WO-2010058819 A1 | 5/2010 |
| WO | WO-2010060112 A1 | 5/2010 |
| WO | WO-2010065572 A1 | 6/2010 |
| WO | WO-2010068684 A2 | 6/2010 |
| WO | WO-2009129311 A3 | 7/2010 |
| WO | WO-2010083347 A2 | 7/2010 |
| WO | WO-2010083501 A2 | 7/2010 |
| WO | WO-2010100351 A1 | 9/2010 |
| WO | WO-2010107485 A1 | 9/2010 |
| WO | WO-2010132580 A2 | 11/2010 |
| WO | WO-2010011313 A3 | 12/2010 |
| WO | WO-2011005219 A1 | 1/2011 |
| WO | WO-2011008260 A2 | 1/2011 |
| WO | WO-2011008260 A3 | 3/2011 |
| WO | WO-2011023677 A1 | 3/2011 |
| WO | WO-2011038049 A1 | 3/2011 |
| WO | WO-2011047215 A1 | 4/2011 |
| WO | WO-2011060049 A2 | 5/2011 |
| WO | WO-2011061139 A1 | 5/2011 |
| WO | WO-2011076786 A1 | 6/2011 |
| WO | WO-2011090297 A2 | 7/2011 |
| WO | WO-2011101297 A1 | 8/2011 |
| WO | WO-2011106650 A2 | 9/2011 |
| WO | WO-2011133948 A2 | 10/2011 |
| WO | WO-2011143208 A1 | 11/2011 |
| WO | WO-2011143209 A1 | 11/2011 |
| WO | WO-2011153491 A2 | 12/2011 |
| WO | WO-2011159917 A2 | 12/2011 |
| WO | WO-2011161699 A2 | 12/2011 |
| WO | WO-2011162968 A1 | 12/2011 |
| WO | WO-2011163012 A2 | 12/2011 |
| WO | WO-2011133948 A3 | 1/2012 |
| WO | WO-2012012352 A2 | 1/2012 |
| WO | WO-2012016186 A1 | 2/2012 |
| WO | WO-2012021874 A1 | 2/2012 |
| WO | WO-2012021875 A1 | 2/2012 |
| WO | WO-2012021876 A2 | 2/2012 |
| WO | WO-2012033525 A2 | 3/2012 |
| WO | WO-2012034954 A1 | 3/2012 |
| WO | WO-2012037519 A2 | 3/2012 |
| WO | WO-2012038307 A1 | 3/2012 |
| WO | WO-2012040459 A2 | 3/2012 |
| WO | WO-2011153491 A3 | 4/2012 |
| WO | WO-2012045018 A1 | 4/2012 |
| WO | WO-2012047587 A2 | 4/2012 |
| WO | WO-2012051405 A1 | 4/2012 |
| WO | WO-2012059696 A1 | 5/2012 |
| WO | WO-2012065022 A2 | 5/2012 |
| WO | WO-2012065181 A2 | 5/2012 |
| WO | WO-2012066095 A1 | 5/2012 |
| WO | WO-2012040459 A3 | 6/2012 |
| WO | WO-2012076513 A1 | 6/2012 |
| WO | WO-2012080376 A1 | 6/2012 |
| WO | WO-2012080389 A1 | 6/2012 |
| WO | WO-2012083078 A2 | 6/2012 |
| WO | WO-2012083181 A1 | 6/2012 |
| WO | WO-2011159917 A3 | 7/2012 |
| WO | WO-2012094755 A1 | 7/2012 |
| WO | WO-2012037519 A3 | 8/2012 |
| WO | WO-2012121057 A1 | 9/2012 |
| WO | WO-2012122059 A1 | 9/2012 |
| WO | WO-2012149563 A1 | 11/2012 |
| WO | WO-2012173846 A2 | 12/2012 |
| WO | WO-2012174423 A1 | 12/2012 |
| WO | WO-2012175962 A1 | 12/2012 |
| WO | WO-2013033645 A1 | 3/2013 |
| WO | WO-2013036208 A1 | 3/2013 |
| WO | WO-2013049250 A1 | 4/2013 |
| WO | WO-2013059525 A1 | 4/2013 |
| WO | WO-2013059530 A2 | 4/2013 |
| WO | WO-2013123266 A1 | 8/2013 |
| WO | WO-2013123267 A1 | 8/2013 |
| WO | WO-2013166319 A1 | 11/2013 |
| WO | WO-2014020502 A2 | 2/2014 |
| WO | WO-2014052647 A2 | 4/2014 |
| WO | WO-2014055564 A1 | 4/2014 |
| WO | WO-2014071241 A1 | 5/2014 |
| WO | WO-2014138429 A2 | 9/2014 |
| WO | WO-2014144121 A2 | 9/2014 |
| WO | WO-2015000945 A1 | 1/2015 |
| WO | WO-2015108175 A1 | 7/2015 |
| WO | WO-2015157508 A1 | 10/2015 |
| WO | WO-2015179799 A1 | 11/2015 |
| WO | WO-2015198266 A1 | 12/2015 |
| WO | WO-2016040892 A1 | 3/2016 |
| WO | WO-2016049355 A1 | 3/2016 |
| WO | WO-2016049359 A1 | 3/2016 |
| WO | WO-2016055497 A1 | 4/2016 |
| WO | WO-2016056673 A1 | 4/2016 |
| WO | WO-2016073184 A1 | 5/2016 |
| WO | WO-2016105503 A1 | 6/2016 |
| WO | WO-2016154058 A1 | 9/2016 |
| WO | WO-2017004548 A1 | 1/2017 |
| WO | WO-2017004591 A2 | 1/2017 |
| WO | WO-2017023933 A2 | 2/2017 |
| WO | WO-2017040990 A1 | 3/2017 |
| WO | WO-2017044633 A1 | 3/2017 |

OTHER PUBLICATIONS

Altschul et al. Basic local alignment search tool. J Mol Biol215(3):403-410 (1990).
Andrews et al. Forming Stable Helical Peptide Using Natural and Artificial Amino Acids. Tetrahedron. 1999;55:11711-11743.
Angell, et al. Peptidomimetics via copper-catalyzed azide-alkyne cycloadditions. Chem Soc Rev. Oct. 2007;36(10):1674-89.
Angell, et al. Ring closure to beta-turn mimics via copper-catalyzed azide/alkyne cycloadditions. J Org Chem. Nov. 11, 2005;70(23):9595-8.
Annis, et al. ALIS: An Affinity Selection-Mass Spectrometry System for the Discovery and Characterization of Protein-Ligand Interactions. In: Wanner, K. and Höfner, G. eds. Mass Spectrometry in Medicinal Chemistry. Wiley-VCH; 2007:121-156.
Armarego; et al., "Purification of Laboratory Chemicals", Butterworth-Heinemann, 2003, Fifth edition (Ch 1), 1-17.
Armstrong et al., X=Y–ZH Systems as potential 1,3-dipoles. 5. Intramolecular cycloadditions of imines of a-amino acid esters. Tetrahedron. 1985;41(17):3547-58.
Arosio, et al. Click chemistry to functionalise peptidomimetics. Tetrahedron Letters. 2006; 47:3697-3700.
Austin et al., "A Template for Stabilization of a Peptide α-Helix: Synthesis and Evaluation of Conformational Effects by Circular Dichroism and NMR," J. Am. Chem. Soc. 119:6461-6472 (1997).
Baek, et al. Structure of the stapled p53 peptide bound to Mdm2. J Am Chem Soc. Jan. 11, 2012;134(1):103-6. doi: 10.1021/ja2090367. Epub Dec. 14, 2011.
Baell, J.B. Prospects for Targeting the Bcl-2 Family of Proteins to Develop Novel cytotoxic drugs. Biochem Pharmacol. Sep. 2002;64(5-6):851-63.
Bakhshi, et al. Cloning the chromosomal breakpoint of t(14;18) human lymphomas: clustering around JH on chromosome 14 and near a transcriptional unit on 18. Cell. Jul. 1985;41(3):899-906.
Banerji et al. Synthesis of Cyclic β-Turn Mimics from L-Pro-Phe/Phe-L-Pro Derived Di- and Tripeptides via Ring Closing Metathesis: The Role of Chirality of the Phe Residue During Cyclization. Tetrahedron Lett. 2002; 43:6473-6477.

(56) References Cited

OTHER PUBLICATIONS

Barandon et al., Reduction of infarct size and prevention of cardiac rupture in transgenic mice overexpressing FrzA. Circulation. Nov. 4, 2003;108(18):2282-9. Epub Oct. 27, 2003.
Barker, et al. Cyclic RGD peptide analogues as antiplatelet antithrombotics. J Med Chem. May 29, 1992;35(11):2040-8. (Abstract only).
Belokon et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-21N-(N'-benzyl-prolypaminolbenzophenone (BPB) and Ni(II) complexes of Schiff's bases derived from BPB and amino acids. Tetrahedron: Asymmetry. 1998;9:4249-52.
Belokon, Y. N., et al., "Halo-substituted (S)-N-(2-benzoylphenyl)-1-benzylpyrolidine-2 carboxamides as new chiral auxiliaries for the asymmetric synthesis of (S)-a-amino acids," Russian Chemical Bulletin, International Edition, 51 (8): 1593-1599 (2002.
Berendsen et al., A glimpse of the Holy Grail? Science. Oct. 23, 1998;282(5389):642-3.
Bernal, et al. A stapled p53 helix overcomes HDMX-mediated suppression of p53. Cancer Cell. Nov. 16, 2010;18(5):411-22. doi: 10.1016/j.ccr.2010.10.024.
Blackwell, et al. Highly Efficient Synthesis of Covalently Cross-Linked Peptide Helices by Ring-Closing Metathesis. Angewandte Chemie International Edition. 1998; 37(23):3281-3284.
Bock, et al. 1,2,3-Triazoles as peptide bond isosteres: synthesis and biological evaluation of cyclotetrapeptide mimics. Org Biomol Chem. Mar. 21, 2007;5(6):971-5.
Boguslavsky, et al. Effect of peptide conformation on membrane permeability. J Pept Res. Jun. 2003;61(6):287-97.
Bossy-Wetzel et al. Assays for cytochrome c release from mitochondria during apoptosis. Methods Enzymol. 322:235-242 (2000).
Bossy-Wetzel, et al. Detection of apoptosis by annexin V labeling. Methods Enzymol. 2000;322:15-8.
Bottger, et al. Molecular characterization of the hdm2-p53 interaction. J Mol Biol. Jun. 27, 1997;269(5):744-56.
Bracken et al. Synthesis and nuclear magnetic resonance structure determination of an alpha-helical, bicyclic, lactam-bridged hexapeptide. JACS. 1994;116:6431-6432.
Bradley et al., Limits of cooperativity in a structurally modular protein: response of the Notch ankyrin domain to analogous alanine substitutions in each repeat. J Mol Biol. Nov. 22, 2002;324(2):373-86.
Brown, et al. A spirooligomer α-helix mimic that binds HDM2, penetrates human cells and stabilizes HDM2 in cell culture. PLoS One. 2012;7(10):e45948. doi: 10.1371/journal.pone.0045948. Epub Oct. 18, 2012.
Brown, et al. Stapled peptides with improved potency and specificity that activate p53. ACS Chem Biol. Mar. 15, 2013;8(3):506-12. doi: 10.1021/cb3005148. Epub Dec. 18, 2012.
Brunel, et al. Synthesis of constrained helical peptides by thioether ligation: application to analogs of gp41. Chem Commun (Camb). May 28, 2005;(20):2552-4. Epub Mar. 11, 2005.
Burger et aL, Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Burrage, et al. Biomimetic synthesis of lantibiotics. Chemistry. Apr. 14, 2000;6(8):1455-66.
Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).
Cantel, et al. Synthesis and Conformational Analysis of a Cyclic Peptide Obtained via i to i+4 Intramolecular Side-Chain to Side-Chain Azide-Alkyne 1,3-Dipolar Cycloaddition. JOC Featured Article. Published on the web May 20, 2008.
Carillo et al., The Multiple Sequence Alignment Problem in Biology. SIAM J Applied Math. 1988;48:1073-82.

CAS Registry No. 2176-37-6, STN Entry Date Nov. 16, 1984.
CAS Registry No. 2408-85-7, STN Entry Date Nov. 16, 1984.
CAS Registry No. 4727-05-3, STN Entry Date Nov. 16, 1984.
CAS Registry No. 561321-72-0, STN Entry Date Aug. 6, 2003.
CAS Registry No. 721918-14-5, STN Entry Date Aug. 4, 2004.
Chakrabartty et al., "Helix Capping Propensities in Peptides Parallel Those in Proteins," Proc. Nat'l Acad. Sci. USA 90:11332-11336 (1993).
Chang, et al. Stapled α-helical peptide drug development: a potent dual inhibitor of MDM2 and MDMX for p53-dependent cancer therapy. Proc Natl Acad Sci U S A. Sep. 3, 2013;110(36):E3445-54. doi: 10.1073/pnas.1303002110. Epub Aug. 14, 2013.
Chapman et al., "A Highly Stable Short α-Helix Constrained by a Main-chain Hydrogen-bond Surrogate," J. Am. Chem. Soc. 126:12252-12253 (2004).
Chapman, et al. Optimized synthesis of hydrogen-bond surrogate helices: surprising effects of microwave heating on the activity of Grubbs catalysts. Org Lett. Dec. 7, 2006;8(25):5825-8.
Chin & Schepartz, "Design and Evolution of a Miniature Bcl-2 Binding Protein," Angew. Chem. Int. Ed. 40(20):3806-3809 (2001).
Chin et al., "Circular Dichroism Spectra of Short, Fixed-nucleus Alanine Helices," Proc. Nat'l Acad. Sci. USA 99(24):15416-15421 (2002).
Choi, et al. Application of azide-alkyne cycloaddition 'click chemistry' for the synthesis of Grb2 SH2 domain-binding macrocycles. Bioorg Med Chem Lett. Oct. 15, 2006;16(20):5265-9.
Chu, et al. Peptide-formation on cysteine-containing peptide scaffolds. Orig Life Evol Biosph. Oct. 1999;29(5):441-9.
Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci U S A. Nov. 1985;82(21):7439-43.
Cline, et al. Effects of As(III) binding on alpha-helical structure. J Am Chem Soc. Mar. 12, 2003;125(10):2923-9.
Co-pending U.S. Appl. No. 13/494,846, filed Jun. 12, 2012.
Co-pending U.S. Appl. No. 13/655,442, filed Oct. 18, 2010.
Danial, et al. Cell death: critical control points. Cell. 2004; 116:204-219.
Definition of Analog from http://cancerweb.ncl.ac.uk/cgi-bin/omd?query=analog. pp. 1-5. Accessed Jul. 7, 2005.
Degterev et al., "Identification of Small-molecule Inhibitors of Interaction between the BH3 Domain and Bcl-xL," Nature Cell Biol. 3:173-182 (2001).
Deng, et al. Cross-Coupling Reaction of Iodo-1,2,3-triazoles Catalyzed by Palladium. Synthesis 2005(16): 2730-2738.
Designing Custom Peptide. from SIGMA Genosys, pp. 1-2. Accessed Dec. 16, 2004.
Dimartino et al. Solid-phase synthesis of hydrogen-bond surrogate-derived alpha-helices. Org Lett. Jun. 9, 2005;7(12):2389-92.
Erlanson, et al. Facile synthesis of cyclic peptides containing di-, tri-, tetra-, and Pentasulfides. Tetrahedron Letters. 1998; 39(38):6799-6802.
Felix et al., "Synthesis, Biological Activity and Conformational Analysis of Cyclic GRF Analogs," Int. J. Pep. Protein Res. 32:441-454 (1988).
Feng et al. Solid-phase SN2 macrocyclization reactions to form beta-turn mimics. Org Lett. Jul. 15, 1999;1(1):121-4.
Fields, et al. Chapter 3 in Synthetic Peptides: A User's Guide. Grant W.H. Freeman & Co. New York, NY. 1992. p. 77.
Fieser, et al. Fieser and Fieser's Reagents for Organic Synthesis. John Wiley and Sons. 1994.
Fischer, et al. Apoptosis-based therapies and drug targets. Cell Death and Differentiation. 2005; 12:942-961.
Fulda, et al. Extrinsic versus intrinsic apoptosis pathways in anti-cancer chemotherapy. Oncogene. Aug. 7, 2006;25(34):4798-811.
Galande, et al. Thioether side chain cyclization for helical peptide formation: inhibitors of estrogen receptor-coactivator interactions. Journal of Peptide Research. 2004; 63(3): 297-302.
Galande, et al. An effective method of on-resin disulfide bond formation in peptides. J Comb Chem. Mar.-Apr. 2005;7(2):174-7.
Galluzzi, et al. Guidelines for the use and interpretation of assays for monitoring cell death in higher eukaryotes. Cell Death Differ. Aug. 2009;16(8):1093-107. Epub Apr. 17, 2009.

(56) References Cited

OTHER PUBLICATIONS

Ghadiri & Choi, "Secondary Structure Nucleation in Peptides. Transition Metal Ion Stabilized α-Helices," J. Am. Chem. Soc. 112:1630-1632 (1990).
Goncalves, et al. On-resin cyclization of peptide ligands of the Vascular Endothelial Growth Factor Receptor 1 by copper(I)-catalyzed 1,3-dipolar azide-alkyne cycloaddition. Bioorg Med Chem Lett. Oct. 15, 2007;17(20):5590-4.
Greene, et al. Protective Groups in Organic Synthesis, 2nd Ed. John Wiley and Sons. 1991.
Greenlee et al., A General Synthesis of a-vinyl-a-amino acids. Tetrahedron Letters. 1978;42:3999-40002.
Grubbs, et al. Ring-Closing Metathesis and Related Processes in Organic Synthesis. Acc. Chem. Res., 1995, 28 (11), pp. 446-452.
Hanessian, et al. Structure-based design and synthesis of macroheterocyclic peptidomimetic inhibitors of the aspartic protease beta-site amyloid precursor protein cleaving enzyme (BACE). J Med Chem. Jul. 27, 2006;49(15):4544-67.
Hara, S. et al. 'Synthetic studies on halopeptins, anti-inflammatory cyclodepsipeptides', Peptide Science. 2006 (vol. date 2005), 42nd, pp. 39-42.
Hase; et al., "1,6-Aminosuberic acid analogs of lysine- and arginine-vasopressin and -vasotocin. Synthesis and biological properties. J Am Chem Soc. May 17, 1972;94(10):3590-600."
Hein, et al. Copper(I)-Catalyzed Cycloaddition of Organic Azides and 1-Iodoalkynes. Angew Chem Int Ed Engl. 2009;48(43):8018-21.
Hiroshige, et al. Palladium-mediated macrocyclisations on solid support and its applica-tions to combinatorial synthesis. J. Am. Chem. Soc. 1995; 117:11590-11591.
Horne, et al. Heterocyclic peptide backbone modifications in an alpha-helical coiled coil. J Am Chem Soc. Dec. 1, 2004;126(47):15366-7.
Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).
Hu, et al. Efficient p53 activation and apoptosis by simultaneous disruption of binding to MDM2 and MDMX. Cancer Res. Sep. 15, 2007;67(18):8810-7.
International search report and written opinion dated Mar. 3, 2014 for PCT/US2013/068147.
International search report and written opinion dated May 23, 2013 for PCT/US2013/026241.
International search report and written opinion dated May 29, 2013 for PCT/US2013/026238.
International search report and written opinion dated Oct. 12, 2011 for PCT/US2011/047692.
International search report dated Nov. 30, 2009 for PCT Application No. US2009/02225.
International search report dated Apr. 28, 2008 for PCT Application No. US2007/87615.
International search report dated May 18, 2005 for PCT Application No. US2004/38403.
International Search Report dated Sep. 10, 2014 for PCT Application No. US2014/025544.
International search report dated Sep. 25, 2008 for PCT Application No. US2008/54922.
Isidro-Llobet, et al. Amino acid-protecting groups. Chem Rev. Jun. 2009;109(6):2455-504. doi: 10.1021/cr800323s.
Jackson et al. General approach to the synthesis of short alpha-helical peptides. JACS. 1991;113:9391-9392.
Ji, et al. In vivo activation of the p53 tumor suppressor pathway by an engineered cyclotide. J Am Chem Soc. Aug. 7, 2013;135(31):11623-33. doi: 10.1021/ja405108p. Epub Jul. 25, 2013.
Jin, et al. Structure-based design, synthesis, and activity of peptide inhibitors of RGS4 GAP activity. Methods Enzymol. 2004;389:266-77.
Jin, et al. Structure-based design, synthesis, and pharmacologic evaluation of peptide RGS4 inhibitors. J Pept Res. Feb. 2004;63(2):141-6.
Johannesson, et al. Vinyl sulfide cyclized analogues of angiotensin II with high affinity and full agonist activity at the AT(1) receptor. J Med Chem. Apr. 25, 2002;45(9):1767-77.
Kallen, et al. Crystal structures of human MdmX(HdmX) in complex with p53 peptide analogues reveal surprising conformational changes. Journal of Biological Chemistry. Mar. 27, 2009; 284:8812-8821.
Kanan et al. Reaction discovery enabled by DNA-templated synthesis and in vitro selection. Nature. Sep. 30, 2004;431(7008):545-9.
Karle, et al. Structural charateristics of alpha-helical peptide molecules containing Aib residues. Biochemistry. Jul. 24, 1990;29(29):6747-56.
Karle. Flexibility in peptide molecules and restraints imposed by hydrogen bonds, the Aib residue, and core inserts. Biopolymers. 1996;40(1):157-80.
Kedrowski, B.L. et al. 'Thiazoline ring formation from 2-methylcysteines and 2-halomethylalanines', Heterocycles. 2002, vol. 58, pp. 601-634.
Kelso et al., "A Cyclic Metallopeptide Induces α Helicity in Short Peptide Fragments of Thermolysin," Angew. Chem. Int. Ed. 42(4):421-424 (2003).
Kelso et al., "α-Turn Mimetics: Short Peptide α-Helices Composed of Cyclic Metallopentapeptide Modules," J. Am. Chem. Soc. 126:4828-4842 (2004).
Kemp et al., "Studies of N-Terminal Templates for α-Helix Formation. Synthesis and Conformational Analysis of (2S,5S,8S,11S)-1-Acetyl-1,4-diaza-3-keto-5-carboxy-10- thiatricyclo[2.8.1.04,8]-tridecane (Ac-Hel1-OH)," J. Org. Chem. 56:6672-6682 (1991).
Kent. Advanced Biology. Oxford University Press. 2000.
Kilby et al., "Potent Suppression of HIV-1 Replication in Humans by T-20, a Peptide Inhibitor of gp41-Mediated Virus Entry," Nat. Med. 4(11):1302-1307 (1998).
Kinzler et al., Lessons from hereditary colorectal cancer. Cell. Oct. 18, 1996;87(2):159-70.
Kritzer et al., "Helical β-Peptide Inhibitors of the p53-hDM2 Interaction," J. Am. Chem. Soc. 126:9468-9469 (2004).
Kudaj, et al. An efficient synthesis of optically pure alpha-alkyl-beta-azido- and alpha-alkyl-beta-aminoalanines via ring opening of 3-amino-3-alkyl-2-oxetanones. Tetrahedron Letters. 2007; 48:6794-6797.
Kutzki et al., "Development of a Potent Bcl-xL Antagonist Based on α-Helix Mimicry," J. Am. Chem. Soc. 124:11838-11839 (2002).
Kwon, et al. Quantitative comparison of the relative cell permeability of cyclic and linear peptides. Chem Biol. Jun. 2007;14(6):671-7.
Larock, R.C. Comprehensive Organic Transformations, New York: VCH Publishers; 1989.
Leduc et al., Helix-stabilized cyclic peptides as selective inhibitors of steroid receptor-coactivator interactions. Proc Natl Acad Sci USA. 2003;100(20):11273-78.
Lee, et al. A novel BH3 ligand that selectively targets Mcl-1 reveals that apoptosis can proceed without Mcl-1 degradation. J Cell Biol. Jan. 28, 2008;180(2):341-355.
Li, et al. A convenient preparation of 5-iodo-1,4-disubstituted-1,2,3-triazole: multicomponent one-pot reaction of azide and alkyne mediated by CuI-NBS. J Org Chem. May 2, 2008;73(9):3630-3. doi: 10.1021/jo800035v. Epub Mar. 22, 2008.
Li; et al., "A versatile platform to analyze low-affinity and transient protein-protein interactions in living cells in real time.", 2014, 9(5):, 1946-58.
Li, et al. Structure-based design of thioether-bridged cyclic phosphopeptides binding to Grb2-SH2 domain. Bioorg Med Chem Lett. Mar. 10, 2003;13(5):895-9.
Li, et al. Systematic mutational analysis of peptide inhibition of the p53-MDM2/MDMX interactions. J Mol Biol. Apr. 30, 2010;398(2):200-13. doi: 10.1016/j.jmb.2010.03.005. Epub Mar. 10, 2010.
Litowski & Hodges, "Designing Heterodimeric Two-stranded α-Helical Coiled-coils: Effects of Hydrophobicity and α-Helical

(56) References Cited

OTHER PUBLICATIONS

Propensity on Protein Folding, Stability, and Specificity," J. Biol. Chem. 277(40):37272-37279 (2002).
Lu, et al. Proteomimetic libraries: design, synthesis, and evaluation of p53-MDM2 interaction inhibitors. J Comb Chem. May-Jun. 2006;8(3):315-25.
Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.
Luo, et al. Wnt signaling and hunian diseases: what are the therapeutic implications? Lab Invest. Feb. 2007;87(2):97-103. Epub Jan. 8, 2007.
Lyu, et al. Capping Interactions in Isolated α Helices: Position-dependent Substitution Effects and Structure of a Serine-capped Peptide Helix. Biochemistry. 1993; 32:421-425.
Lyu et al, "α-Helix Stabilization by Natural and Unnatural Amino Acids with Alkyl Side Chains," Proc. Nat'l Acad. Sci. USA 88:5317-5320 (1991).
Mai, et al. A proapoptotic peptide for the treatment of solid tumors. Cancer Research. 2001; 61:7709-7712.
Mangold, et al. Azidoalanine mutagenicity in *Salmonella*: effect of homologation and alpha-Mutat Res. Feb. 1989;216(1):27-33.methyl substitution.
Mannhold, R., Kubinyi, H., Folkers, G., series eds. Molecular Drug Properties: Measurement and Prediction (Methods and Principles in Medicinal Chemistry). Wiley-VCH; 2007.
Martin, et al. Thermal [2+2] intramolecular cycloadditions of fuller-1,6-enynes. Angew Chem Int Ed Engl. Feb. 20, 2006;45(9):1439-42.
McGahon, et al. The end of the (cell) line: methods for the study of apoptosis in vitro. Methods Cell Biol. 1995;46:153-85.
Moellering et al., Abstract 69. Computational modeling and molecular optimization of stabilized alpha-helical peptides targeting NOTCH-CSL transcriptional complexes. Nov. 2010; 8(7):30. DOI: 10.1016/S1359-6349(10)71774-2. Abstract Only, European Journal of Cancer Supplements, 2010, 8(7).
Mosberg, et al. Dithioeter-containing cyclic peptides. J. Am. Chem. Soc. 1985;107(10):2986-2987.
Muchmore, et al. X-ray and NMR structure of human Bcl-xL, an inhibitor of programmed cell death. Nature. May 23, 1996;381(6580):335-41.
Mulqueen et al. Synthesis of the thiazoline-based siderophore (S)-desferrithiocin. 1993;48(24):5359-5364.
Mustapa, et al. Synthesis of a Cyclic Peptide Containing Norlanthionine: Effect of the Thioether Bridge on Peptide Conformation. J. Org. Chem. 2003;68(21):8193-8198.
Nelson & Kallenbach, "Persistence of the α-Helix Stop Signal in the S-Peptide in Trifluoroethanol Solutions," Biochemistry 28:5256-5261 (1989).
Ngo et al. Computational complexity, protein structure prediction and the Levinthal Paradox.In: The Protein Folding Problem and Tertiary Structure Prediction. K.Merz, Jr. and S. LeGrand, eds., 1994, pp. 491-495.
Notice of allowance dated Jan. 7, 2015 for U.S. Appl. No. 13/370,057.
Notice of allowance dated Jan. 27, 2014 for U.S. Appl. No. 12/233,555.
Notice of allowance dated Mar. 22, 2010 for U.S. Appl. No. 11/148,976.
Notice of allowance dated May 4, 2004 for U.S. Appl. No. 09/574,086.
Notice of allowance dated May 8, 2012 for U.S. Appl. No. 12/182,673.
Notice of allowance dated Jun. 12, 2014 for U.S. Appl. No. 12/525,123.
Notice of allowance dated Jul. 7, 2009 for U.S. Appl. No. 10/981,873.
Notice of allowance dated Jul. 28, 2014 for U.S. Appl. No. 13/680,905.
Notice of allowance dated Aug. 1, 2014 for U.S. Appl. No. 13/767,852.
Notice of allowance dated Aug. 6, 2012 for U.S. Appl. No. 12/796,212.
Notice of allowance dated Nov. 6, 2014 for U.S. Appl. No. 13/767,857.
Office action dated Jan. 3, 2013 for U.S. Appl. No. 12/593,384.
Office action dated Jan. 13, 2014 for U.S. Appl. No. 13/767,857.
Office action dated Jan. 17, 2014 for U.S. Appl. No. 13/816,880.
Office action dated Jan. 26, 2009 for U.S. Appl. No. 11/148,976.
Office Action dated Jan. 30, 2008 for U.S. Appl. No. 10/981,873.
Office action dated Feb. 4, 2014 for U.S. Appl. No. 13/370,057.
Office action dated Feb. 6, 2014 for U.S. Appl. No. 13/680,905.
Office action dated Feb. 9, 2012 for U.S. Appl. No. 12/420,816.
Office action dated Feb. 17, 2011 for U.S. Appl. No. 12/796,212.
Office action dated Feb. 24, 2015 for U.S. Appl. No. 13/252,751.
Office action dated Mar. 18, 2013 for U.S. Appl. No. 13/097,930.
Office action dated Mar. 18, 2015 for U.S. Appl. No. 14/070,367.
Office action dated Mar. 22, 2013 for U.S. Appl. No. 12/233,555.
Office action dated Mar. 26, 2015 for U.S. Appl. No. 14/070,354.
Office Action dated Mar. 28, 2016 for U.S. Appl. No. 14/070,306.
Office action dated Apr. 9, 2014 for U.S. Appl. No. 13/767,852.
Office action dated Apr. 10, 2015 for U.S. Appl. No. 14/460,848.
Office action dated Apr. 18, 2011 for U.S. Appl. No. 12/182,673.
Office action dated Apr. 26, 2012 for U.S. Appl. No. 13/097,930.
Office action dated May 10, 2010 for U.S. Appl. No. 11/957,325.
Office action dated May 19, 2010 for U.S. Appl. No. 12/140,241.
Office Action dated Jun. 4, 2015 for U.S. Appl. No. 14/070,306.
Office action dated Jun. 28, 2012 for U.S. Appl. No. 12/233,555.
Office action dated Jun. 28, 2013 for U.S. Appl. No. 13/370,057.
Office action dated Jul. 15, 2013 for U.S. Appl. No. 13/570,146.
Office action dated Jul. 16, 2014 for U.S. Appl. No. 13/767,857.
Office action dated Jul. 21, 2014 for U.S. Appl. No. 13/370,057.
Office action dated Jul. 30, 2013 for U.S. Appl. No. 13/097,930.
Office action dated Aug. 9, 2010 for U.S. Appl. No. 12/182,673.
Office action dated Aug. 10, 2009 for U.S. Appl. No. 11/957,325.
Office action dated Aug. 11, 2009 for U.S. Appl. No. 12/140,241.
Office action dated Aug. 19, 2010 for U.S. Appl. No. 12/037,041.
Office action dated Sep. 18, 2013 for U.S. Appl. No. 13/767,857.
Office action dated Sep. 23, 2013 for U.S. Appl. No. 13/680,905.
Office action dated Oct. 10, 2013 for U.S. Appl. No. 13/816,880.
Office action dated Oct. 15, 2012 for U.S. Appl. No. 13/097,930.
Office action dated Oct. 18, 2011 for U.S. Appl. No. 12/796,212.
Office action dated Oct. 31, 2014 for U.S. Appl. No. 13/370,057.
Office action dated Nov. 5, 2002 for U.S. Appl. No. 09/574,086.
Office action dated Nov. 25, 2009 for U.S. Appl. No. 11/148,976.
Office action dated Dec. 5, 2008 for U.S. Appl. No. 10/981,873.
Office action dated Dec. 13, 2012 for U.S. Appl. No. 12/690,076.
Office action dated Dec. 19, 2014 for U.S. Appl. No. 14/068,844.
Office action dated Dec. 29, 2011 for U.S. Appl. No. 12/233,555.
Office action dated Dec. 31, 2013 for U.S. Appl. No. 12/525,123.
O'Neil & DeGrado, "A Thermodynamic Scale for the Helix-forming Tendencies of the Commonly Occurring Amino Acids," Science 250:646-651(1990).
Or et al. Cysteine alkylation in unprotected peptides: synthesis of a carbavasopressin analogue by intramolecular cystein alkylation. J. Org. Chem. Apr. 1991;56(9):3146-3149.
Paquette, L.A., ed. Encyclopedia of Reagents for Organic Synthesis. New York; John Wiley & Sons; 1995.
Pattenden, et al. Enantioselective synthesis of 2-alkyl substituted cysteines. 1993;49(10):2131-2138.
Pattenden, et al. Naturally occurring linear fused thiazoline-thiazole containing metabolites: total synthesis of (−)-didehydromirabazole A, a cytotoxic alkaloid from blue-green algae. J Chem Soc. 1993;14:1629-1636.
Pazgier, et al. Structural basis for high-affinity peptide inhibition of p53 interactions with MDM2 and MDMX. Proc Natl Acad Sci U S A. Mar. 24, 2009;106(12):4665-70. doi: 10.1073/pnas.0900947106. Epub Mar. 2, 2009.
Perantoni, Renal development: perspectives on a Wnt-dependent process. Semin Cell Dev Biol. Aug. 2003;14(4):201-8.

(56) References Cited

OTHER PUBLICATIONS

Peryshkov, et al. Z-Selective olefin metathesis reactions promoted by tungsten oxo alkylidene complexes. Am Chem Soc. Dec. 28, 2011;133(51):20754-7. doi: 10.1021/ja210349m. Epub Nov. 30, 2011.
Phan, et al. Structure-based design of high affinity peptides inhibiting the interaction of p53 with MDM2 and MDMX. J Biol Chem. Jan. 15, 2010;285(3):2174-83. doi: 10.1074/jbc.M109.073056. Epub Nov. 12, 2009.
Phelan, et al. A General Method for Constraining Short Peptides to an α-Helical Conformation. J. Am. Chem. Soc. 1997;119:455-460.
Qiu et al., Convenient, Large-Scale Asymmetric Synthesis of Enantiomerically Pure trans-Cinnamylglycine and -a-Alanine. Tetrahedron. 2000;56:2577-82.
Rink, et al. Lantibiotic Structures as Guidelines for the Design of Peptides That Can Be Modified by Lantibiotic Enzymes. Biochemistry. 2005; 44:8873-8882.
Roberts, et al. Efficient synthesis of thioether-based cyclic peptide libraries. Tetrahedon Letters. 1998; 39: 8357-8360.
Roberts, et al. Examination of methodology for the synthesis of cyclic thioether peptide libraries derived from linear tripeptides. J Pept Sci. Dec. 2007;13(12):811-21.
Roice, et al. High Capacity Poly(ethylene glycol) Based Amino Polymers for Peptide and Organic Synthesis. QSAR & Combinatorial Science. 2004;23(8):662-673.
Rojo, et al. Macrocyclic peptidomimetic inhibitors of R-secretase (BACE): First X-ray structure of a macrocyclic peptidomimetic-BACE complex. Bioorg. Med. Chem. Lett. 2006; 16:191-195.
Roof, et al. Mechanism of action and structural requirements of constrained peptide inhibitors of RGS proteins. Chem Biol Drug Des. Apr. 2006;67(4):266-74.
Ruan et al., "Metal Ion Enhanced Helicity in Synthetic Peptides Containing Unnatural, Metal-ligating Residues," J. Am. Chem. Soc. 112:9403-9404 (1990).
Rudinger J, "Characteristics of the amino acids as components of a peptide hormone sequence," Peptide Hormones, JA Parsons Edition, University Park Press, Jun. 1976, pp. 1-7.
Ruffolo and Shore. BCL-2 Selectively Interacts with the BID-Induced Open Conformer of BAK, Inhibiting BAK Auto-Oligomerization. J. Biol. Chem. 2003;278(27):25039-25045.
Saghiyan, A. S., et al., "New chiral Niii complexes of Schiffs bases of glycine and alanine for efficient asymmetric synthesis of a-amino acids," Tedrahedron: Asymmetry 17: 455-467 (2006).
Saghiyan, et al. Novel modified (S)-N-(benzoylphenyl)-1-(3,4-dichlorobenzyl)-pyrrolidine-2-carboxamide derived chiral auxiliarie for asymmetric synthesis of (S)-alpha-amino acids. Chemical Journal of Armenia. Aug. 2002; 55(3):150-161. (abstract only).
Sanchez-Garcia, et al. Tumorigenic activity of the BCR-ABL oncogenes is mediated by BCL2. Proc Natl Acad Sci U S A. Jun. 6, 1995;92(12):5287-91.
Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).
Sattler et al. Structure of Bcl-xL-Back peptide complex: recognition between regulators of apoptosis. Science. 1997;275:983-986.
Schafmeister et al. An all-hydrocarbon crosslinking system for enhancing the helicity and metabolic stability of peptides. J. Am Chem. Soc. 2000;122:5891-5892.
Schinzel et al., The phosphate recognition site of *Escherichia coli* maltodextrin phosphorylase. FEBS Lett. Jul. 29, 1991;286(1-2):125-8.
Scorrano, et al. A distinct pathway remodels mitochondrial cristae and mobilizes cytochrome c during apoptosis. Dev Cell. Jan. 2002;2(1):55-67.
Scott, et al. A Solid-Phase Synthetic Route to Unnatural Amino Acids with Diverse Side-Chain Substitutions. Journal of Organic Chemistry. 2002, vol. 67, No. 9, pp. 2960-2969.
Seebeck, et al. Ribosomal synthesis of dehydroalanine-containing peptides. J Am Chem Soc. Jun. 7, 2006;128(22):7150-1.

Shepherd et al., "Single Turn Peptide Alpha Helices with Exceptional Stability in Water," J. Am. Chem. Soc. 127:2974-2983 (2005).
Shi, et al. The role of arsenic-thiol interactions in metalloregulation of the ars operant. J Biol Chem. Apr. 19, 1996;271(16):9291-7.
Sia et al., "Short Constrained Peptides that Inhibit HIV-1 Entry," Proc. Nat'l Acad. Sci. USA 99(23):14664-14669 (2002).
Singh, et al. Efficient asymmetric synthesis of (S)- and (R)-N-Fmoc-S-trityl-alpha-methylcysteine using camphorsultam as a chiral auxiliary.. J Org Chem. Jun. 25, 2004;69(13):4551-4.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S39.
Solution phase synthesis from http://www.combichemistry.com/solution_phase_synthesis.html. p. 1. Accessed Aug. 6, 2009.
Spierings, et al. Connected to death: the (unexpurgated) mitochondrial pathway of apoptosis. Science. 2005; 310:66-67.
Stewart, et al. Cell-penetrating peptides as delivery vehicles for biology and medicine. Org Biomol Chem. Jul. 7, 2008;6(13):2242-55. doi: 10.1039/b719950c. Epub Apr. 15, 2008.
STN search notes for Lu reference, 4 pages, 2006.
Suzuki, et al. Structure of Bax: coregulation of dimer formation and intracellular localization. Cell. Nov. 10, 2000;103(4):645-54.
Szewczuk, et al. Synthesis and Biological activity of new conformationally restricted analogues of pepstatin. Int. J. Peptide Protein. Res. 1992; 40:233-242.
Tam, et al. Protein prosthesis: 1,5-disubstituted[1,2,3]triazoles as cis-peptide bond surrogates. J Am Chem Soc. Oct. 24, 2007;129(42):12670-1.
Tanaka, Design and synthesis of non-proteinogenic amino acids and secondary structures of their peptides. Yakugaku Zasshi. Oct. 2006:126(10):931-44. Japanese.
Taylor. The synthesis and study of side-chain lactam-bridged peptides. Biopolymers. 2002;66(1):49-75.
Titus, et al. Human K/natural killer cells targeted with hetero-cross-linked antibodies specifically lyse tumor cells in vitro and prevent tumor growth in vivo. J Immunol. Nov. 1, 1987;139(9):3153-8.
Torres, et al. Peptide tertiary structure nucleation by side-chain crosslinking with metal complexation and double "click" cycloaddition. Chembiochem. Jul. 21, 2008;9(11):1701-5.
Trnka & Grubbs, "The Development of L2X2Ru=CHR Olefin Metathesis Catalysts: An Organometallic Success Story," Acc. Chem. Res. 34:18-29 (2001).
Tugyi, et al. The effect of cyclization on the enzymatic degradation of herpes simplex virus glycoprotein D derived epitope peptide. J Pept Sci. Oct. 2005;11(10):642-9.
Tyndall et al. Macrocycles mimic the extended peptide conformation recognized by aspartic, serine, cysteine and metallo proteases. Curr Med Chem. Jul. 2001;8(8):893-907.
Ueki, et al. Improved synthesis of proline-derived Ni(II) complexes of glycine: versatile chiral equivalents of nucleophilic glycine for general asymmetric synthesis of alpha-amino acids. J Org Chem. Sep. 5, 2003;68(18):7104-7.
U.S. Appl. No. 61/385,405, filed Sep. 22, 2010.
Van Maarseveen, et al. Efficient route to C2 symmetric heterocyclic backbone modified cyclic peptides. Org Lett. Sep. 29, 2005;7(20):4503-6.
Viallet, et al. Tallimustine is inactive in patients with previously treated small cell lung cancer. A phase II trial of the National Cancer Institute of Canada Clinical Trials Group. Lung Cancer. Nov. 1996;15(3):367-73.
Voet D, Voet JG, Biochemistry, Second Edition, John Wiley & Sons, Inc., 1995, pp. 235-241.
Walensky, et al. Activation of apoptosis in vivo by a hydrocarbon-stapled BH3 helix. Science. Sep. 3, 2004;305(5689):1466-70.
Walker, et al. General method for the synthesis of cyclic peptidomimetic compounds. Tetrahedron Letters. 2001; 42(34):5801-5804.
Wang et al. Cell permeable Bcl-2 binding peptides: a chemical approach to apoptosis induction in tumor cells. Cancer Res. Mar. 15, 2000;60(6):1498-502.

(56) References Cited

OTHER PUBLICATIONS

Wang, et al. "Click" synthesis of small molecule probes for activity-based fingerprinting of matrix metalloproteases. Chem Commun (Camb). Sep. 28, 2006;(36):3783-5.
Wang et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.
Wang, et al. Evaluation of biologically relevant short alpha-helices stabilized by a main-chain hydrogen-bond surrogate. J Am Chem Soc. Jul. 19, 2006;128(28):9248-56.
Wang, et al. Nucleation and stability of hydrogen-bond surrogate-based alpha-helices. Org Biomol Chem. Nov. 21, 2006;4(22):4074-81.
Wei, et al. tBID, a membrane-targeted death ligand, oligomerizes BAK to release cytochrome c. Genes Dev. Aug. 15, 2000;14(16):2060-71.
Wels, et al. Synthesis of a novel potent cyclic peptide MC4-ligand by ring-closing metathesis. Bioorg. Med. Chem. Lett. 2005; 13: 4221-4227.
Wild et al., "Peptides Corresponding to a Predictive α-Helical Domain of Human Immunodeficiency Virus Type 1 gp4I are Potent Inhibitors of Virus Infection," Proc. Nat'l Acad. Sci. USA 91:9770-9774 (1994).
Wilen, Tables of Resolving Agents and Optical Resolutions. E.L. Eliel, ed. Universtify of Notre Dame Press, Notre Dame, IN. 1972:268-98.
Williams and Im. Asymmetric Synthesis of Nonsubstituted and α,α-Disubstituted α-Amino Acids via Disatereoselective Glycine Enolate Alkylations. JACS. 1991;113:9276-9286.
Wu, et al. Regiospecific Synthesis of 1,4,5-Trisubstituted-1,2,3-triazole via One-Pot Reaction Promoted by Copper(I) Salt. Synthesis. 2005(8): 1314-1318.
Wu, et al. Studies on New Strategies for the Synthesis of Oligomeric 1,2,3-Triazoles. Synlett 2006(4): 0645-0647.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. 310 Helix versus alpha-helix: a molecular dynamics study of conformational preferences of Aib and Alanine. J. American Cancer Society. Dec. 1994; 116(26):11915-11921.
Abbas, et al. (2010). Mdm2 is required for survival of hematopoietic stem cells/progenitors via dampening of ROS-induced p53 activity. Cell Stem Cell 7, 606-617.
Abraham, et al. (2016). Dual targeting of p53 and c-MYC selectively eliminates leukemia stem cells. Nature 534, 341-346.
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4): 305-318.
Ahn, et al. A convenient method for the efficient removal of ruthenium byproducts generated during olefin metathesis reactions. Organic Letters. 2001; 3(9):1411-1413.
Akala, et al. (2008). Long-term haematopoietic reconstitution by Trp53-/-p16Ink4a-/-p19Arf-/-multipotent progenitors. Nature 453, 228-232.
Al-Lazikani, et al. Combinatorial drug therapy for cancer in the post-genomic era. Nature biotechnology 30.7 (2012): 679-692.
Aman et al., cDNA cloning and characterization of the human interleukin 13 receptor alpha chain. J Biol Chem. Nov. 15, 1996;271(46):29265-70.
Andreeff, et al. (2016). Results of the Phase I Trial of RG7112, a Small-Molecule MDM2 Antagonist in Leukemia. Clin Cancer Res 22, 868-876.
Andrews et al., Kinetic analysis of the interleukin-13 receptor complex. J Biol Chem. Nov. 29, 2002;277(48):46073-8. Epub Sep. 26, 2002.
Angel & Karin, "The Role of Jun, Fos and the AP-1 Complex in Cell-proliferation and Transformation," Biochim. Biophys. Acta 1072:129-157 (1991).
Annis, et al. A general technique to rank protein-ligand binding affinities and determine allosteric versus direct binding site competition in compound mixtures. J Am Chem Soc. Dec. 1, 2004;126(47):15495-503.
Annis, et al. ALIS: An affinity selection-mass spectrometry system for the discovery and characterization of protein-ligand Interactions. Mass Spectrometry in Medicinal Chemistry: Applications in Drug Discovery (2007): 121-156.
Arora, "Design, Synthesis, and Properties of the Hydrogen Bond Surrogate-based Artificial Alpha-helices," American Chemical Society Meeting, San Diego (Mar. 2005) (oral).
Arora, "Hydrogen Bond Surrogate Approach for the Synthesis of Short α-Helical Peptides," American Chemical Society Meeting, Philadelphia (Aug. 2004) (abstract of oral presentation).
Artavanis-Tsakonas et al., Notch signaling: cell fate control and signal integration in development. Science. Apr. 30, 1999;284(5415):770-6.
Asai, et al. (2012). Necdin, a p53 target gene, regulates the quiescence and response to genotoxic stress of hematopoietic stem/progenitor cells. Blood 120, 1601-1612.
Attisano et al., TGFbeta and Wnt pathway cross-talk. Cancer Metastasis Rev. Jan.-Jun. 2004;23(1-2):53-61.
Avantaggiati, M.L. Molecular horizons of cancer therapeutics: 11th Pezcoller symposium. Biochim Biophys Acta. May 17, 2000;1470(3):R49-59.
Babcock, Proteins, radicals, isotopes, and mutants in photosynthetic oxygen evolution. Proc Natl Acad Sci U S A. Dec. 1, 1993;90(23):10893-5.
Babine et aL, Molecular Recognition of Proteinminus signLigand Complexes: Applications to Drug Design. Chem Rev. Aug. 5, 1997;97(5):1359-1472.
Badyal, et al. A Simple Method for the Quantitative Analysis of Resin Bound Thiol Groups. Tetrahedron Lett. 2001; 42:8531-33.
Balof, et al. Olefin metathesis catalysts bearing a pH-responsive NHC ligand: a feasible approach to catalyst separation from RCM products. Dalton Trans. Nov. 14, 2008;(42):5791-9. doi: 10.1039/b809793c. Epub Sep. 12, 2008.
Balthaser et al., Remodelling of the natural product fumagillol employing a reaction discovery approach. Nat Chem. Dec. 2011;3(12):969-73.
Banerjee et aL, Structure of a DNA glycosylase searching for lesions. Science. Feb. 24, 2006;311(5764):1153-7.
Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.
Bansal, et al. Salt selection in drug development. Pharmaceutical Technology. Mar. 2, 2008;3(32).
Barker et al., Mining the Wnt pathway for cancer therapeutics. Nat Rev Drug Discov. Dec. 2006;5(12):997-1014.
Barreyro, et al. (2012). Overexpression of IL-1 receptor accessory protein in stem and progenitor cells and outcome correlation in AML and MDS. Blood 120, 1290-1298.
Belokon, et al. Improved procedures for the synthesis of (S)-2-[N-(N'-benzylprolyl)amino]benzophenone (BPB) and Ni(II) complexes of Schiffs bases derived from BPB and amino acids. Tetrahedron: Asymmetry, vol. 9, Issue 23, Dec. 11, 1998, pp. 4249-4252.
Bennett, et al. Regulation of osteoblastogenesis and bone mass by Wnt1 Ob. Proc Natl Acad Sci U S A. Mar. 1, 2005;102(9):3324-9.. Epub Feb. 22, 2005.
Berezowska; et al., "Cyclic dermorphin tetrapeptide analogues obtained via ring-closing metathesis. Acta Biochim Pol. 2006;53(1):73-6. Epub Feb. 23, 2006."
Berge et al. Pharmaceutical Salts. Journal of Pharmaceutical Sciences 66(1):1-19 (Jan. 1977).
Bernal, et al. (2010). A stapled p53 helix overcomes HDMX-mediated suppression of p53. Cancer Cell 18, 411-422.
Bernal et al., Reactivation of the p53 tumor suppressor pathway by a stapled p53 peptide. (2007) J. Am Chem Soc. 9129, 2456-2457.

(56) References Cited

OTHER PUBLICATIONS

Bertrand, et al. (1998). Localization of ASH1 mRNA particles in living yeast. Mol Cell 2, 437-445.
Biagini et al., Cross-metathesis of Unsaturated a-amino Acid Derivatives. J Chem Soc Perkin Trans. 1998;1:2485-99.
Bierzynski et al. A salt bridge stabilizes the helix formed by isolated C-Peptide of RNase A. PNAS USA. 1982;79:2470-2474.
Blackwell, et al. Ring-closing metathesis of olefinic peptides: design, synthesis, and structural characterization of macrocyclic helical peptides. J Org Chem. Aug. 10, 2001;66(16):5291-302.
Blangetti et al., Suzuki-miyaura cross-coupling in acylation reactions, scope and recent developments.Molecules. Jan. 17, 2013;18(1):1188-213. doi:10.3390/molecules18011188.
Blundell et al., Atomic positions in rhombohedral 2-zinc insulin crystals. Nature. Jun. 25, 1971;231(5304):506-11.
Bo, M.D., et al. (2010). MDM4 (MDMX) is overexpressed in chronic lymphocytic leukaemia (CLL) and marks a subset of p53wild-type CLL with a poor cytotoxic response to Nutlin-3. Br J Haematol 150, 237-239.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al. High bone density due to a mutation in LDL-receptor-related protein 5. N Engl J Med 346(20):1513-1521 (2002).
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Bray, Notch signalling: a simple pathway becomes complex. Nat Rev Mol Cell Biol. Sep. 2006;7(9):678-89.
Brea, et al. Synthesis of omega-(hetero)arylalkynylated alpha-amino acid by Sonogashira-type reactions in aqueous media. J Org Chem. Sep. 29, 2006;71(20):7870-3.
Brou et al., A novel proteolytic cleavage involved in Notch signaling: the role of the disintegrin-metalloprotease TACE. Mol Cell. Feb. 2000;5(2):207-16.
Brubaker et al., Solution structure of the interacting domains of the Mad-Sin3 complex: implications for recruitment of a chromatin-modifying complex. Cell. Nov. 10, 2010;103(4):655-65.
Brunel, et al. Synthesis of constrained helical peptides by thioether ligation: application to analogs of gp41. Chemical communications. 2005;20:2552-2554.
Brusselle et al., Allergen-induced airway inflammation and bronchial responsiveness in wild-type and interleukin-4-deficient mice. Am J Respir Cell Mol Biol. Mar. 1995;12(3):254.-9.
Bueso-Ramos, et al. (1993). The human MDM-2 oncogene is overexpressed in leukemias. Blood 82, 2617-2623.
Burfield & Smithers, "Desiccant Efficiency in Solvent Drying. 3. Dipolar Aprotic Solvents," J. Org. Chem. 43(20):3966-3968 (1978).
Burgess, et al. (2016). Clinical Overview of MDM2/X-Targeted Therapies. Front Oncol. 2016; 6: 7.
Cai, et al. Synthesis of new potent agonistic analogs of growth hormone-releasing hormone (GHRH) and evaluation of their endocrine and cardiac activities. Peptides. 2014; 52:104-112.
Campbell, et al. N-alkylated oligoamide alpha-helical proteomimetics. Org Biomol Chem. May 21, 2010;8(10):2344-51. doi: 10.1039/c001164a. Epub Mar. 18, 2010.
Caricasole et al., The Wnt pathway, cell-cycle activation and beta-amyloid: novel therapeutic strategies in Alzheimer's disease? Trends Pharmacol Sci. May 2003;24(5):233-8.
Cariello, et al. Resolution of a missense mutant in human genomic DNA by denaturing gradient gel electrophoresis and direct sequencing using in vitro DNA amplification: HPRT Munich. Am J Hum Genet. May 1988;42(5):726-34.
Carlo-Stella, et al. Use of recombinant human growth hormone (rhGH) plus recombinant human granulocyte colony-stimulating factor (rhG-CSF) for the mobilization and collection of CD34+ cells in poor mobilizers. Blood. May 1, 2004;103(9):3287-95. Epub Jan. 15, 2004.

Carlson et al., Specificity landscapes of DNA binding molecules elucidate biological function. Proc Natl Acad Sci USA. Mar. 9, 2010;107(10):4544-9. doi: 10.1073/pnas.0914023107. Epub Feb. 22, 2010.
Carvajal, et al. (2012). E2F7, a novel target, is up-regulated by p53 and mediates DNA damage-dependent transcriptional repression. Genes Dev 26, 1533-1545.
Cervini, et al. Human growth hormone-releasing hormone hGHRH(1-29)-NH2: systematic structure-activity relationship studies. J Med Chem. Feb. 26, 1998;41(5):717-27.
Chakrabartty et al., "Helix Propensities of the Amino Acids Measured in Alanine-based Peptides without Helix-stabilizing Side-chain Interactions," Protein Sci. 3:843-852 (1994).
Chang, et al. (2013). Stapled alpha-helical peptide drug development: a potent dual inhibitor of MDM2 and MDMX for p53-dependent cancer therapy. Proc Natl Acad Sci U S A 110, E3445-3454.
Chapman, et al. Trapping a folding intermediate of the alpha-helix: stabilization of the pi-helix. Biochemistry. Apr. 8, 2008;47(14):4189-95. doi: 10.1021/bi800136m. Epub Mar. 13, 2008.
Chen et al., Determination of the helix and beta form of proteins in aqueous solution by circular dichroism. Biochemistry. Jul. 30, 1974;13(16):3350-9.
Chen, et al. Determination of the Secondary Structures of Proteins by Circular Dichroism and Optical Rotatory Dispersion. Biochemistry. 1972; 11(22):4120-4131.
Chen et al., Small molecule-mediated disruption of Wnt-dependent signaling in tissue regeneration and cancer. Nat Chem Biol. Feb. 2009;5(2):100-7. Epub Jan. 4, 2009.
Chen et al., "Structure of the DNA-binding Domains from NFAT, Fos and Jun Bound Specifically to DNA," Nature 392:42-48 (1998).
Cheng et al., Emerging role of RAB gtpases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Chittenden, et al. A conserved domain in Bak, distinct from BH1 and BH2, mediates cell death and protein binding functions. EMBO J. Nov. 15, 1995;14(22):5589-96.
Chène et al., "Study of the Cytotoxic Effect of a Peptidic Inhibitor of the p53-hdm2 Interaction in Tumor Cells," FEBS Lett. 529:293-297 (2002).
Chène, P., "Inhibiting the p53-MDM2 Interaction: An Important Target for Cancer Therapy," Nat Rev. Cancer 3:102-109 (2003).
Cho, et al. An efficient method for removal of ruthenium byproducts from olefin metathesis reactions. Org Lett. Feb. 20, 2003;5(4):531-3.
Christodoulides et al., Wntiob mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Clavier, et al. Ring-closing metathesis in biphasic BMI.PF6 ionic liquid/toluene medium: a powerful recyclable and environmentally friendly process. Chem Commun (Camb). Oct. 21, 2004;(20):2282-3. Epub Aug. 25, 2004.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Th1, cells. J Immunol. Oct. 15, 1998;161(8):3813-6.

(56) References Cited

OTHER PUBLICATIONS

Colacino, et al. Evaluation of the anti-influenza virus activities of 1,3,4-thiadiazol-2-ylcyanamide (LY217896) and its sodium salt. Antimicrob Agents Chemother. Nov. 1990;34(11):2156-63.
Colaluca et al., NUMB controls p53 tumour suppressor activity. Nature. Jan. 3, 2008;451(7174):76-80. doi: 10.1038/nature06412.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Conrad, et al. Ruthenium-Catalyzed Ring-Closing Metathesis: Recent Advances, Limitations and Opportunities. Current Organic Chemistry. Jan. 2006; vol. 10, No. 2, 10(2):185-202(18).
Co-pending U.S. Appl. No. 15/229,517, filed Aug. 5, 2016.
Co-pending U.S. Appl. No. 15/233,796, filed Aug. 10, 2016.
Co-pending U.S. Appl. No. 15/256,130, filed Sep. 2, 2016.
Co-pending U.S. Appl. No. 15/257,807, filed Sep. 6, 2016.
Co-pending U.S. Appl. No. 15/259,947, filed Sep. 8, 2016.
Co-pending U.S. Appl. No. 15/332,492, filed Oct. 24, 2016.
Co-pending U.S. Appl. No. 15/349,478, filed Nov. 11, 2016.
Co-pending U.S. Appl. No. 15/463,826, filed Mar. 20, 2017.
Co-pending U.S. Appl. No. 15/493,301, filed Apr. 21, 2017.
Co-pending U.S. Appl. No. 15/592,517, filed May 11, 2017.
Co-pending U.S. Appl. No. 15/625,672, filed Jun. 16, 2017.
Cory et al., "The Bcl-2 Family: Roles in Cell Survival and Oncogenesis," Oncogene 22:8590-8607 (2003).
Cossu et al., Wnt signaling and the activation of myogenesis in mammals EMBO J. Dec. 15, 1999;18(24):6867-72.
Cotton et al. Reactivity of cytosine and thymine in single-base-pair mismatches with hydroxylamine and osmium tetroxide and its application to the study of mutations. PNAS USA 85(12):4397-401 (1988).
Cox et al., Insulin receptor expression by human prostate cancers. Prostate. Jan. 1, 2009;69(1):33-40. doi: 10.1002/pros.20852.
Coy, et al. Structural Simplification of Potent Growth Hormone-Releasing Hormone Analogs: Implications for Other Members of the VIP/GHRW PACAP Family. Annals of the New York Academy of Sciences. VIP, PACAP, Glucagon, and Related Peptides. Dec. 1996; 805:149-158.
Cummings, et al. Disrupting protein-protein interactions with non-peptidic, small molecule alpha-helix mimetics. Curr Opin Chem Biol. Jun. 2010;14(3):341-6. doi: 10.1016/j.cbpa.2010.04.001. Epub Apr. 27, 2010.
Cusack et al. 2,4,6-Tri-isopropylbenzenesulphonyl Hydrazide: A convenient source of Di-Imide. Tetrahedron. 1976;32:2157-2162.
Danial et al., Dual role of proapoptotic BAD in insulin secretion and beta cell survival. Nat Med. Feb. 2008;14(2):144-53. doi: 10.1038/nm1717. Epub Jan. 27, 2008.
Darnell, Transcription factors as targets for cancer therapy. Nat Rev Cancer. Oct. 2002;2(10):740-9.
Daugherty & Gellman, "A Fluorescence Assay for Leucine Zipper Dimerization: Avoiding Unintended Consequences of Fluorophore Attachment," J. Am. Chem. Soc. 121:4325-4333 (1999).
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De La O et al., Notch and Kras reprogram pancreatic acinar cells to ductal intraepithelial neoplasia. Proc Natl Acad Sci USA. Dec. 2, 2008;105(48):1 8907-12. doi: 10.1073/pnas.0810111105. Epub Nov. 21, 2008.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
De Strooper et al., A presenilin-1-dependent gamma-secretase-like protease mediates release of Notch intracellular domain. Nature. Apr. 8, 1999;398(6727):518-22.
Debinski et al., Retargeting interleukin 13 for radioimmunodetection and radioimmunotherapy of human high-grade gliomas. Clin Cancer Res. Oct. 1999;5(10 Suppl):3143s-3147s.
Deiters, et al. Adding amino acids with novel reactivity to the genetic code of *Saccharomyces cerevisiae*. J Am Chem Soc. Oct. 1, 2003;125(39):11782-3.
Del Bianco et al., Mutational and energetic studies of Notch 1 transcription complexes. J Mol Biol. Feb. 8, 2008;376(1):131-40. Epub Nov. 28, 2007.
Denmark et al., Cyclopropanation with Diazomethane and Bis(oxazoline)palladium(II) Complexes. J Org Chem. May 16, 1997;62(10):3375-3389.
Dennis et al. Albumin binding as a general strategy for improving the pharmacokinetics of proteins. J Biol Chem. 277(38):35035-35043 (2002).
Devereux et al., A comprehensive set of sequence analysis programs for the VAX. Nucleic Acids Res. Jan. 11, 1984;12(1 Pt 1):387-95.
Dimartino et al, "A General Approach for the Stabilization of Peptide Secondary Structures," American Chemical Society Meeting, New York (Sep. 2003) (poster).
Dombroski et al., Isolation of an active human transposable element. Science. Dec. 20, 1991;254(5039):1805-8.
Doron, et al. Probiotics: their role in the treatment and prevention of disease. Expert Rev Anti Infect Ther. Apr. 2006;4(2):261-75.
Dovey et al., Functional gamma-secretase inhibitors reduce beta-amyloid peptide levels in brain. J Neurochem. Jan. 2001;76(1):173-81.
Dubreuil, et al. Growth hormone-releasing factor: structural modification or protection for more potent analogs. Comb Chem High Throughput Screen. Mar. 2006;9(3):171-4.
Duronio, Insulin receptor is phosphorylated in response to treatment of HepG2 cells with insulin-like growth factor I. Biochem J. Aug. 15, 1990;270(1):27-32.
Dyson, et al. Applications of ionic liquids in synthesis and catalysis. Interface-Electrochemical Society. 2007; 16(1), 50-53.
Eckert & Kim, "Mechanisms of Viral Membrane Fusion and Its Inhibition," Annu. Rev. Biochem. 70:777-810 (2001).
Edlund, et al. Data-driven unbiased curation of the TP53 tumor suppressor gene mutation database and validation by ultradeep sequencing of human tumors. PNAS Early Edition, pp. 1-20.
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the *Drosophila* notch gene, is broken by chromosomal translocations in T lymphoblastic neoplasms. Cell. Aug. 23, 1991;66(4):649-61.
Ellman. Tissue sulfhydryl groups. Arch Biochem Biophys. May 1959;82(1):70-7.
Erlanson et al., The leucine zipper domain controls the orientation of AP-1 in the NFAT.AP-1.DNA complex. Chem Biol. Dec. 1996;3(12):981-91.
European Medicines Agency, Guideline on the specification limits for residues of metal catalysts or metal regents. Feb. 2008; pp. 1-34.
European Medicines Agency (Pre-authorization Evaluation of Medicines for Human Use, London, Jan. 2007, p. 1-32).
European search report and opinion dated Feb. 9, 2012 for EP Application No. 09815315.8.
Evans et al., The Rise of Azide-Alkyne 1,3-Dipolar 'Click' Cycloaddition and its Application to Polymer Science and Surface Modification. Australian Journal of Chemistry. 2007;60:384-95.

(56) References Cited

OTHER PUBLICATIONS

Extended European Search Report for EP 12800679.8, dated Oct. 2, 2014.
Faderl, et al. (2000). The prognostic significance of p16(INK4a)/p14(ARF) locus deletion and MDM-2 protein expression in adult acute myelogenous leukemia. Cancer 89, 1976-1982.
Favrin et al., Two-state folding over a weak free-energy barrier. Biophys J. Sep. 2003;85(3):1457-65.
Felix et al. Biologically active cyclic (lactam) analogs of growth hormone-releasing factor: Effect of ring size and location on conformation and biological activity. Proceedings of the Twelfth American Peptide Symposium. p. 77-79:1991.
Ferdinandi, et al. Non-clinical pharmacology and safety evaluation of TH9507, a human growth hormone-releasing factor analogue. Basic Clin Pharmacol Toxicol. Jan. 2007;100(1):49-58.
File Hcaplus on STN. AN No. 1986:572318. Armstrong et al. X=Y-ZH systems as potential 1,3-dipoles. 5. Intramolecular imines of α-amino acid esthers. Tetrahedron. 1985; 41(17):3547-58. Abstract only. Abstract date Nov. 1986.
File Hcaplus on STN. AN No. 1990:532752. Burger et al. Synthesis of a-(trifluoromethyl)-substituted a-amino acids. Part 7. An efficient synthesis for a-trifluoromethyl-substituted w-carboxy a-amino acids. Chemiker-Zeitung (1990), 114(3), 101-4. Abstract only, date Oct. 1990.
File Hcaplus on STN. AN No. 1979:168009. Greenlee et al. A general synthesis of alpha- vinyl-alpha-amino acids Tetrahedron Letters (1978), (42), 3999-4002. Abstract date 1984.
Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fischer, P. Peptide, Peptidomimetic, and Small-molecule Antagonists of the p53-HDM2 Protein-Protein Interaction. Int J Pept Res Ther. Mar. 2006;12(1):3-19. Epub Mar. 15, 2006.
Fisher et al., Myc/Max and other helix-loop-helix/leucine zipper proteins bend DNA toward the minor groove. Proc Natl Acad Sci U S A. Dec. 15, 1992;89(24):11779-83.
Folkers, et al. Methods and principles in medicinal chemistry. Eds. R. Mannhold, H. Kubinyi, and H. Timmerman. Wiley-VCH, 2001.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Freedman, et al. Structural basis for recruitment of CBP/p300 by hypoxia-inducible factor-1 alpha. Proc Natl Acad Sci U S A. Apr. 16, 2002;99(8):5367-72.
Friedman-Einat, et al. Target gene identification: target specific transcriptional activation by three murine homeodomain/VP16 hybrid proteins in *Saccharomyces cerevisiae*. J Exp Zool. Feb. 15, 1996;274(3):145-56.
Friedmann et al., RAM-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fry et al. Solution structures of cyclic and dicyclic analogues of growth hormone releasing factor as determined by two-dimensional NMR and CD spectroscopies and constrained molecular dynamics. Biopolymers. Jun. 1992;32(6):649-66.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fung et al., Delta-like 4 induces notch signaling in macrophages: implications for inflammation. Circulation. Jun. 12, 2007;115(23):2948-56. Epub May 28, 2007.

Furstner et al., Alkyne Metathesis: Development of a Novel Molybdenum-Based Catalyst System and Its Application to the Total Synthesis of Epothilone A and C. Chem Euro J. 2001 ;7(24):5299-5317.
Furstner, et al. Mo[N(t-Bu)(AR)]3 Complexes as catalyst precursors: In situ activation and application to metathesis reactions of alkynes and diynes. J Am chem Soc. 1999; 121:9453-54.
Furstner, et al. Nozaki--Hiyama--Kishi reactions catalytic in chromium. J Am Chem Soc. 1996; 118:12349-57.
Fustero, et al. Asymmetric synthesis of new beta,beta-difluorinated cyclic quaternary alpha-amino acid derivatives. Org Lett. Aug. 31, 2006;8(18):4129-32.
Galande, et al. An effective method of on-resin disulfide bond formation in peptides. Journal of combinatorial chemistry. 2005;7(2):174-177.
Gallivan et al., A neutral, water-soluble olefin metathesis catalyst based on an N-heterocyclic carbene ligand. Tetrahedron Letters. 2005;46:2577-80.
Gallou, et al. A practical method for the removal of ruthenium byproducts by supercritical fluid extraction. Organic Process Research and Development. 2006; 10:937-940.
Gante, Peptidomimetics—Tailored Enzyme Inhibitors. J Angew Chem Int Ed Engl. 1994;33:1699-1720.
García-Echeverría et al., "Discovery of Potent Antagonists of the Interaction between Human Double Minute 2 and Tumor Suppressor p53," J. Med. Chem. 43:3205-3208 (2000).
Garg et al., Mutations in NOTCH1 cause aortic valve disease. Nature. Sep. 8, 2005;437(7056):270-4. Epub Jul. 17, 2005.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Geistlinger & Guy, "An Inhibitor of the Interaction of Thyroid Hormone Receptor β and Glucocorticoid Interacting Protein 1," J. Am. Chem. Soc. 123:1525-1526 (2001).
Gemperli et al., "Paralog-selective Ligands for Bcl-2 Proteins," J. Am. Chem. Soc. 127:1596-1597 (2005).
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Giannis et aL, Peptidomimetics for Receptor Ligands—Discovery, Development, and Medical Perspectives. Angew Chem Int Ed Engl. 1993;32:1244-67.
Glover & Harrison, "Crystal Structure of the Heterodimeric bZIP Transcription Factor c-Fos-c-Jun Bound to DNA," Nature 373:257-261 (1995).
Gong et al. LDL receptor-related protein 5 (LRP5) affects bone accrual and eye development. Cell 107:513-523 (Nov. 16, 2001).
Goodson et al., Potential Growth Antagonists. I. Hydantoins and Disubstituted Glycines. J Org Chem. 1960;25:1920-24.
Gorlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Gras-Masse, et al. Influence of helical organization on immunogenicity and antigenicity of synthetic peptides. Mol Immunol. Jul. 1988;25(7):673-8.
Greenfield et al. Computed circular dichroism spectra for the evaluation of protein conformation. Biochemistry. Oct. 8, 1969;(10):4108-4116.
Grossman, et al. Inhibition of oncogenic Wnt signaling through direct targeting of –catenin. Proc. Natl. Acad. Sco. 2012; 109(44):17942-179747.
Grunig et al., Requirement for IL-13 independently of IL-4 in experimental asthma. Science. Dec. 18, 1998;282(5397):2261-3.
Gu, et al. (2002). Mutual dependence of MDM2 and MDMX in their functional inactivation of p53. J Biol Chem 277, 19251-19254.

(56) References Cited

OTHER PUBLICATIONS

Guerlavais, et al. Advancements in Stapled Peptide Drug Discovery & Development. Annual Reports in Medicinal Chemistry, vol. 49 49 (2014): 331-345.

Guinn et al., Synthesis and characterization of polyamides containing unnatural amino acids. Biopolymers. May 1995;35(5):503-12.

Guo et al., Probing the alpha-helical structural stability of stapled p53 peptides: molecular dynamics simulations and analysis. Chem Biol Drug Des. Apr. 2010;75(4):348-59. doi: 10.1111/.1747-0285.2010.00951.x.

Gupta et al., Long-term effects of tumor necrosis factor-alpha treatment on insulin signaling GUPTA pathway in HepG2 cells and HepG2 cells overexpressing constitutively active Akt/PKB. J Cell Biochem. Feb. 15, 2007;100(3):593-607.

Hamard, et al (2012). P53 basic C terminus regulates p53 functions through DNA binding modulation of subset of target genes. J Biol Chem 287, 22397-22407.

Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.

Harris et al., Synthesis of proline-modified analogues of the neuroprotective agent glycyl-1-prolyl-glutamic acid (GPE). Tetrahedron. 2005;61:10018-35.

Harrison, et al. Downsizing human, bacterial, and viral proteins to short water-stable alpha helices that maintain biological potency. Proc Natl Acad Sci U S A. Jun. 29, 2010;107(26):11686-91. doi: 10.1073/pnas.1002498107. Epub Jun. 11, 2010.

Hartmann, A Wnt canon orchestrating osteoblastogenesis. Trends Cell Biol. Mar. 2006;16(3):151-8. Epub Feb. 7, 2006.

Hartmann et al., Dual roles of Wnt signaling during chondrogenesis in the chicken limb. Development. Jul. 2000;127(14):3141-59.

Haupt, et al. (1997). Mdm2 promotes the rapid degradation of p53. Nature 387, 296-299.

Hecht, S.M., ed. Bioorganic Chemistry: Peptides and Proteins. Oxford University Press. New York; 1998.

Hellman et al., Electrophoretic mobility shift assay (EMSA) for detecting protein-nucleic acid interactions. Nat Protoc. 2007;2(8):1849-61.

Hemerka, et al. Detection and characterization of influenza A virus PA-PB2 interaction through a bimolecular fluorescence complementation assay. J Virol. Apr. 2009;83(8):3944-55. doi: 10.1128/JVI.02300-08. Epub Feb. 4, 2009.

Henchey et al., Contemporary strategies for the stabilization of peptides in the a-helical conformation. Curr Opin Chem Biol. 2008;12:692-97.

Henchey, et al. High specificity in protein recognition by hydrogen-bond-surrogate α-helices: selective inhibition of the p53/MDM2 complex. Chembiochem. Oct. 18, 2010;11(15):2104-7. doi: 10.1002/cbic.201000378.

Henchey, et al. Inhibition of Hypoxia Inducible Factor 1-Transcription Coactivator Interaction by a Hydrogen Bond Surrogate α-Helix. J Am Chem Soc. Jan. 27, 2010;132(3):941-3.

Hessa, et al. Recognition of transmembrane helices by the endoplasmic reticulum translocon. Nature. Jan. 27, 2005;433(7024):377-81.

Hilton et al., Notch signaling maintains bone marrow mesenchymal progenitors by suppressing osteoblast differentiation. Nat Med. Mar. 2008;14(3):306-14. doi: 10.1038/nm1716. Epub Feb. 24, 2008.

Hipfner et al., Connecting proliferation and apoptosis in development and disease. Nat Rev Mol Cell Biol. Oct. 2004;5(10):805-15.

Hoang et al., Dickkopf 3 inhibits invasion and motility of Saos-2 osteosarcoma cells by modulating the Wnt-beta-catenin pathway. Cancer Res. Apr. 15, 2004;64(8):2734-9.

Holford et al., Adding 'splice' to protein engineering. Structure. Aug. 15, 1998;6(8):951-6.

Honda, et al. Oncoprotein MDM2 is a ubiquitin ligase E3 for tumor suppressor p53. FEBS Lett. Dec. 22, 1997;420(1):25-7.

Hong, et al. Efficient removal of ruthenium byproducts from olefin metathesis products by simple aqueous extraction. Org Lett. May 10, 2007;9(10):1955-7.

Horiguchi, et al. Identification and characterization of the ER/lipid droplet-targeting sequence in 17beta-hydroxysteroid dehydrogenase type 11. Arch Biochem Biophys. Nov. 15, 2008;479(2):121-30. doi: 10.1016/j.abb.2008.08.020. Epub Sep. 10, 2008.

Horne, et al. Foldamers with heterogeneous backbones. Acc Chem Res. Oct. 2008;41(10):1399-408. doi: 10.1021/ar800009n. Epub Jul. 1, 2008.

Horne, et al. Structural and biological mimicry of protein surface recognition by alpha/beta-peptide foldamers. Proc Natl Acad Sci U S A. Sep. 1, 2009;106(35)14751-6. doi: 10.1073/pnas.0902663106. Epub Aug. 17, 2009.

Hossain, et al. Solid phase synthesis and structural analysis of novel A-chain dicarba analogs of human relaxin-3 (INSL7) that exhibit full biological activity. Org Biomol Chem. Apr. 21, 2009;7(8):1547-53. doi: 10.1039/b821882j. Epub Feb. 24, 2009.

Huang et al., How insulin binds: the B-chain alpha-helix contacts the Li beta-helix of the insulin receptor. J Mol Biol. Aug. 6, 2004;341(2):529-50.

Huang et al., Tankyrase inhibition stabilizes axin and antagonizes Wnt signalling. Nature. Oct. 1, 2009;461(7264):614-20. Epub Sep. 16, 2009.

Hunt, S. The Non-Protein Amino Acids. In: Barrett G.C., ed. Chemistry and Biochemistry of the Amino Acids. New York; Chapman and Hall; 1985.

International Preliminary Report on Patentability dated Apr. 14, 2016 for PCT/US2014/058680.

International Preliminary Report on Patentability dated Dec. 17, 2015 for PCT/US2014/41338.

International Preliminary Report on Patentability dated Dec. 23, 2015 for PCT/US2014/042329.

International Preliminary Report on Patentability for PCT/US2008/058575 dated Oct. 8, 2009.

International Preliminary Report on Patentability for PCT/US2009/004260 dated Feb. 3, 2011.

International Preliminary Report on Patentability for PCT/US2010/001952 dated Jan. 26, 2012.

International Preliminary Report on Patentability for PCT/US2011/052755, dated Apr. 4, 2013.

International Preliminary Report on Patentability for PCT/US2012/042719, dated Jan. 3, 2014.

International Preliminary Report on Patentability for PCT/US2012/042738, dated Jan. 3, 2014.

International Preliminary Report on Patentability for PCT/US2013/062004, dated Apr. 9, 2015.

International Preliminary Report on Patentability for PCT/US2013/062929, dated Apr. 16, 2015.

International Preliminary Report on Patentability for PCT/US2014/025544, dated Sep. 24, 2015.

International search report and written opinion dated Feb. 7, 2013 for PCT Application No. US12/60913.

International search report and written opinion dated Feb. 9, 2016 for PCT Application No. PCT/US2015/052018.

International search report and written opinion dated May 9, 2016 for PCT Application No. PCTUS2016/023275.

International search report and written opinion dated May 18, 2010 for PCT Application No. US2009/057592.

International Search Report and Written Opinion dated Nov. 10, 2014 for PCT/US2014/41338.

International Search Report and Written Opinion dated Nov. 24, 2014 for PCT/US2014/042329.

International search report and written opinion dated Dec. 4, 2015 for PCT Application No. PCT/US2015/052031.

International search report and written opinion dated Dec. 6, 2016 for PCT Application No. PCT/US2016/050194.

International Search Report and Written Opinion for PCT/US2008/052580, dated May 16, 2008.

International Search Report and Written Opinion for PCT/US2008/058575 dated Nov. 17, 2008.

International Search Report and Written Opinion for PCT/US2009/004260 dated Oct. 15, 2010.

(56) References Cited

OTHER PUBLICATIONS

International Search Report and Written Opinion for PCT/US2010/001952 dated Feb. 2, 2011.
International Search Report and Written Opinion for PCT/US2011/052755 dated Apr. 25, 2012.
International Search Report and Written Opinion for PCT/US2012/042719, dated Nov. 1, 2012.
International Search Report and Written Opinion for PCT/US2012/042738, dated Oct. 18, 2012.
International Search Report and Written Opinion for PCT/US2013/062004, dated Apr. 23, 2014.
International Search Report and Written Opinion for PCT/US2013/062929, dated Jan. 30, 2014.
International Search Report and Written Opinion for PCT/US2014/025544, dated Sep. 10, 2014.
International Search Report and Written Opinion for PCT/US2014/058680, dated Apr. 23, 2015.
International search report dated May 11, 2006 for PCT Application No. US2005/016894.
International search report dated Mar. 17, 2010 for PCT Application No. US2009-057931.
International search report with written opinion dated Feb. 16, 2017 for PCT/US2016/045165.
Invitation to Pay Additional Fees for PCT/US2009/004260 dated Mar. 19, 2010.
Invitation to Pay Additional Fees for PCT/US2010/001952 dated Oct. 29, 2010.
Invitation to Pay Additional Fees for PCT/US2011/052755 dated Feb. 16, 2012.
Invitation to Pay Additional Fees for PCT/US2013/062004, dated Jan. 2, 2014.
Invitation to Pay Aditional Fes for PCT/US2014/025544, dated Jul. 22, 2014.
Ishikawa, et al. (2007). Chemotherapy-resistant human AML stem cells home to and engraft within the bone-marrow endosteal region. Nat Biotechnol 25, 1315-1321.
Izdebski, et al. Synthesis and biological evaluation of superactive agonists of growth hormone-releasing hormone. Proc Natl Acad Sci U S A. May 23, 1995;92(11):4872-6.
Jamieson et al., Granulocyte-macrophage progenitors as candidate leukemic stem cells in blast-crisis CML. N Engl J Med. Aug. 12, 2004;351(7):657-67.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Joerger, et al. Structural biology of the tumor suppressor p53. Annu Rev Biochem. 2008;77:557-82. doi: 10.1146/annurev.biochem.77.060806.091238.
Jones, et al. (1998). Overexpression of Mdm2 in mice reveals a p53-independent role for Mdm2 in tumorigenesis. Proc Natl Acad Sci U S A 95, 15608-15612.
Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Joutel et al., Notch3 mutations in CADASIL, a hereditary adult-onset condition causing stroke and dementia. Nature. Oct. 24, 1996;383(6602):707-10.
Jung, et al. (2013). TXNIP maintains the hematopoietic cell pool by switching the function of p53 under oxidative stress. Cell Metab 18, 75-85.
Junutula et al., Molecular characterization of RabII interactions with members of the family of Rab I-interacting proteins. J Biol Chem. Aug. 6, 2004;279(32):33430-7. Epub Jun. 1, 2004.
Kandoth et al. Mutational landscape and significance across 12 major cancer types. Nature 502(7471):333-339 (2013).
Karwoski et al., Lysinonorleucine cross-link formation in alpha amino heptenoic acid-substituted peptide derivatives. Biopolymers. 1978;17(5):1119-27.

Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul & Balaram, "Stereochemical Control of Peptide Folding," Bioorg. Med. Chem. 7:105-117 (1999).
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.
Kazmaier, Sythesis of Quaternary Amino Acids Containing 13, γ- as well as 7,6-Unsaturated Side Chains via Chelate-Enolate Claisen Rearrangement. Tetrahedron Letters. 1996;37(30):5351-4.
Kelly-Welch et al, Interleukin-4 and Interleukin-13 Signaling Connections Maps. Science. 2003;300:1527-28.
Kemp et al., "Studies of N-Terminal Templates for α-Helix Formation. Synthesis and Conformational Analysis of Peptide Conjugates of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6683-6697 (1991).
Khalil et al., An efficient and high yield method for the N-tert-butoxycarbonyl protection of sterically hindered amino acids. Tetrahedron Lett. 1996;37(20):3441-44.
Kim et al., Introduction of all-hydrocarbon i,i+3 staples into alpha-helices via ring-closing olefin metathesis. Org Lett. Jul. 2, 2010;12(13):3046-9. doi: 10.1021/011010449.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.
Kimmerlin et al., '100 years of peptide synthesis': ligation methods for peptide and protein synthesis with applications to beta-peptide assemblies. J Pept Res. Feb. 2005;65(2):229-60.
Kinage, et al. Highly regio-selective synthesis of beta-amino alcohol by reaction with aniline and propylene carbonate in self solvent systems over large pore zeolite catalyst. Green and Sustainable Chem. Aug. 2011;1: 76-84.
Kinzler et al., Identification of FAP locus genes from chromosome 5q21. Science. Aug. 9, 1991;253(5020):661-5.
Knackmuss et al., Specific inhibition of interleukin-13 activity by a recombinant human single-chain immunoglobulin domain directed against the IL-13 receptor alphaI chain. Biol Chem. Mar. 2007;388(3):325-30.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kondo et al., Frizzled 4 gene (FZD4) mutations in patients with familial exudative vitreoretinopathy with variable expressivity. Br J Ophthalmol. Oct. 2003;87(10):1291-5.
Konishi et al Gamma-secretase inhibitor prevents Notch3 activation and reduces proliferation in human lung cancers. Cancer Res. Sep. 1, 2007;67(17):8051-7.
Korcsmaros et al., Uniformly curated signaling pathways reveal tissue-specific cross-talks and support drug target discovery. Bioinformatics. Aug. 15, 2010;26(16):2042-50. Epub Jun. 11, 2010.
Korinek et al. Depletion of epithelial stem-cell compartments in the small intestine of mice lacking Tcf-4. Nat Genet 19(4):379-383 (1998).
Kosir, et al. Breast Cancer. Available at https://www.merckmanuals.com/home/women-s-health-issues/breast-disorders/breast-cancer. Accessed on Jun. 29, 2016.
Kotha et al., Modification of constrained peptides by ring-closing metathesis reaction. Bioorg Med Chem Lett. Jun. 4, 2001;11(11):1421-3.

(56) References Cited

OTHER PUBLICATIONS

Kouzarides, Acetylation: a regulatory modification to rival phosphorylation? EMBO J. Mar. 15, 2000;19(6):1176-9.
Kovall et al., Crystal structure of the nuclear effector of Notch signaling, CSL, bound to DNA. EMBO J. Sep. 1, 2004;23(17):3441-51. Epub Aug. 5, 2004.
Kozlovsky et aL, GSK-3 and the neurodevelopmental hypothesis of schizophrenia. Eur Neuropsychopharmacol. Feb. 2002;12(1):13-25.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kubbutat, et al. Regulation of p53 stability by Mdm2. Nature. May 15, 1997;387(6630):299-303.
Kung, et al. Suppression of tumor growth through disruption of hypoxia-inducible transcription. Nature Medicine. 2000; 6(12):1335-1340.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Kussie et al, "Structure of the MDM2 Oncoprotein Bound to the p53 Tumor Suppressor Transactivation Domain," Science 274:948-953 (1996).
Kutchukian et al., All-atom model for stabilization of alpha-helical structure in peptides by hydrocarbon staples. J Am Chem Soc. Apr. 8, 2009;131(13):4622-7.
Lacombe et al. Reduction of olefins on solid support using diimide. Tetrahedron Letters. 1998;39:6785-6786.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.
Larock, A. Comprehensive Organic Transformations. VCH Publishers, (1989).
Le Geuzennec et al., Molecular characterization of Sin3 PAH-domain interactor specificity and identification of PAH partners. Nucleic Acids Res. 2006;34(14):3929-37. Epub Aug. 12, 2006.
Le Geuzennec et al Molecular determinants of the interaction of Mad with the PAH2 domain of mSin3. J Biol Chem. Jun. 11, 2004;279(24):25823-9. Epub Mar. 26, 2004.
Lee, et al. Novel pyrrolopyrimidine-based α-helix mimetics: cell-permeable inhibitors of protein-protein interactions. J Am Chem Soc. Feb. 2, 2011;133(4):676-9. doi: 10.1021/ja108230s.
Lenntech BV Water Treatment Solutions. http://www.lenntech.com/periodic/elements/ru.htm.Copyright © 1998-2014.
Lenos, et al. (2012). Alternate splicing of the p53 inhibitor HDMX offers a superior prognostic biomarker than p53 mutation in human cancer. Cancer Res 72, 4074-4084.
Letai, et al. Distinct BH3 Domains Either Sensitize or Activate Mitochondrial Apoptosis, Serving as Prototype Cancer Therapeutics. Cancer Cell. 2002; 2:183-192.
Lewis et al., Apoptosis in T cell acute lymphoblastic leukemia cells after cell cycle arrest induced by pharmacological inhibition of notch signaling. Chem Biol. Feb. 2007;14(2):209-19.
Li, et al. (2012). Activation of p53 by SIRT1 inhibition enhances elimination of CML leukemia stem cells in combination with imatinib. Cancer Cell 21, 266-281.
Li, et al. (2014). MDM4 overexpressed in acute myeloid leukemia patients with complex karyotype and wild-type TP53. PLoS One 9, e113088.
Li et al., Alagille syndrome is caused by mutations in human Jagged1, which encodes a ligand for Notch1. Nat Genet. Jul. 1997;16(3):243-51.
Li, et al. Application of Olefin Metathesis in Organic Synthesis. Speciality Petrochemicals. 2007; 79-82 (in Chinese with English abstract).
Li et al., Modulation of Notch signaling by antibodies specific for the extracellular negative regulatory region of NOTCH3. J Biol Chem. Mar. 21, 2008;283(12):8046-54. doi: 10.1074/jbc.M800170200. Epub Jan. 8, 2008.
Li et al., Notch3 signaling promotes the development of pulmonary arterial hypertension. Nat Med. Nov. 2009;15(11):1289-97. doi: 10.1038/nm.2021. Epub Oct. 25, 2009.
Li, et at. Molecular-targeted agents combination therapy for cancer: Developments and potentials. International Journal of Cancer 134.6 (2014): 1257-1269.
Liang et al., Wnt5a inhibits B cell proliferation and functions as a tumor suppressor in hematopoietic tissue. Cancer Cell. Nov. 2003;4(5):349-60.
Lifson & Roig, "On the Theory of Helix-coil Transition in Polypeptides," J. Chem. Phys. 34(6):1963-1974 (1961).
Lindsay et al., Rab coupling protein (RCP), a novel Rab4 and Rab11 effector protein. J Biol Chem. Apr. 5, 2002;277(14):12190-9. Epub Jan. 10, 2002.
Liskamp, et al. Conformationally restricted amino acids and dipeptides, (non)peptidomimetics and secondary structure mimetics. Recl Travl Chim Pays-Bas. 1994; 113:1-19.
Little et aL, A Mutation in the LDL Receptor-Related Protein 5 Gene Results in the Autosomal Dominant High-Bone-Mass Trait. Am J Hum Genet. 2002;70:11-19.
Liu, et al. (2009). The p53 tumor suppressor protein is a critical regulator of hematopoietic stem cell behavior. Cell Cycle 8, 3120-3124.
Liu et al., Chemical Ligation Approach to Form a Peptide Bond between Unprotected Peptide Segments. Concept and Model Study. J Am Chem Soc. 1994;116(10):4149-53.
Liu et al., Targeted degradation of beta-catenin by chimeric F-box fusion proteins. Biochem Biophys Res Commun. Jan. 23, 2004;313(4):1023-9.
Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.
Logan et al., The Wnt signaling pathway in development and disease. Annu Rev Cell Dev Biol. 2004;20:781-810.
Lohmar et al. Synthese symmetrischerf ketone unter verwendung von 2-Phenyl-2-oxazolin-5-on. (α-Aminosäuren als nucleophile Acyläquivalente, IV.) Chemische Berichte. 1980;113(12): 3706-15.
Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.
Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.
Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Lu et al., Both Pbxl and E2A-Pbx1 bind the DNA motif ATCAATCAA cooperatively with the products of multiple murine Hox genes, some of which are themselves oncogenes. Mol Cell Biol. Jul. 1995;15(7):3786-95.
Lu et al., Structural determinants within Pbxl that mediate cooperative DNA binding with pentapeptide-containing Hox proteins: proposal for a model of a Pbxl-Hox-DNA complex. Mol Cell Biol. Apr. 1996;16(4):1632-40.
Lubman et al., Quantitative dissection of the Notch:CSL interaction: insights into the Notch-mediated transcriptional switch. J Mol Biol. Jan. 19, 2007;365(3):577-89. Epub Oct. 3, 2006.
Luo et al., Wnt signaling and human diseases: what are the therapeutic implications? Lab Invest. Feb. 2007;87(2):97-103. Epub Jan. 8, 2007.
Luscher et al., The basic region/helix-loop-helix/leucine zipper domain of Myc proto-oncoproteins: function and regulation. Oncogene. May 13, 1999;18(19):2955-66.

(56) References Cited

OTHER PUBLICATIONS

Luu et al, Wnt/beta-catenin signaling pathway as a novel cancer drug target. Curr Cancer Drug Targets. Dec. 2004;4(8):653-71.

Macmillan, Evolving strategies for protein synthesis converge on native chemical ligation. Angew Chem Int Ed Engl. Nov. 27, 2006;45(46):7668-72.

Madden, et al. Synthesis of cell-permeable stapled peptide dual inhibitors of the p53-Mdm2/Mdmx interactions via photoinduced cycloaddition. Bioorg Med Chem Lett. Mar. 1, 2011;21(5):1472-5. doi: 10.1016/j.bmcl.2011.01.004. Epub Jan. 7, 2011.

Makimura, et al. Reduced growth hormone secretion is associated with increased carotid intima-media thickness in obesity. The Journal of Clinical Endocrinology & Metabolism. 2009;94(12):5131-5138.

Marqusee & Baldwin, "Helix Stabilization by Glu- . . . Lys+ Salt Bridges in Short Peptides of De Novo Design," Proc. Nat'l Acad. Sci. USA 84:8898-8902 (1987).

Marshall et al., Back to the future: ribonuclease A. Biopolymers. 2008;90(3):259-77.

Maynard, et al. Purification technique for the removal of ruthenium from olefin metathesis reaction products. Tetrahedron Letters. 1999; 40:4137-4140.

Mayo, et al. International Union of Pharmacology. XXXV. The glucagon receptor family. Pharmacol Rev. Mar. 2003;55(1):167-94.

McKern et al., Structure of the insulin receptor ectodomain reveals a folded-over conformation. Nature. Sep. 14, 2006;443(7108):218-21. Epub Sep. 6, 2006.

McNamara et al. Peptides constrained by an aliphatic linkage between two C(alpha) sites: design, synthesis, and unexpected conformational properties of an i,(i+4)-linked peptide. J Org Chem. Jun. 29, 2001;66(13):4585-95.

Mellegaard-Waetzig et al., Allylic amination via decarboxylative c-n bond formation Synlett. 2005;18:2759-2762.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive RabII complexes with members of the family of RabII-interacting proteins regulates RabII endocytic targeting and function. J Biol Chem. Dec. 13, 2002;277(50):49003-10. Epub Oct. 9, 2002.

Miller & Scanlan, "oNBS-SPPS: A New Method for Solid-phase Peptide Synthesis," J. Am. Chem. Soc. 120:2690-2691 (1998).

Miller et al., Application of Ring-Closing Metathesis to the Synthesis of Rigidified Amino Acids and Peptides. J Am Chem Soc. 1996;118(40):9606-9614.

Miller et al., Synthesis of Conformationally Restricted Amino Acids and Peptides Employing Olefin Metathesis. J Am Chem Soc. 1995;117(21):5855-5856.

Miloux et al., Cloning of the human IL-13R alphaI chain and reconstitution with the IL4R alpha of a functional IL-4/IL-13 receptor complex. FEBS Lett. Jan. 20, 1997;401(2-3):163-6.

Min, et al. Structure of an HIF-1alpha-pVHL complex: hydroxyproline recognition in signaling. Science. Jun. 7, 2002;296(5574):1886-9.

Miyaoka et al., Increased expression of Wnt-1 in schizophrenic brains. Schizophr Res. Jul. 27, 1999;38(1):1-6.

Moellering et al., Computational modeling and molecular optimization of stabilized alphahelical peptides targeting NOTCH-CSL transcriptional complexes. European Journal of Cancer Supplements Nov. 2010; 8(7):30. DOI: 10.1016/S1359-6349(10)71774-2. Abstract 69.

Moellering et al., Direct inhibition of the NOTCH transcription factor complex. Nature. Nov. 12, 2009;462(7270):182-8. Erratum in: Nature. Jan. 21, 2010;463(7279):384.

Moon et al., WNT and beta-catenin signalling: diseases and therapies. Nat Rev Genet. Sep. 2004;5(9):689-701.

Morin, beta-catenin signaling and cancer. Bioessays. Dec. 1999;21(12):1021-30.

Morita, et al. Cyclolinopeptides B-E, new cyclic peptides from Linum usitatissimum. Tetrahedron 55.4 (1999): 967-976.

Moses, et al. The growing applications of click chemistry. Chem Soc Rev. Aug. 2007;36(8):1249-62.

Moy et al., Solution structure of human IL-13 and implication for receptor binding. J Mol Biol. Jun. 29, 2001;310(1):219-30.

Mudher et al., Alzheimer's disease-do tauists and baptists finally shake hands? Trends Neurosci. Jan. 2002;25(1):22-6.

Muir et al., Expressed protein ligation: a general method for protein engineering. Proc Natl Acad Sci U S A. Jun. 9, 1998;95(12):6705-10.

Muir, Semisynthesis of proteins by expressed protein ligation. Annu Rev Biochem. 2003;72:249-89. Epub Feb. 27, 2003.

Muller, P. Glossary of terms used in physical organic chemistry. Pure and Applied Chemistry, 1994, vol. 66, pp. 1077-1184.

Muppidi, et al. Achieving cell penetration with distance-matching cysteine cross-linkers: a facile route to cell-permeable peptide dual inhibitors of Mdm2/Mdmx. Chem Commun (Camb). Sep. 7, 2011;47(33):9396-8. doi: 10.1039/c1cc13320a. Epub Jul. 19, 2011.

Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi: 10.1016/j.bmcl.2011.10.009. Epub Oct. 12, 2011.

Murphy, et al. Growth hormone exerts hematopoietic growth-promoting effects in vivo and partially counteracts the myelosuppressive effects of azidothymidine. Blood. Sep. 15, 1992;80(6):1443-7.

Murray, et al. Targeting protein-protein interactions: lessons from p53/MDM2. Biopolymers. 2007;88(5):657-86.

Mustapa, et al. Synthesis of a cyclic peptide containing norlanthionine: effect of the thioether bridge on peptide conformation. J Org Chem. Oct. 17, 2003;68(21):8193-8.

Mynarcik et al., Alanine-scanning mutagenesis of a C-terminal ligand binding domain of the insulin receptor alpha subunit. J Biol Chem. Feb. 2, 1996;271(5):2439-42.

Mynarcik et al., Identification of common ligand binding determinants of the insulin and insulin-like growth factor 1 receptors. Insights into mechanisms of ligand binding. J Biol Chem. Jul. 25, 1997;272(30):18650-5.

Myriem, V. One pot iodination click reaction: A Convenient Preparation of 5-Iodo-1,4-disubstituted-1,2,3-triazole. Date unknown.

Myung et al., The ubiquitin-proteasome pathway and proteasome inhibitors. Med Res Rev. Jul. 2001;21(4):245-73.

Nair et al., X-ray structures of Myc-Max and Mad-Max recognizing DNA. Molecular bases of regulation by proto-oncogenic transcription factors. Cell. Jan. 24, 2003;112(2):193-205.

Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.

Nam et al., Structural basis for cooperativity in recruitment of MAML coactivators to Notch transcription complexes. Cell. Mar. 10, 2006;124(5):973-83.

Nam et al., Structural requirements for assembly of the CSL.intracellular Notch1.Mastermind-like 1 transcriptional activation complex. J Biol Chem. Jun. 6, 2003;278(23):21232-9. Epub Mar. 18, 2003.

Nefedova et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.

Ngo et al. Computational complexity, protein structure prediction, and the levinthal paradox. In: The Protein Folding Problem and Tertiary Structure Prediction. K. Merz, Jr., et al. Eds. 1994:433-506.

Nicole, et al. Identification of key residues for interaction of vasoactive intestinal peptide with human VPAC1 and VPAC2 receptors and development of a highly selective VPAC1 receptor agonist. Alanine scanning and molecular modeling of the peptide. J Biol Chem. Aug. 4, 2000;275(31):24003-12.

Niemann et al., Homozygous WNT3 mutation causes tetra-amelia in a large consanguineous family. Am J Hum Genet. Mar. 2004;74(3):558-63. Epub Feb. 5, 2004.

(56) References Cited

OTHER PUBLICATIONS

Nilsson et al., Staudinger ligation: a peptide from a thioester and azide. Org Lett. Jun. 29, 2000;2(13):1939-41.
Niranjan et al., The Notch pathway in podocytes plays a role in the development of glomerular disease. Nat Med. Mar. 2008;14(3):290-8. doi: 10.1038/nm1731. Epub Mar. 2, 2008.
Nishisho et al., Mutations of chromosome 5q21 genes in FAP and colorectal cancer patients. Science. Aug. 9, 1991;253(5020):665-9.
[No Author Listed] Colorectal Cancer. Merck Manuals. Aug. 21, 2014. http://www.merckmanuals.com/home/digestive_disorders/tumors_ofthe_digestive_system/colorectal_cancer.html. 5 pages.
Noah, et al. A cell-based luminescence assay is effective for high-throughput screening of potential influenza antivirals. Antiviral Res. Jan. 2007;73(1):50-9. Epub Jul. 28, 2006.
Nobuo Izimiya et al. Pepuchido Gosei no Kiso to Jikken (Fundamental of peptide synthesis and experiments, Jan. 20, 1985, p. 271.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Noguera-Troise et al., Blockade of D114 inhibits tumour growth by promoting non-productive angiogenesis. Nature. Dec. 21, 2006;444(7122):1032-7.
Notice of allowance dated May 12, 2016 for U.S. Appl. No. 14/750,649.
Notice of allowance dated Aug. 31, 2016 for U.S. Appl. No. 14/750,649.
Notice of allowance dated Feb. 15, 2017 for U.S. Appl. No. 14/852,368.
Notice of allowance dated Mar. 2, 2017 for U.S. Appl. No. 14/852,368.
Notice of allowance dated Mar. 29, 2017 for U.S. Appl. No. 14/852,368.
Notice of allowance dated Mar. 30, 2015 for U.S. Appl. No. 13/655,378.
Notice of allowance dated May 18, 2016 for U.S. Appl. No. 14/070,354.
Notice of allowance dated Jun. 1, 2016 for U.S. Appl. No. 14/070,354.
Notice of allowance dated Jul. 18, 2016 for U.S. Appl. No. 14/498,063.
Notice of allowance dated Jul. 19, 2016 for U.S. Appl. No. 14/068,844.
Notice of allowance dated Jul. 21, 2016 for U.S. Appl. No. 14/677,679.
Notice of Allowance dated Jul. 22, 2015 for U.S. Appl. No. 14/070,367.
Notice of allowance dated Jul. 28, 2016 for U.S. Appl. No. 14/498,063.
Notice of allowance dated Aug. 16, 2016 for U.S. Appl. No. 14/483,905.
Notice of allowance dated Sep. 14, 2015 for U.S. Appl. No. 13/350,644.
Notice of allowance dated Sep. 22, 2015 for U.S. Appl. No. 12/564,909.
Notice of allowance dated Oct. 14, 2016 for U.S. Appl. No. 14/027,064.
Notice of allowance dated Oct. 23, 2015 for U.S. Appl. No. 13/252,751.
Notice of allowance dated Nov. 17, 2016 for U.S. Appl. No. 14/070,306.
Notice of Allowance, dated May 30, 2013, for U.S. Appl. No. 12/593,384.
Office action dated Jan. 14, 2016 for U.S. Appl. No. 14/027,064.
Office action dated Jan. 29, 2016 for U.S. Appl. No. 14/483,905.
Office action dated Feb. 5, 2016 for U.S. Appl. No. 14/068,844.
Office action dated Feb. 6, 2014 for U.S. Appl. No. 13/350,644.
Office action dated Feb. 13, 2013 for U.S. Appl. No. 12/564,909.
Office action dated Mar. 3, 2017 for U.S. Appl. No. 14/460,848.
Office action dated Mar. 18, 2009 for U.S. Appl. No. 11/678,836.
Office action dated Apr. 17, 2017 for U.S. Appl. No. 15/287,513.
Office action dated Apr. 24, 2015 for U.S. Appl. No. 12/564,909.
Office action dated Apr. 24, 2015 for U.S. Appl. No. 13/350,644.
Office action dated Apr. 28, 2016 for U.S. Appl. No. 14/677,679.
Office action dated Apr. 28, 2017 for U.S. Appl. No. 14/608,641.
Office action dated May 17, 2017 for U.S. Appl. No. 14/864,687.
Office action dated May 24, 2016 for U.S. Appl. No. 14/027,064.
Office action dated Jun. 6, 2016for U.S. Appl. No. 14/608,641.
Office action dated Jun. 18, 2014 for U.S. Appl. No. 12/564,909.
Office action dated Jun. 18, 2015 for U.S. Appl. No. 14/068,844.
Office action dated Jun. 19, 2017 for U.S. Appl. No. 15/135,098.
Office action dated Jul. 24, 2015 for U.S. Appl. No. 13/252,751.
Office action dated Aug. 6, 2015 for U.S. Appl. No. 14/498,063.
Office action dated Sep. 2, 2015 for U.S. Appl. No. 14/608,641.
Office action dated Sep. 20, 2016 for U.S. Appl. No. 14/852,368.
Office action dated Oct. 4, 2016 for U.S. Appl. No. 14/864,801.
Office action dated Oct. 24, 2016 for U.S. Appl. No. 14/718,288.
Office action dated Oct. 26, 2015 for U.S. Appl. No. 14/460,848.
Office action dated Oct. 27, 2016 for U.S. Appl. No. 14/864,687.
Office action dated Nov. 16, 2015 for U.S. Appl. No. 14/070,354.
Office action dated Nov. 26, 2013 for U.S. Appl. No. 13/655,378.
Office action dated Dec. 7, 2015 for U.S. Appl. No. 14/677,679.
Office action dated Dec. 19, 2012 for U.S. Appl. No. 13/350,644.
Office action dated Dec. 23, 2015 for U.S. Appl. No. 14/498,063.
Office action dated May 29, 2013 for U.S. Appl. No. 13/350,644.
Office Communication, dated Jan. 3, 2013, for U.S. Appl. No. 12/593,384.
O'Shea et al., "Mechanism of Specificity in the Fos-Jun Oncoprotein Heterodimer," Cell 68:699-708 (1992).
Okamura et al., Redundant regulation of T cell differentiation and TCRalpha gene expression by the transcription factors LEF-1 and TCF-1. Immunity. Jan. 1998;8(1):11-20.
Oliner, et al. Oncoprotein MDM2 conceals the activation domain of tumour suppressor p53. Nature. Apr. 29, 1993;362(6423):857-60.
Olson et al., Sizing up the heart: development redux in disease. Genes Dev. Aug. 15, 2003;17(16):1937-56. Epub Jul. 31, 2003.
O'Neil et al., FBW7 mutations in leukemic cells mediate NOTCH pathway activation and resistance to gamma-secretase inhibitors. J Exp Med. Aug. 6, 2007;204(8):1813-24. Epub Jul. 23, 2007.
Oswald et al., RBP-Jkappa/SHARP recruits CtIP/CtBP corepressors to silence Notch target genes. Mol Cell Biol. Dec. 2005;25(23):10379-90.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palchaudhuri et al.,Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html.
Palomero et al., Mutational loss of PTEN induces resistance to NOTCH1 inhibition in T-cell leukemia. Nat Med. Oct. 2007;13(10):1203-10. Epub Sep. 16, 2007.
Pangborn et al., "Safe and Convenient Procedure for Solvent Purification," Organometallics 15:1518-1520 (1996).
Park et al., Notch3 gene amplification in ovarian cancer. Cancer Res. Jun. 15, 2006;66(12):6312-8.
Parrish et al., Perspectives on alkyl carbonates in organic synthesis. Tetrahedron, 2000; 56(42): 8207-8237.
Parthier, et al. Passing the baton in class B GPCRs: peptide hormone activation via helix induction? Trends Biochem Sci. Jun. 2009;34(6):303-10. doi: 10.1016/j.tibs.2009.02.004. Epub May 14, 2009.
Passegue, et al. (2003). Normal and leukemic hematopoiesis: are leukemias a stem cell disorder or a reacquisition of stem cell characteristics? Proc Natl Acad Sci U S A 100 Suppl 1, 11842-11849.
Patgiri, et al. A hydrogen bond surrogate approach for stabilization of short peptide sequences in alpha-helical conformation. Acc Chem Res. Oct. 2008;41(10):1289-300. Epub Jul. 17, 2008.
Patgiri et al. An orthosteric inhibitor of the Ras-Sos interaction. Nat Chem Bio 7:585-587 (2011).

(56) References Cited

OTHER PUBLICATIONS

Patgiri, et al. Solid phase synthesis of hydrogen bond surrogate derived alpha-helices: resolving the case of a difficult amide coupling. Org Biomol Chem. Apr. 21, 2010;8(8):1773-6.
Peller, et al. (2003). TP53 in hematological cancer: low incidence of mutations with significant clinical relevance. Hum Mutat 21, 277-284.
Pellois et al., Semisynthetic proteins in mechanistic studies: using chemistry to go where nature can't. Curr Opin Chem Biol. Oct. 2006;10(5):487-91. Epub Aug. 28, 2006.
Peryshkov, et al. Z-Selective olefin metathesis reactions promoted by tungsten oxo alkylidene complexes. J Am Chem Soc. Dec. 28, 2011;133(51):20754-7. doi: 10.1021/ja210349m. Epub Nov. 30, 2011.
Petros et al., "Rationale for Bcl-xL/Bad Peptide Complex Formation from Structure, Mutagenesis, and Biophysical Studies," Protein Sci. 9:2528-2534 (2000).
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2009.
Plenat, et al. [Formaldehyde fixation in the third millennium]. Ann Pathol. Feb. 2001;21(1):29-47.
Polakis, The oncogenic activation of beta-catenin. Curr Opin Genet Dev. Feb. 1999;9(1):15-21.
Punna, et al. Head-to-tail peptide cyclodimerization by copper-catalyzed azide-alkyne cycloaddition. Angew Chem Int Ed Engl. Apr. 8, 2005;44(15):2215-20.
Qi, J., et al. (2015). HDAC8 Inhibition Specifically Targets Inv(16) Acute Myeloid Leukemic Stem Cells by Restoring p53 Acetylation. Cell Stem Cell 17, 597-610.
Qian & Schellman, "Helix-coil Theories: A Comparative Study for Finite Length Polypeptides," J. Phys. Chem. 96:3987-3994 (1992).
Ran, et al. Double Nicking by RNA-Guided CRISPR Cas9 for Enhanced Genome Editing Specificity. Cell. Aug. 28, 2013. pii: S0092-8674(13)01015-5. doi: 10.1016/j.cell.2013.08.021. [Epub ahead of print].
Rao et al., Inhibition of NOTCH signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.
Rasmussen, et al. Ruthenium-catalyzed cycloaddition of aryl azides and alkynes. Org Lett. Dec. 20, 2007;9(26):5337-9.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reis, et al. (2016). Acute myeloid leukemia patients' clinical response to idasanutlin (RG7388) is associated with pre-treatment MDM2 protein expression in leukemic blasts. Haematologica 101, e185-188.
Remington: The Science and Practice of Pharmacy. 19th Edition, 1995.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Riddoch, et al. A solid-phase labeling strategy for the preparation of technetium and rhenium bifunctional chelate complexes and associated peptide conjugates. Bioconjug Chem. Jan.-Feb. 2006;17(1):226-35.
Ridgway et al., Inhibition of D114 signalling inhibits tumour growth by deregulating angiogenesis. Nature. Dec. 21, 2006;444(7122):1083-7.

Rivlin, et al. Mutations in the p53 Tumor Suppressor Gene: Important Milestones at the Various Steps of Tumorigenesis. Genes & Cancer 2011, 2:466. Originally published online May 18, 2011.
Robberecht, et al. Structural requirements for the activation of rat anterior pituitary adenylate cyclase by growth hormone-releasing factor (GRF): discovery of (N-Ac-Tyr1, D-Arg2)-GRF(1-29)-NH2 as a GRF antagonist on membranes. Endocrinology. Nov. 1985;117(5):1759-64.
Robert, A hierarchical "nesting" approach to describe the stability of alpha helices with side-chain interactions. Biopolymers. 1990;30(3-4):335-47.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roehrl et al., "A General Framework for Development and Data Analysis of Competitive High-throughput Screens for Small-molecule Inhibitors of Protein-Protein Interactions by Fluorescence Polarization," Biochemistry 43:16056-16066 (2004).
Roehrl et al., "Discovery of Small-molecule Inhibitors of the NFAT-Calcineurin Interaction by Competitive High-throughput Fluorescence Polarization Screening," Biochemistry 43:16067-16075 (2004).
Roos et al., Synthesis of a-Substituted a-Amino Acids via Cationic Intermediates. J Org Chem. 1993;58:3259-68.
Ross et al. Inhibition of adipogenesis by Wnt signaling. Science 289:950-953 (2000).
Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).
Rutledge et al., "A View to a Kill: Ligands for Bcl-2 Family Proteins," Curr. Opin. Chem. Biol. 6:479-485 (2002).
Rytting, et al. Overview of Leukemia. Available at http://www.merckmanuals.com/home/blood-disorders/leukernias/overview-of%20leukemia?qt=Leukemia&%2520alt=sh. Accessed on Jun. 29, 2016.
Sadot et al., Down-regulation of beta-catenin by activated p53. Mol Cell Biol. Oct. 2001;21(20):6768-81.
Saiki, et al. Primer-directed enzymatic amplification of DNA with a thermostable DNA polymerase. Science. Jan. 29, 1988;239(4839):487-91.
Sali et al., Stabilization of protein structure by interaction of alpha-helix dipole with a charged side chain. Nature. Oct. 20, 1988;335(6192):740-3.
Samant et al. "Structure activity relationship studies of gonadotropin releasing hormone antagonists containing S-aryl/alkyl norcysteines and their oxidized derivatives," J. Med. Chem. Apr. 3, 2007. vol. 50, No. 3, pp. 2067-2077.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sawyer, et al. Macrocyclic a-Helical Peptide Drug Discovery. Macrocycles in Drug Discovery 40 (2014): 339-366.
Saxon et al., Cell surface engineering by a modified Staudinger reaction. Science. Mar. 17, 2000;287(5460):2007-10.
Schaffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schaffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schafmeister, et al. An all-hydrocarbon cross-linking system for enhancing the helicity and metabolic stability of peptides. Journal of the American Chemical Society. 2000;122(24):5891-5892.
Scheffzek et al. The Ras-RasGAP complex: structural basis for GTPase activation and its loss in oncogenic Ras mutants. Science 277(5324):333-338 (1997).

(56) References Cited

OTHER PUBLICATIONS

Schmiedeberg et al. Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.
Seabra et al., Rab GTPases, intracellular traffic and disease. Trends Mol Med. Jan. 2002;8(1):23-30.
Seebach, et al. Beta-peptidic peptidomimetics. Acc Chem Res. Oct. 2008;41(10):1366-75. doi: 10.1021/ar700263g. Epub Jun. 26, 2008.
Seebach, et al. Self-Regeneration of Stereocenters (SRS)—Applications, Limitations, and Abandonment of a Synthetic Principle. Angewandte Chemie International Edition in English. 1996;35(23-24):2708-2748.
Seiffert et al., Presenilin-1 and -2 are molecular targets for gamma-secretase inhibitors. J Biol Chem. Nov. 3, 2000;275(44):34086-91.
Shair, A closer view of an oncoprotein-tumor suppressor interaction. Chem Biol. Nov. 1997;4(11):791-4.
Shangary, et al. Targeting the MDM2-p53 interaction for cancer therapy. Clin Cancer Res. Sep. 1, 2008;14(17):5318-24. doi: 10.1158/1078-0432.CCR-07-5136.
Sharp, et al. (1999). Stabilization of the MDM2 oncoprotein by interaction with the structurally related MDMX protein. J Biol Chem 274, 38189-38196.
Shenk et al. Biochemical method for mapping mutational alterations in DNA with S1 nuclease: the location of deletions and temperature-sensitive mutations in simian virus 40. Proc Natl Acad Sci U S A. Mar. 1975;72(3):989-93.
Shiba et al., Structural basis for RabII-dependent membrane recruitment of a family of RabII-interacting protein 3 (FIP3)/Arfophilin-1. Proc Natl Acad Sci U S A. Oct. 17, 2006;103(42):15416-21. Epub Oct. 9, 2006.
Shvarts, et al. (1996). MDMX: a novel p53-binding protein with some functional properties of MDM2. EMBO J 15, 5349-5357.
Si et aL, CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Siddle et al., Specificity in ligand binding and intracellular signalling by insulin and insulin-like growth factor receptors. Biochem Soc Trans. Aug. 2001;29(Pt 4):513-25.
Singh et al.,Iridium(I)-catalyzed regio- and enantioselective allylic amidation.Tet. Lett. 2007;48(40): 7094-7098.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Sparey et al., Cyclic sulfamide gamma-secretase inhibitors. Bioorg Med Chem Lett. Oct. 1, 2005;15(19):4212-6.
Spouge, et al. Strong conformational propensities enhance t cell antigenicity. J Immunol. Jan. 1, 1987;138(1):204-12.
Stad, et al. (2000). Hdmx stabilizes Mdm2 and p53. J Biol Chem 275, 28039-28044.
Stad, et al. (2001). Mdmx stabilizes p53 and Mdm2 via two distinct mechanisms. EMBO Rep 2, 1029-1034.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Still et al., "Rapid Chromatographic Technique for Preparative Separations with Moderate Resolution," J. Org. Chem. 43(14):2923-2925 (1978).
Still et al., Semianalytical Treatment of Solvation for Molecular Mechanics and Dynamics. J Am Chem Soc. 1990;112:6127-29.
Struhl et al., Presenilin is required for activity and nuclear access of Notch in Drosophila. Nature. Apr. 8, 1999;398(6727):522-5.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Stymiest, et al. Supporting information for: Solid Phase Synthesis of Dicarba Analogs of the Biologically Active Peptide Hormone Oxytocin Using Ring Closing Metathesis. Organic Letters. 2003. 1-8.
Stymiest, et al. Synthesis of biologically active dicarba analogues of the peptide hormone oxytocin using ring-closing metathesis. Org Lett. Jan. 9, 2003;5(1):47-9.
Su et al., Eradication of pathogenic beta-catenin by Skpl/Cullin/F box ubiquitination machinery. Proc Natl Acad Sci U S A. Oct. 28, 2003;100(22):12729-34. Epub Oct. 16, 2003.
Su, et al. In vitro stability of growth hormone releasing factor (GRF) analogs in porcine plasma. Horm Metab Res. Jan. 1991;23(1):15-21.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Suter, et al. (2011). Mammalian genes are transcribed with widely different bursting kinetics. Science 332, 472-474.
Takeda et al. Human sebaceous tumors harbor inactivating mutations in LEF I . Nat Med. 12(4):395-397 (2006).
Takeishi, et al. (2013). Ablation of Fbxw7 eliminates leukemia-initiating cells by preventing quiescence. Cancer Cell 23, 347-361.
Tan, et al. (2014). High Mdm4 levels suppress p53 activity and enhance its half-life in acute myeloid leukaemia. Oncotarget 5, 933-943.
Tang, et al. Construction and activity of a novel GHRH analog, Pro-Pro-hGHRH(1-44)-Gly-Gly-Cys. Acta Pharmacol Sin. Nov. 2004;25(11):1464-70.
Tanimura, et al. (1999). MDM2 interacts with MDMX through their RING finger domains. FEBS Lett 447, 5-9.
Thallinger, et al. Mcl-1 is a novel therapeutic target for human sarcoma: synergistic inhibition of human sarcoma xenotransplants by a combination of mcl-1 antisense oligonucleotides with low-dose cyclophosphamide. Clin Cancer Res. Jun. 15, 2004;10(12 Pt 1):4185-91.
Therasse, et al. New guidelines to evaluate the response to treatment in solid tumors. European Organization for Research and Treatment of Cancer, National Cancer Institute of the United States, National Cancer Institute of Canada. J Natl Cancer Inst. Feb. 2, 2000;92(3):205-16.
Thompson et al., Mutants of interleukin 13 with altered reactivity toward interleukin 13 receptors. J Biol Chem. Oct. 15, 1999;274(42):29944-50.
Thundimadathil, New Reactions with Click Chemistry. An R&D Magazine Webcast. Oct. 10, 2012. Available at http://www.rdmag.com/articles/2012/10/new-reactions-click-chemistry.
Tian et al., Linear non-competitive inhibition of solubilized human gamma-secretase by pepstatin A methylester, L685458, sulfonamides, and benzodiazepines. J Biol Chem. Aug. 30, 2002;277(35):31499-505. Epub Jun. 18, 2002.
Tian, et al. Recombinant human growth hormone promotes hematopoietic reconstitution after syngeneic bone marrow transplantation in mice. Stem Cells. 1998;16(3):193-9.

(56) References Cited

OTHER PUBLICATIONS

Tian et al.; The role of the Wnt-signaling antagonist DKKI in the development of osteolytic lesions in multiple myeloma. N Engl J Med 349:2483-3494 (2003).
Tolbert et al., New methods for proteomic research: preparation of proteins with N-terminal cysteines for labeling and conjugation. Angew Chem Int Ed Engl. Jun. 17, 2002;41(12):2171-4.
Toniolo, Conformationally restricted peptides through short-range cyclizations. Int J Pept Protein Res. Apr. 1990;35(4):287-300.
Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.
Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Torrance et al., Combinatorial chemoprevention of intestinal neoplasia. Nat Med. Sep. 2000;6(9):1024-8.
Tsuji et al., Antiproliferative activity of REIC/DKK-3 and its significant down-regulation in non-small-cell lung carcinomas. Biochem Biophys Res Commun. Nov. 23, 2001;289(1):257-63.
Tsuji et al., Synthesis of γ, σ-unsaturated ketones by the intramolecular decarboxylative allylation of allyl β-keto carboxylates and alkenyl allyl carbonates catalyzed by molybdenum, nickel, and rhodium complexes. Chemistry Letters. 1984; 13(10):1721-1724.
Tsuruzoe et al., Insulin receptor substrate 3 (IRS-3) and IRS-4 impair IRS-1- and IRS-2-mediated signaling. Mol Cell Biol. Jan. 2001;21(1):26-38.
Turner et al., "Mitsunobu Glycosylation of Nitrobenzenesulfonamides: Novel Route to Amadori Rearrangement Products," Tetrahedron Lett. 40:7039-7042 (1999).
Tyndall, et al. Over one hundred peptide-activated G protein-coupled receptors recognize ligands with turn structure. Chem Rev. Mar. 2005;105(3):793-826.
Tyndall et al., "Proteases Universally Recognize Beta Strands in Their Active Sites," Chem. Rev. 105:973-999 (2005).
Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.
Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Uesugi et al., The alpha-helical FXXPhiPhi motif in p53: TAF interaction and discrimination by MDM2. Proc Natl Acad Sci USA. Dec. 21, 1999;96(26):14801-6.
Ullman et al., Luminescent oxygen channeling immunoassay: measurement of particle binding kinetics by chemiluminescence. Proc Natl Acad Sci U S A. Jun. 7, 1994;91(12):5426-30.
Unpublished U.S. Appl. No. 13/350,644, filed Jan. 13, 2012.
Vaickus et al., Immune markers in hematologic malignancies. Crit Rev Oncol Hematol. Dec. 1991; 11(4):267-97.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Van Hoof, et al. Identification of cell surface proteins for antibody-based selection of human embryonic stem cell-derived cardiomyocytes. J Proteome Res. Mar. 5, 2010;9(3):1610-8. doi: 10.1021/pr901138a.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Vartak et al., Allosteric Modulation of the Dopamine Receptor by Conformationally Constrained Type VI (3-Turn Peptidomimetics of Pro-Leu-Gly-NH2. J Med Chem. 2007;50(26):6725-6729.
Vassilev, et al. (2004). In vivo activation of the p53 pathway by small-molecule antagonists of MDM2. Science 303, 844-848.

Venancio et al., Reconstructing the ubiquitin network: cross-talk with other systems and identification of novel functions. Genome Biol. 2009;10(3):R33. Epub Mar. 30, 2009.
Vera, et al. (2016). Single-Cell and Single-Molecule Analysis of Gene Expression Regulation. Annu Rev Genet 50, 267-291.
Verdine et al., Stapled peptides for intracellular drug targets. Methods Enzymol. 2012;503:3-33. doi: 10.1016/B978-0-12-396962-0.00001-X.
Verdine et al. The challenge of drugging undruggable targets in cancer: lessons learned from targeting BCL-2 family members. Clin Cancer Res. 13(24):7264-7270 (2007).
Verma et al., Small interfering RNAs directed against beta-catenin inhibit the in vitro and in vivo growth of colon cancer cells. Clin Cancer Res. Apr. 2003;9(4):1291-300.
Vila-Perello, et al. A minimalist design approach to antimicrobial agents based on a thionin template. J Med Chem. Jan. 26, 2006;49(2):448-51.
Vu, et al. (2013). Discovery of RG7112: A Small-Molecule MDM2 Inhibitor in Clinical Development. ACS Med Chem Lett 4, 466-469.
Walensky et al., A stapled BID BH3 helix directly binds and activates BAX. (2006) Mol Cell 24:199-210.
Walensky, et al. Activation of apoptosis in vivo by a hydrocarbon-stapled BH3 helix. Science. 2004;305(5689):1466-1470.
Walter et al., Critical role for IL-13 in the development of allergen-induced airway hyperreactivity. J Immunol. Oct. 15, 2001;167(8):4668-75.
Wang, 4-Alkyl-2-trichloromethyloxazolidin-5-ones: Valuable Precursors to Enantiomerically Pure C- and N-Protected a-Alkyl Prolines. Synlett. 1999;1:33-36.
Wang, et al. (2011). Fine-tuning p53 activity through C-terminal modification significantly contributes to HSC homeostasis and mouse radiosensitivity. Genes Dev 25, 1426-1438.
Wang, et al. BID: a novel BH3 domain-only death agonist. Genes Dev. Nov. 15, 1996;10(22):2859-69.
Wang, et al. Inhibition of HIV-1 fusion 1-15 by hydrogen-bond-surrogate-based alpha helices. Angewandte Chemie International Edition. 2008; 47(10)1879-1882.
Wang et al., Inhibition of p53 degradation by Mdm2 acetylation. FEBS Lett. Mar. 12, 2004;561(1-3):195-201.
Wang et al., "Recognition of a Protein Receptor with the Hydrogen Bond Surrogate-based Artificial Alpha-helices," American Chemical Society Meeting, San Diego (Mar. 2005) (poster).
Wang et al., "Recognition of a Protein Receptor with the Hydrogen Bond Surrogate-based Artificial Alpha-helices," Chemical Biology Symposium, Hunter College (Jan. 2005) (poster).
Weaver et al.,Transition metal-catalyzed decarboxylative allylation and benzylation reactions.Chemical Rev. Mar. 9, 2011;111(3):1846-913.
Website: http://www.onelook.com/?w=span&ls=a&loc=home_ac_span, 1 page, Retrieved on Jan. 23, 2016.
Wei et al., Disorder and structure in the RabII binding domain of RabII family interacting protein 2. Biochemistry. Jan. 27, 2009;48(3):549-57. doi: 10.1021/bi8020197.
Weng et al., Activating mutations of NOTCH1 in human T cell acute lymphoblastic leukemia. Science. Oct. 8, 2004;306(5694):269-71.
Weng et al., Growth suppression of pre-T acute lymphoblastic leukemia cells by inhibition of notch signaling. Mol Cell Biol. Jan. 2003;23(2):655-64.
Wenninger, et al. International Cosmetic Ingredient Dictionary and Handbook. vol. 2, 7th Edition, 1997, published by the Cosmetic, Toiletry, and Fragrance Association.
Westhoff et al., Alterations of the Notch pathway in lung cancer. Proc Natl Acad Sci U S A. Dec. 29, 2009;106(52):22293-8. doi: 10.1073/pnas.0907781106. Epub Dec. 10, 2009.
Wikipedia the Free Encyclopedia. Willgerodt Rearrangement. Available at https://en.wikipedia.org/wiki/Willgerodt_rearrangement. Accessed on Feb. 12, 2013.
Wilen et al., Strategies in Optical Resolution. Tetrahedron. 1977;33:2725-36.
Williams et al., Asymmetric synthesis of 2,6-diamino-6-(hydroxymethyl)pimelic acid: assignment of stereochemistry. J Am Chem Soc. 1991;113(18):6976-6981.

(56) References Cited

OTHER PUBLICATIONS

Wills-Karp et al., Interleukin-13: central mediator of allergic asthma. Science. Dec. 18, 1998;282(5397):2258-61.

Wills-Karp, Interleukin-13 in asthma pathogenesis. Immunol Rev. Dec. 2004;202:175-90.

Wills-Karp, The gene encoding interleukin-13: a susceptibility locus for asthma and related traits. Respir Res. 2000;1(1):19-23. Epub Jul. 17, 2000.

Wilson et al., Crystal structure of the CSL-Notch-Mastermind ternary complex bound to DNA. Cell. Mar. 10, 2006;124(5):985-96.

Wilson et al., The FIP3-RabII protein complex regulates recycling endosome targeting to the cleavage furrow during late cytokinesis. Mol Biol Cell. Feb. 2005;16(2):849-60. Epub Dec. 15, 2004.

Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.

Wu et al., MAML1, a human homologue of *Drosophila* mastermind, is a transcriptional co-activator for NOTCH receptors. Nat Genet. Dec. 2000;26(4):484-9.

Wu et al., Therapeutic antibody targeting of individual Notch receptors. Nature. Apr. 15, 2010;464(7291):1052-7. doi: 10.1038/nature08878.

Wuts, et al. Protective Groups in Organic Synthesis. 2nd Ed., John Wiley and Songs (1991).

Xi et al., Use of DNA and peptide nucleic acid molecular beacons for detection and quantification of rRNA in solution and in whole cells. Appl Environ Microbiol. Sep. 2003;69(9):5673-8.

Xing, et al. Crystal structure of a beta-catenin/axin complex suggests a mechanism for the beta¬catenin destruction complex. Genes Dev. Nov. 15, 2003;17(22):2753-64. Epub Nov. 4, 2003.

Xiong, et al. (2010). Spontaneous tumorigenesis in mice overexpressing the p53-negative regulator Mdm4. Cancer Res 70, 7148-7154.

Yang, et al. Calculation of protein conformation from circular dichroism. Methods Enzymol. 1986;130:208-69.

Yang et al. Synthesis and helical structure of lactam bridged BH3 peptides derived from pro-apoptotic Bcl-2 family proteins. Bioorg Med Chem Lett. Mar. 22, 2004;14(6):1403-6.

Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.

Ye et al., Neurogenic phenotypes and altered Notch processing in *Drosophila presenilin* mutants. Nature. Apr. 8, 1999;398(6727):525-9.

Yee, et al. Efficient large-scale synthesis of BILN 2061, a potent HCV protease inhibitor, by a convergent approach based on ring-closing metathesis. J Org Chem. Sep. 15, 2006;71(19):7133-45.

Yin et al., "Terphenyl-based Helical Mimetics That Disrupt the p53/HDM2 Interaction," Angew. Chem. Int. Ed. 44:2704-2707 (2005).

Yu, et al. Synthesis of macrocyclic natural products by catalyst-controlled stereoselective ring-closing metathesis. Nature. Nov. 2, 2011;479(7371):88-93. doi: 10.1038/nature10563.

Yu et al., The role of Axing in calvarial morphogenesis and craniosynostosis. Development. Apr. 2005; 132(8): 1995-2005.

Zeisig, et al. (2012). SnapShot: Acute myeloid leukemia. Cancer Cell 22, 698-698 e691.

Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.

Zhang, et al. A triazole-templated ring-closing metathesis for constructing novel fused and bridged triazoles. Chem Commun (Camb). Jun. 21, 2007;(23):2420-2.

Zhang, et al. Development of a High-throughput Fluorescence Polarization Assay for Bcl-xL. Anal. Biochem. 2002; 307:70-75.

Zhang, et al. Ruthenium-catalyzed cycloaddition of alkynes and organic azides. J Am Chem Soc. Nov. 23, 2005;127(46):15998-9.

Zhang, et al. Targeting p53-MDM2-MDMX loop for cancer therapy. Subcell Biochem. 2014;85:281-319. doi: 10.1007/978-94-017-9211-0_16.

Zhao, et al. (2010). p53 loss promotes acute myeloid leukemia by enabling aberrant self-renewal. Genes Dev 24, 1389-1402.

Zhao, et al. (2015). Small-molecule inhibitors of the MDM2-p53 protein-protein interaction (MDM2 Inhibitors) in clinical trials for cancer treatment. J Med Chem 58, 1038-1052.

Zhou, et al. Identification of ubiquitin target proteins using cell-based arrays. J Proteome Res. 2007; 6:4397-4406.

Zhou et al., Lymphoid enhancer factor 1 directs hair follicle patterning and epithelial cell fate. Genes Dev. Mar. 15, 1995;9(6):700-13.

Zhou et aL, Tyrosine kinase inhibitor STI-571/Gleevec down-regulates the beta-catenin signaling activity. Cancer Lett. Apr. 25, 2003;193(2):161-70.

Zimm & Bragg, "Theory of the Phase Transition between Helix and Random Coil in Polypeptide Chains," J. Chem. Phys. 31(2):526-535 (1959).

Zitzow, et al. Pathogenesis of avian influenza A (H5N1) viruses in ferrets. J Virol. May 2002;76(9):4420-9.

Zor et aL, Solution structure of the KIX domain of CBP bound to the transactivation domain of c-Myb. J Mol Biol. Mar. 26, 2004;337(3):521-34.

\* cited by examiner

Column Used: Chiralpak AD-H QC#167
Vial: 73  Injection: 1
Injection Volume: 5.00 ul
Sample Concentration: 48.0mg/25mL DS
Additional Sample Information: Finished Product
Solvent A: 90%Hex.anes/10%IPA/0.1%TFA
Solvent B: 90%Hex.anes/10%IPA
Solvent C: IPA
Solvent C: EtOH

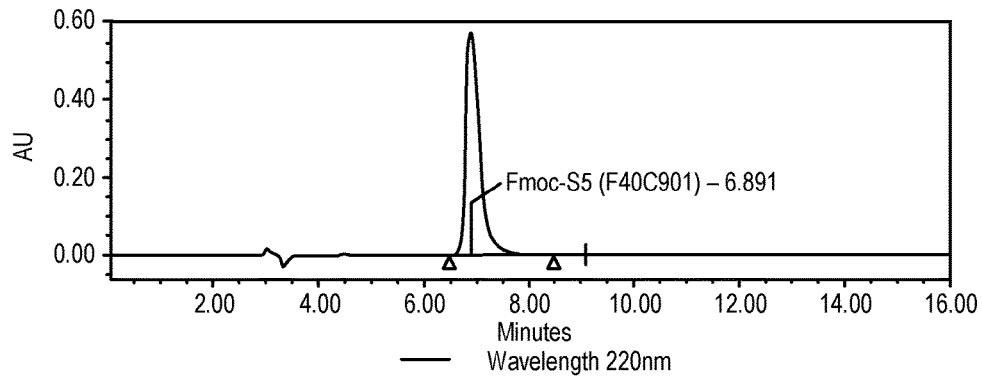

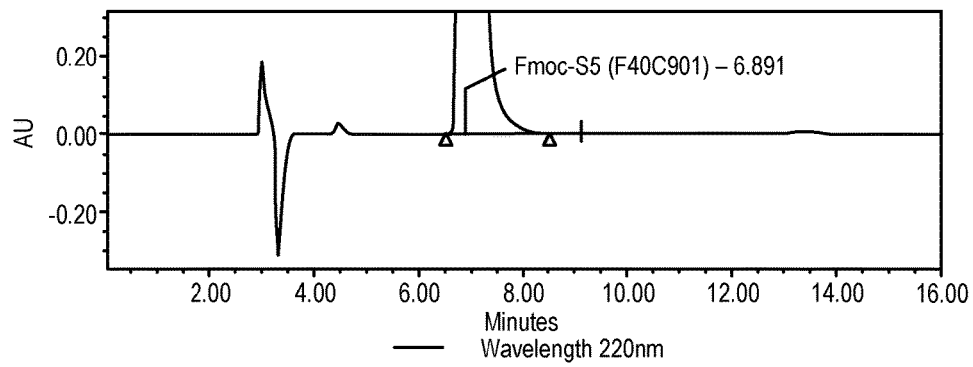

Results processed by 220nm

| | Peak Name | Retention Time | Peak Area | % Peak Area | | Peak Name | Retention Time | Peak Area | % Peak Area |
|---|---|---|---|---|---|---|---|---|---|
| 1 | Fmoc-S5 (F40C901) | 6.891 | 9858806 | 100.00 | 2 | Fmoc-S5 (F40C902) | 9.100 | | |

User Name: System  Current Date: 12/19/2011 2:19:54 PM

*FIG. 1*

Column Used: Chiralpak AD-H QC#167
Vial: 74 Injection: 1
Injection Volume: 5.00 ul
Sample Concentration: 48.0mg/25mL DS + 0.5% R5
Additional Sample Information: Sample+0.5% R5

Solvent A: 90%Hex.anes/10%IPA/0.1%TFA
Solvent B: 90%Hex.anes/10%IPA
Solvent C: IPA
Solvent C: EtOH

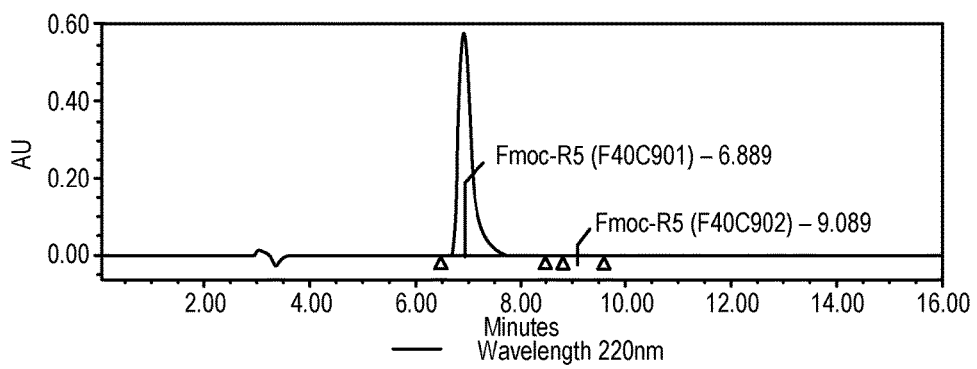

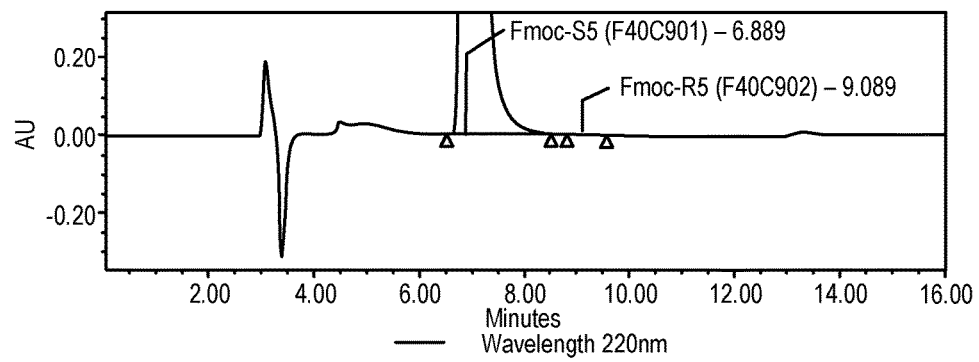

Results processed by 220nm

| | Peak Name | Retention Time | Peak Area | % Peak Area | | Peak Name | Retention Time | Peak Area | % Peak Area |
|---|---|---|---|---|---|---|---|---|---|
| 1 | Fmoc-55 (F40C901) | 6.889 | 9847318 | 99.83 | 2 | Fmoc-55 (F40C902) | 9.089 | 16328 | 0.17 |

User Name: System          Current Date: 12/19/2011 2:41:41 PM          1 of 1

*FIG. 2*

Column Used: Waters Spherisorb ODS2#131  Date Acquired: 12/20/2011 1:53:06 PM
Vial: 35  Injection: 1  Processing Method F40C902_60to80in25min
Injection Volume: 5.00 ul  Date Processed: 12/20/2011 3:19:31 PM
Sample Concentration: 26.1mg/25mL DS
Additional Sample Information: Sample Data from Chromatogram 254nm

|   | Peak Name | Retention Time | Height (µV) | % Height | Peak Area | % Peak Area |
|---|---|---|---|---|---|---|
| 1 |   | 3.083 | 914 | 0.13 | 5380 | 0.06 |
| 2 |   | 3.626 | 379 | 0.05 | 2548 | 0.03 |
| 3 |   | 3.858 | 612 | 0.09 | 7057 | 0.08 |
| 4 |   | 4.852 | 2303 | 0.32 | 17314 | 0.19 |
| 5 |   | 5.484 | 967 | 0.14 | 8412 | 0.09 |
| 6 |   | 6.206 | 2206 | 0.31 | 20714 | 0.23 |
| 7 |   | 9.411 | 1420 | 0.20 | 14463 | 0.16 |
| 8 | F40C902 | 10.054 | 698574 | 98.50 | 8845126 | 98.36 |
| 9 |   | 11.195 | 1818 | 0.26 | 71822 | 0.80 |

Column Used: Waters Spherisorb ODS2 #131  
Vial: 36   Injection: 1  
Injection Volume: 5.00 ul  
Sample Concentration: 0.5mg/25mL DS  
Additional Sample Information: Customer Control Date Acquired: 12/20/2011 2:44:05 PM  
Processing Method F40C902_60to80in25min  
Date Processed: 12/20/2011 3:24:26 PM Data from Chromatogram 215nm

|   | Peak Name | Retention Time | Height (µV) | % Height | Peak Area | % Peak Area |
|---|-----------|----------------|-------------|----------|-----------|-------------|
| 1 | F40C902   | 10.086         | 273598      | 100.00   | 3562385   | 100.05      |

Column Used: CHiralpak AD-H QC#167
Vial: 86  Injection: 1
Injection Volume: 20.00 ul
Sample Concentration: 25.5mg (N2 Dried)/25mL IPA
Additional Sample Information:
N-Fmoc-(R)-a-Me-a-Aminodec-9-Enoic Acid; Sample; 100%
MP-A; 1.0mL/min; 25 C; 730 psi;

Solvent A: 90%Hexanes/10%IPA/0.1%TFA
Solvent B: 90%Hexanes/10%IPA
Solvent C: IPA
Solvent D: EtOH

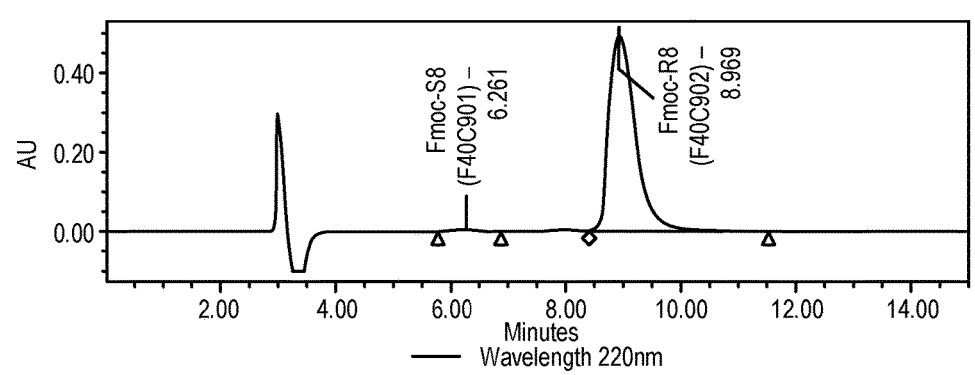

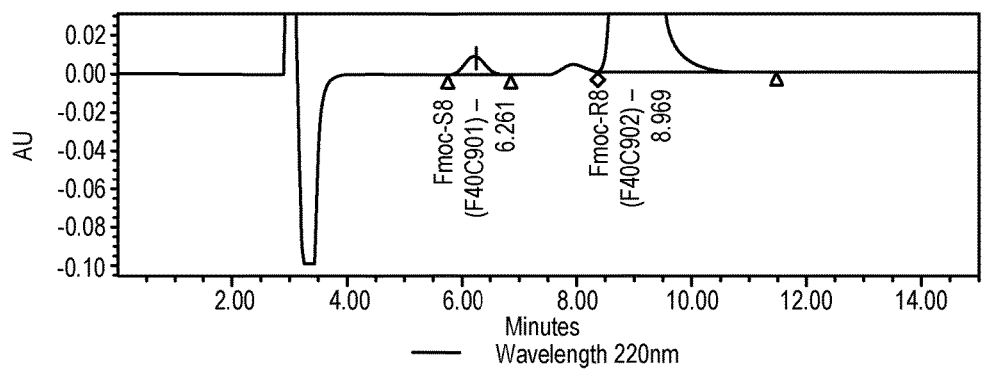

Results processed by 220nm

| | Peak Name | Retention Time | Peak Area | % Peak Area | | Peak Name | Retention Time | Peak Area | % Peak Area |
|---|---|---|---|---|---|---|---|---|---|
| 1 | Fmoc-S8 (F40C901) | 6.261 | 215326 | 1.37 | 2 | Fmoc-S8 (F40C902) | 8.969 | 15530958 | 98.63 |

*FIG. 6*

Column Used: Waters Spherisorb ODS2 #131
Vial: 46   Injection: 1
Injection Volume: 5.00 ul Date Processed: 11/16/2011 7:19:45 PM
Processing Method F40C902_60to80in25min
Date Processed: 11/17/2011 4:04:32 PM Sample Concentration: 14.6mg/10mL DS Additional Sample Information: N-Fmoc-(R)-a-Me-a-
    Aminodec-9-enoic Acid; FP;

|   | Peak Name | Retention Time | Height (μV) | % Height | Peak Area | % Peak Area |
|---|-----------|----------------|-------------|----------|-----------|-------------|
| 1 | Fmoc-OnSu | 8.800          |             |          |           |             |
| 2 |           | 15.504         | 494         | 0.04     | 9432      | 0.05        |
| 3 | 40C902    | 16.100         |             |          |           |             |
| 4 |           | 16.149         | 1013        | 0.09     | 13695     | 0.08        |
| 5 | F40C902   | 18.334         | 1106791     | 99.81    | 17679588  | 99.82       |
| 6 |           | 25.283         | 552         | 0.05     | 8025      | 0.05        |

Column Used: Waters Spherisorb ODS2 #131
Vial: 46   Injection: 1
Injection Volume: 5.00 ul
Sample Concentration: 14.6mg/10mL DS
Additional Sample Information:
N-Fmoc-(R)-a-Me-a-Aminodec-9-enoic Acid; FP;

Date Acquired: 11/16/2011 7:19:45 PM
Processing Method F40C902_60to80in25min
Date Processed: 11/17/2011 6:11:21 PM Data from Chromatogram 254nm

|   | Peak Name | Retention Time | Height (µV) | % Height | Peak Area | % Peak Area |
|---|---|---|---|---|---|---|
| 1 | Fmoc-OnSu | 8.800 | | | | |
| 2 | 40C902 | 16.100 | | | | |
| 3 | F40C902 | 18.334 | 856815 | 99.96 | 13404558 | 99.95 |
| 4 | | 25.289 | 382 | 0.04 | 7053 | 0.05 |

DISUBSTITUTED AMINO ACIDS AND METHODS OF PREPARATION AND USE THEREOF

CROSS-REFERENCE

This application is a continuation application of U.S. Utility application Ser. No. 14/070,306, filed Nov. 1, 2013, now U.S. Pat. No. 9,604,919, which claims the benefit of U.S. Provisional Application No. 61/721,457, filed Nov. 1, 2012, and U.S. Provisional Application No. 61/799,917, filed Mar. 15, 2013, each of which is incorporated herein by reference in its entirety.

BACKGROUND OF THE INVENTION

α, α-Disubstituted amino acids bearing a terminal alkene on one of their side chains and their salts ("alkene α, α-disubstituted amino acids") are useful for making cross-linked macrocyclic peptides. For example, International Application No. PCT/US2004/038403 ("the '403 application") discloses incorporating into a peptide two α, α-disubstituted amino acids that each contain a side-chain bearing a terminal alkene, and cross-linking the terminal alkene groups to form a cross-linked ("stapled") macrocyclic peptide. The cross-link can, for example, stabilize a secondary structure (e.g., an α-helix) present in the stapled macrocyclic peptide.

International Application Publication No. WO2008/121767 ("the '767 publication") discloses using alkene α, α-disubstituted amino acids to form stitched polypeptides (e.g., multiple and tandem crosslinked polypeptides) having secondary structures stabilized by stitching. The '403 application, the '767 publication, and other applications, publications, and patents, disclose that stapled and stitched macrocyclic peptides are useful for treating and preventing various diseases including cancer.

Alkene α, α-disubstituted amino acids are thus important and useful building blocks for forming stitched and stapled polypeptides and their precursors. The use of alkene α, α-disubstituted amino acids, however, has been limited by an inability to provide these important molecules in crystalline form. For example, commercially available preparations of alkene α, α-disubstituted amino acids are typically sold as pre-made solutions. The pre-made solutions limit the amount of α, α-disubstituted amino acid that can be shipped per unit volume, limit the chemical reactions that are available to be run with the alkene α, α-disubstituted amino acids, subject the alkene α, α-disubstituted amino acids to an enhanced degradation rate, and are environmentally unfriendly. Thus, there remains a compelling need for crystalline alkene α, α-disubstituted amino acids and their crystalline salts, and processes for producing and using these crystalline amino acids.

In addition, substituting one or more hydrogen atoms of an alkene α, α-disubstituted amino acid with deuterium or a halogen atom can change one or more of the amino acid's properties. For example dipole moment, hydrophobicity, hydrophilicity, steric bulk, or reactivity of an alkene α, α-disubstituted amino acid can be changed by substituting one or more hydrogen atoms thereon with one or more deuterium or halogen atoms. Thus, there also remains a need for optionally crystalline alkene α, α-disubstituted amino acids and their optionally crystalline salts having one or more hydrogen atoms thereon substituted with deuterium or halogen, and methods of making and using these.

SUMMARY OF THE INVENTION

The above needs, and others, are addressed herein. The inventive embodiments provided in this Summary of the Invention are meant to be illustrative only and to provide an overview of selected inventive embodiments disclosed herein. The Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

Provided herein are crystalline compounds of Formula (I) and crystalline salts thereof:

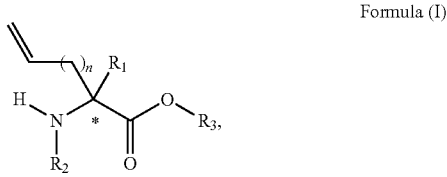

Formula (I)

wherein $R_1$ is $C_1$-$C_3$ alkyl, $C_1$-$C_3$ deuteroalkyl, or $C_1$-$C_3$ haloalkyl; * is a stereocenter; n is an integer from 1 to 20; $R_2$ is —H or a nitrogen protecting group; and $R_3$ is —H or a protecting or activating group.

Also provided herein are methods of preparing a polypeptide, comprising making the polypeptide with one or more crystalline compounds of Formula (I) or their crystalline salts.

Further provided herein are methods of making crystalline compounds of Formula (I) or their crystalline salts, comprising at least one of the following purifications:

1) Crystallizing a metal complex of Formula (XIb)

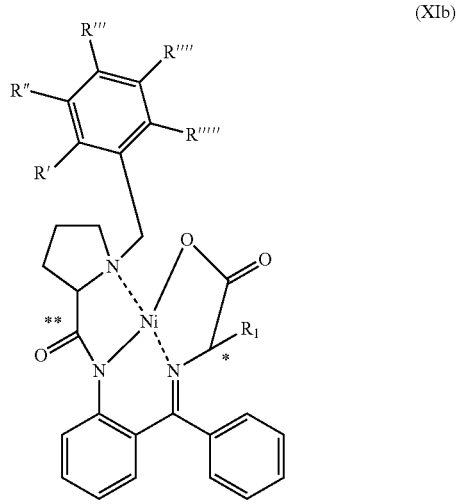

(XIb)

from one or more solvents, optionally a cyclic ether, optionally tetrahydrofuran and methyl tert-butyl ether, or optionally an alcohol, optionally isopropyl alcohol, optionally an ester, optionally isopropyl acetate, optionally ethyl acetate, wherein $R_1$ is $C_1$-$C_3$ alkyl, $C_1$-$C_3$ deuteroalkyl, or $C_1$-$C_3$ haloalkyl, * and ** are each independently stereocenters, and R', R", R''', R'''', and R''''' are, in the order going around the aromatic ring from R' to R''''', selected from H, H, Cl, Cl, H;
F, F, F, F, F;
F, F, OiPr, F, F;
F, F, OMe, F, F;
Cl, H, H, H, H; or
H, H, Me, Me, H;

2) Precipitating a compound of Formula (Ia) as its HCl salt:

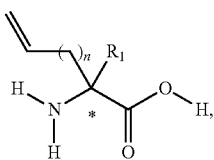

Formula (Ia)

wherein $R_1$ is $C_1$-$C_3$ alkyl, $C_1$-$C_3$ deuteroalkyl, or $C_1$-$C_3$ haloalkyl, n is an integer from 1 to 20, and * is a stereocenter;

3) Forming an addition salt of Formula (XIVb):

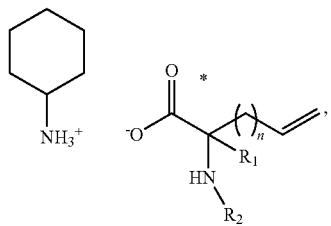

Formula (XIVb)

wherein $R_1$ is $C_1$-$C_3$ alkyl, $C_1$-$C_3$ deuteroalkyl, or $C_1$-$C_3$ haloalkyl, $R_2$ is a nitrogen protecting group, n is an integer from 1 to 20, and * is a stereocenter; or 4) Crystallizing a compound of Formula (I) or a salt thereof from one or more solvents, optionally chloroform and hexanes.

In some embodiments, the compound of Formula (XIb) is crystallized in a mixture of tetrahydrofuran and methyl t-butyl ether. In some embodiments, the ratio of tetrahydrofuran and methyl t-butyl ether is between: 1:10 and 3:10. For example, the ratio is 1.5:10.

In some embodiments, the compound of Formula (I) or a salt thereof is crystallized in a mixture of chloroform and hexanes. In some embodiments, the ratio of chloroform to hexanes is between 1:5 and 1:1. For example, the ratio is 1:3 or 1:2. Also provided herein are methods of preparing a polypeptide, comprising making the polypeptide with one or more crystalline compounds of Formula (I) or their crystalline salts.

BRIEF DESCRIPTION OF THE DRAWINGS

FIG. 1 is a chiral HPLC trace of N-Fmoc-(S)-alpha-methyl-alpha-amino-6-enoic acid.

FIG. 2 is a chiral HPLC trace of N-Fmoc-(S)-alpha-methyl-alpha-amino-6-enoic acid spiked with N-Fmoc-(R)-alpha-methyl-alpha-amino-6-enoic acid.

FIG. 6 is a chiral HPLC trace of N-Fmoc-(R)-alpha-methyl-alpha-aminodec-9-enoic acid.

INCORPORATION BY REFERENCE

Figure 3:
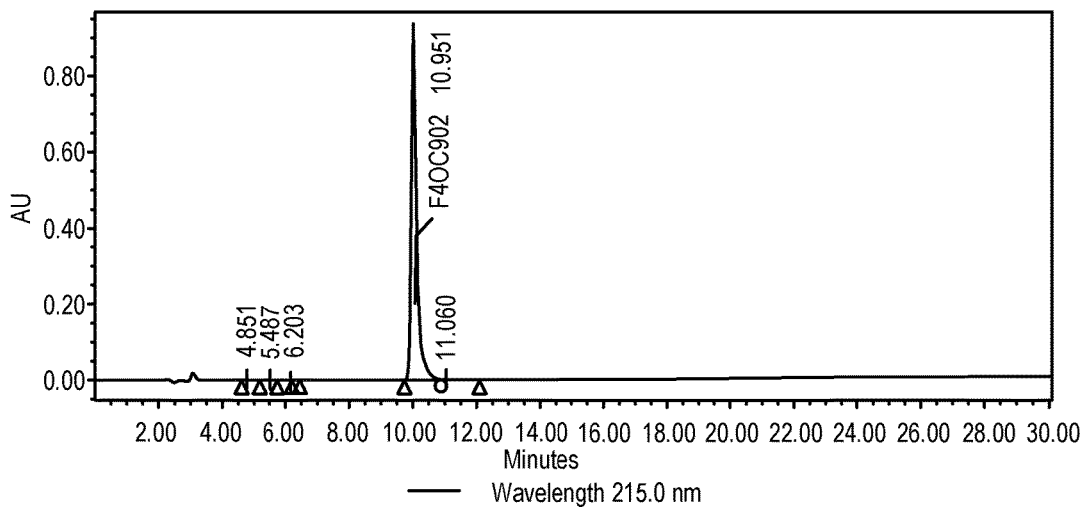
FIG. 3 is an HPLC trace of N-Fmoc-(S)-alpha-methyl-alpha-amino-6-enoic acid with the detector set to 215 nm.
Figure 4:
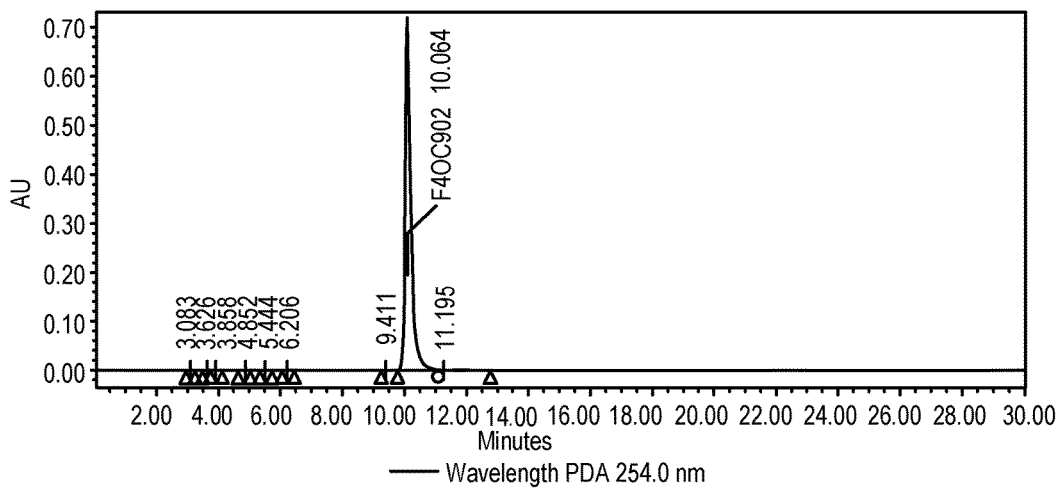
FIG. 4 is an HPLC trace of N-Fmoc-(S)-alpha-methyl-alpha-amino-6-enoic acid with the detector set to 254 nm.
Figure 5:
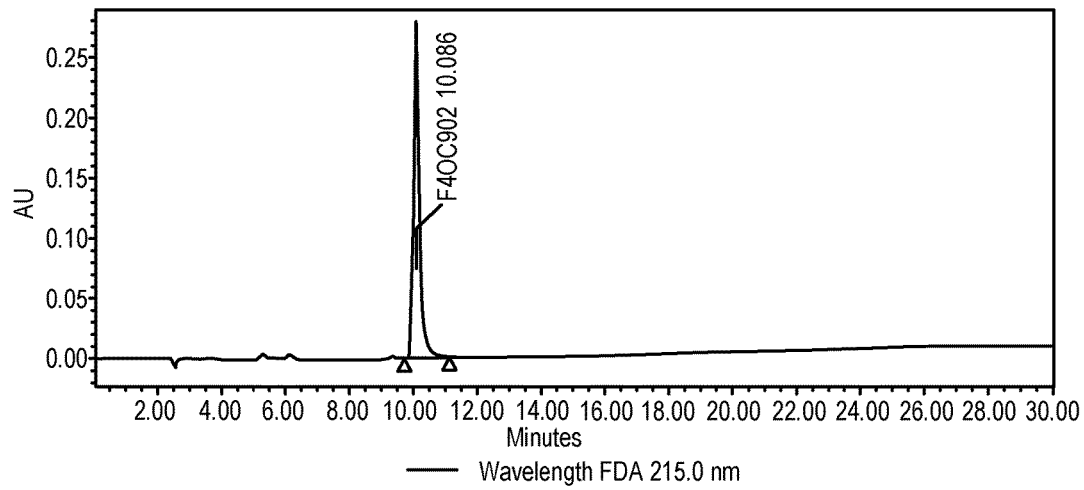
FIG. 5 is an HPLC trace of an N-Fmoc-(S)-alpha-methyl-alpha-amino-6-enoic acid standard.
Figure 7:
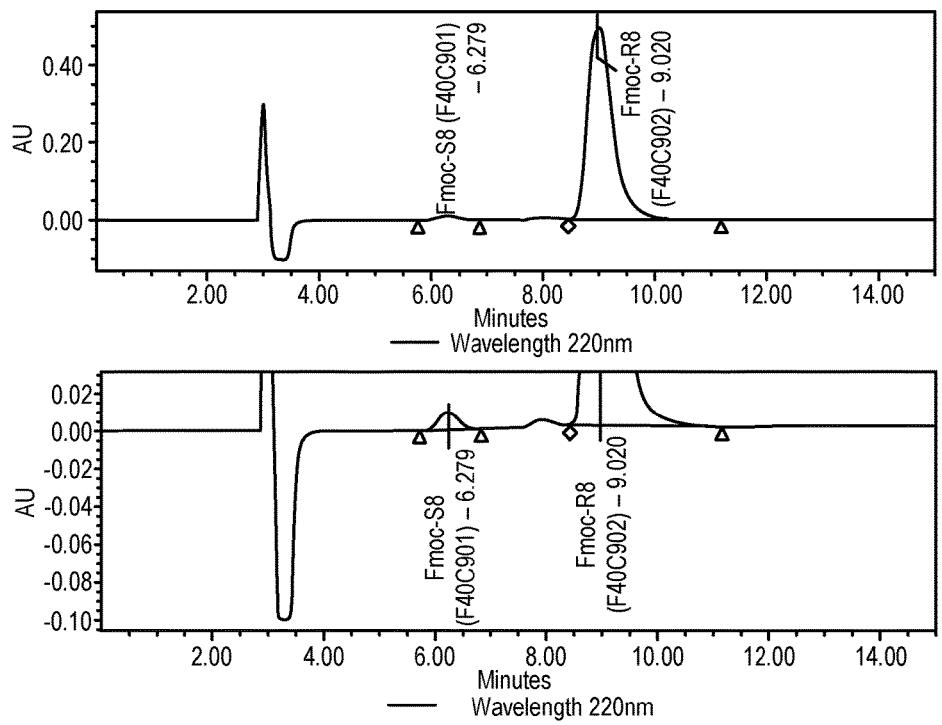
FIG. 7 is a chiral HPLC trace of N-Fmoc-(R)-alpha-methyl-alpha-aminodec-9-enoic acid spiked with N-Fmoc-(S)-alpha-methyl-alpha-aminodec-9-enoic acid.
Figure 8:
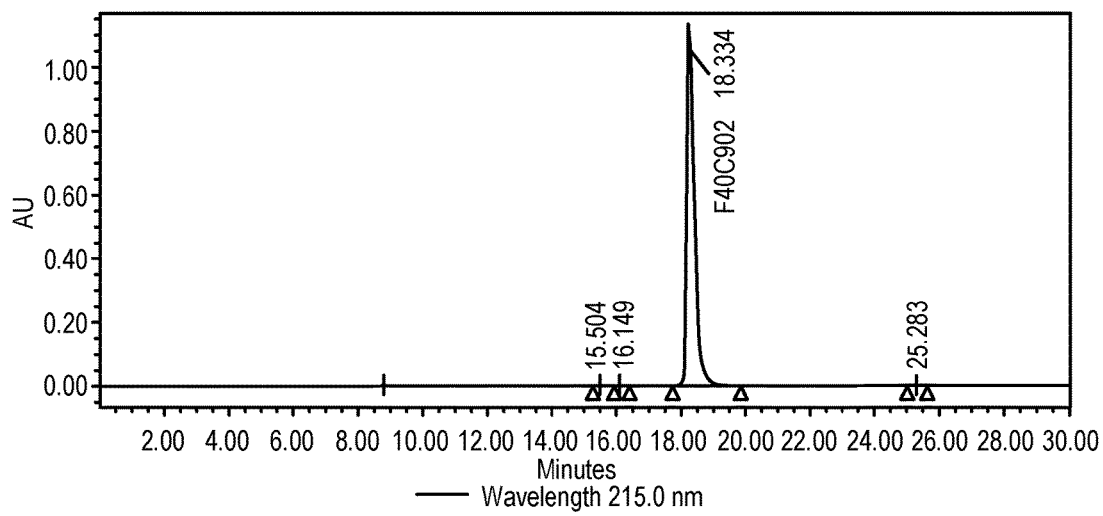
FIG. 8 is an HPLC trace of N-Fmoc-(R)-alpha-methyl-alpha-aminodec-9-enoic acid with the detector set to 215 nm.
Figure 9:
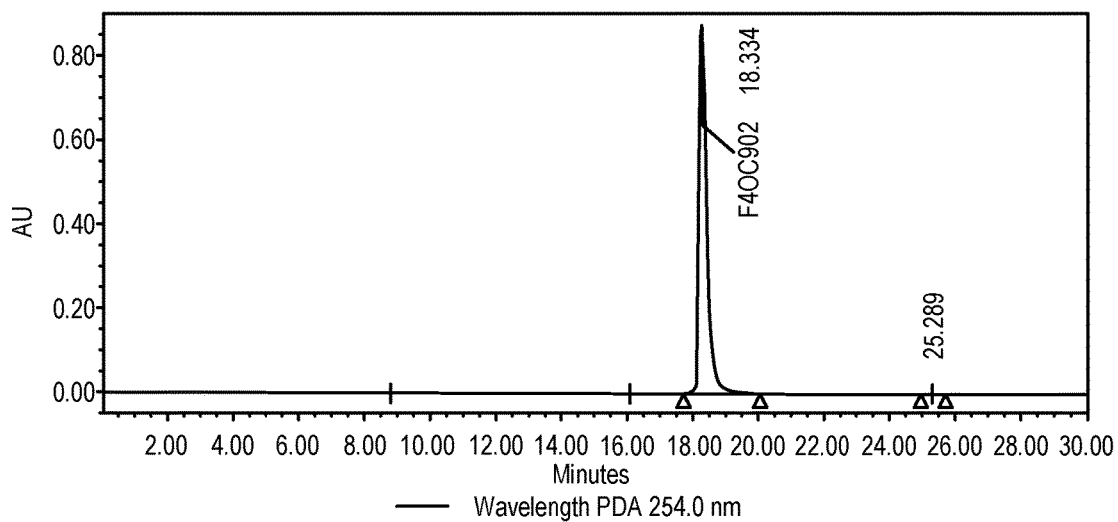
FIG. 9 is an HPLC trace of N-Fmoc-(R)-alpha-methyl-alpha-aminodec-9-enoic acid with the detector set to 254 nm.

All publications, patents, and patent applications referenced herein are incorporated by reference in their entireties. In the event of a conflict between a term herein and a term incorporated by reference, the term herein controls.

DETAILED DESCRIPTION OF THE INVENTION

The details of one or more inventive embodiments are set forth in the accompanying drawings, the claims, and in the description herein. Other features, objects, and advantages of inventive embodiments disclosed and contemplated herein will be apparent from the description and drawings, and from the claims.

Initial Definitions

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

Herein, unless otherwise indicated, any embodiment can be combined with any other embodiment.

Herein, unless otherwise indicated, some inventive embodiments herein contemplate numerical ranges.

When ranges are present, the ranges include the range endpoints. Additionally, every subrange and value within the range is present as if explicitly written out.

Herein, unless otherwise indicated, the symbol "D" stands for deuterium or a radical thereof.

Herein, unless otherwise indicated, the term "halo" or the term "halogen" each refer to fluorine, chlorine, bromine or iodine, or a radical thereof.

Herein, unless otherwise indicated, the term "alkyl" refers to a hydrocarbon chain that is a straight chain or branched chain, containing the indicated number of carbon atoms. For example, $C_1$-$C_3$ alkyl group indicates that the group has from 1 to 3 (inclusive) carbon atoms in it.

"Deuteroalkyl" refers to a deuterated alkyl chain, where the alkyl chain hydrogen atoms are replaced at least the 90% level with deuterium atoms.

Herein, unless otherwise indicated, the term "haloalkyl" refers to a halogenated alkyl chain where the alkyl chain hydrogen atoms are replaced with halogen atoms. In some embodiments, the halogen atoms are all the same (e.g., all F or all Cl).

Herein, unless otherwise indicated, ⫽ is a double (e.g., alkene) bond.

As used herein, unless otherwise indicated, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycles include embodiments where the macrocycle-forming linker connects an α-carbon of the first amino acid residue (or analog) to the α-carbon of the second amino acid residue (or analog) in the peptide. Peptidomimetic macrocycles include one or more non-peptide bonds between one or more amino acid residues and/or amino acid analog residues, and optionally include one or more non-naturally-occurring amino acid residues or amino acid analog residues in addition to any which form the macrocycle.

As used herein, unless otherwise indicated, a "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, unless otherwise indicated, the term "amino acid" refers to a molecule containing both an amino group and a carboxyl group. Suitable amino acids include, for example, both the D- and L-isomers of the naturally-occurring amino acids, as well as non-naturally occurring amino acids prepared by organic synthesis or other metabolic routes. The term amino acid contemplates, for example, α-amino acids, natural amino acids, non-natural amino acids, and amino acid analogs.

As used herein, unless otherwise indicated, the term "α-amino acid" refers to a molecule containing both an amino group and a carboxyl group bound to a carbon atom which is designated the α-carbon atom.

As used herein, unless otherwise indicated, the term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

Herein, unless otherwise indicated, the term "amino acid side chain" refers to a moiety attached to the α-carbon atom (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

Herein, unless otherwise indicated, the term "α,α di-substituted amino" acid refers to a molecule or moiety containing both an amino group and a carboxyl group bound to a carbon atom (e.g., the α-carbon atom) that is also attached a natural and non-natural, to two natural, or to two non-natural amino acid side chains.

Herein, unless otherwise indicated, the term "polypeptide" can encompass two or more naturally or non-naturally-occurring amino acids joined by a covalent bond (e.g., an amide bond). Polypeptides, as described herein can include full length proteins (e.g., fully processed proteins) as well as shorter amino acid sequences (e.g., fragments of naturally-occurring proteins or synthetic polypeptide fragments).

Herein, unless otherwise indicated, the term "macrocyclization reagent" or "macrocycle-forming reagent" can refer to any reagent which can be used to prepare a peptidomimetic macrocycle by mediating the reaction between two reactive olefinic groups thereon. The reactive groups that, once reacted, close the linker, can be for example terminal olefins (alkenes), deuterated or non-deuterated.

Macrocyclization reagents or macrocycle-forming reagents can be metathesis catalysts including, but not limited to, stabilized, late transition metal carbene complex catalysts such as Group VIII transition metal carbene catalysts. For example, such catalysts can contain Ru and Os metal centers having a +2 oxidation state, an electron count of 16 and pentacoordinated. The catalysts can have W or Mo centers. Various catalysts are disclosed in Grubbs et al., "Ring Closing Metathesis and Related Processes in Organic Synthesis" *Acc. Chem. Res.* 1995, 28, 446-452; U.S. Pat. No. 5,811,515; U.S. Pat. No. 7,932,397; U.S. Pat. Application Pub. No. 2011/0065915; U.S. Pat. Application Pub. No. 2011/0245477; Yu et al., "Synthesis of Macrocyclic Natural Products by Catalyst-Controlled Stereoselective Ring-Closing Metathesis," *Nature* 2011, 479, 88; and Peryshkov et al., "Z-Selective Olefin Metathesis Reactions Promoted by Tungsten Oxo Alkylidene Complexes," *J. Am. Chem. Soc.* 2011, 133, 20754.

Herein, unless otherwise indicated, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Provided herein are crystalline compounds of Formula (I) or their crystalline salts:

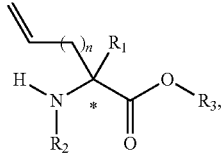

Formula (I)

wherein $R_1$ is $C_1$-$C_3$ alkyl, $C_1$-$C_3$ deuteroalkyl, or $C_1$-$C_3$ haloalkyl; * is a stereocenter; n is an integer from 1 to 20; $R_2$ is —H or a nitrogen protecting group; and $R_3$ is —H or a protecting or activating group.

$R_1$

In the crystalline compound of Formula (I) or its crystalline salt, $R_1$ can be $C_1$-$C_3$ alkyl. $R_1$ can be, for example, methyl, ethyl, n-propyl, or isopropyl.

In the crystalline compound of Formula (I) or its crystalline salt, $R_1$ can be $C_1$-$C_3$ deuteroalkyl. $R_1$ can be, for example, —$CD_3$, —$CD_2CD_3$, —$CD_2CD_2CD_3$, or —$CD(CD_3)_2$.

In the crystalline compound of Formula (I) or its crystalline salt, $R_1$ can be $C_1$-$C_3$ haloalkyl. The halogen can be, for example, —F, —Cl, —Br, or —I. $R_1$ can be, for example, —$CX_3$, —$CX_2CX_3$, —$CX_2CX_2CX_3$, or —$CX(CX_3)_2$, wherein X is a halogen.

$R_2$

In the crystalline compound of Formula (I) or its crystalline salt, $R_2$ can be, for example, —H, or a nitrogen protecting group selected from the group consisting of: 9-Fluorenylmethoxycarbonyl (Fmoc), Trityl (Trt), 4-Methoxytrityl (Mmt), 2-(3,5-Dimethoxyphenyl)propan-2-yloxycarbonyl (Ddz), 2-(p-Biphenylyl)-2-propyloxycarbonyl (Bpoc), 2-(4-Nitrophenylsulfonyl)ethoxycarbonyl (NSC), (1,1-Dioxobenzo[b]thiophene-2-yl)methyloxycarbonyl (Bsmoc), (1,1-Dioxonaphtho[1,2-b]thiophene-2-yl)methyloxycarbonyl (α-Nsmoc), 1-(4,4-dimethyl-2,6-dioxocyclohex-1-ylidene)-3-methylbutyl (ivDde), 2,-Di-tert-butyl-Fmoc (Fmoc*), 2-Fluoro-Fmoc (Fmoc(2F)), 2-Monoisooctyl-Fmoc (mio-Fmoc), 2,7-Diisooctyl-Fmoc (dio-Fmoc), 2-[Phenyl(methyl)sulfonio]ethyloxy carbonyl tetrafluoroborate (Pms), Ethanesulfonylethoxycarbonyl (Esc), 2-(4-Sulfophynylsulfonyl)ethoxy carbonyl (Sps), Tert-butyloxycarbonyl (Boc), Benzyloxycarbonyl (Z), Allyloxycarbonyl (Alloc), 2,2,2-Trichloroethyloxycarbonyl (Troc), p-Nitrobenzyloxycarbonyl (pNZ), Propargyloxycarbonyl (Poc), o-Nitrobenzenesulfonyl (oNBS), 2,4-Dinitrobenzenesulfonyl (dNBS), Benzothiazole-2-sulfonyl (Bts), o-Nitrobenzyloxycarbonyl (oNz), 4-Nitroveratryloxycarbonyl (NVCO), 2-(2-Nitrophenyl)propyloxycarbonyl (NPPOC), 2,(3, 4-Methylethenedioxy-6-nitrophenyl)propyloxycarbonyl (MNPPOC), 9-(4-Bromophenyl)-9-fluorenyl (BrPhF), Azidomethoxycarbonyl (Azoc), Hexafluoroacetone (HFA), 2-Chlorobenzyloxycarbonyl (Cl-Z), 4-Methyltrityl (Mtt), Trifluoroacetyl (tfa), (Methylsulfonyl)ethoxycarbonyl (Msc), Phenyldisulphanylethyloxycarbonyl (Phdec), 2-Pyridyldisulphanylethyloxycarbonyl (Pydec), and o-Nitrobenzenesulfonyl (O-NBS).

Nitrogen protecting groups can be found, for example, in Isidro-Llobet, A., et al., "Amino Acid-Protecting Groups," *Chem. Rev.* 2455-2504 (2009).

In the crystalline compound of Formula (I) or its crystalline salt, $R_2$ can be, for example, a nitrogen protecting group selected from the group consisting of 9-Fluorenylmethoxycarbonyl (Fmoc), Trityl (Trt), 4-Methoxytrityl (Mmt), 2-(3, 5-dimethoxyphenyl)propan-2-yloxycarbonyl (Ddz), 2-(p-biphenylyl)-2-propyloxycarbonyl (Bpoc), 2-(4-Nitrophenylsulfonyl)ethoxycarbonyl (NSC), 1,1-Dioxobenzo[b]thiophene-2-yl)methyloxycarbonyl (Bsmoc), 1-(4,4-dimethyl-2,6-dioxocyclohex-1-ylidene)-3-methylbutyl (ivDde), Tert-butyloxycarbonyl (Boc), Benzyloxycarbonyl (Z), Allyloxycarbonyl (Alloc), 2,2,2-Trichloroethyloxycarbonyl (Troc), p-Nitrobenzyloxycarbonyl (pNZ), o-Nitrobenzenesulfonyl (oNBS), 2,4-Dinitrobenzenesulfonyl (dNBS), o-Nitrobenzyloxycarbonyl (oNz), 4-Nitroveratryloxycarbonyl (NVCO), 2-(2-Nitrophenyl)propyloxycarbonyl (NPPOC), Hexafluoroacetone (HFA), 2-Chlorobenzyloxycarbonyl (Cl-Z), 4-Methyltrityl (Mtt), Trifluoroacetyl (tfa), (Methylsulfonyl)ethoxycarbonyl (Msc), and o-Nitrobenzenesulfonyl (O-NBS).

In the crystalline compound of Formula (I) or its crystalline salt, $R_2$ can be a nitrogen protecting group selected from the group consisting of 9-Fluorenylmethoxycarbonyl (Fmoc), Trityl (Trt), 4-Methoxytrityl (Mmt), 2-(3,5-dimethoxyphenyl)propan-2-yloxycarbonyl (Ddz), 2-(p-biphenylyl)-2-propyloxycarbonyl (Bpoc), Tert-butyloxycarbonyl (Boc), Benzyloxycarbonyl (Z), Allyloxycarbonyl (Alloc), 2,2,2-Trichloroethyloxycarbonyl (Troc), o-Nitrobenzenesulfonyl (oNBS), Trityl (Trt), 4-Methyltrityl (Mtt), and o-Nitrobenzenesulfonyl (O-NBS).

In the crystalline compound of Formula (I) or its crystalline salt, $R_2$ can be, for example, the nitrogen protecting group 9-Fluorenylmethoxycarbonyl (Fmoc).

$R_3$

In the crystalline compound of Formula (I) or its crystalline salt, $R_3$ can be, for example, —H or a protecting or activating group selected from the group consisting of: tert-Butyl (tBu), 2-Chlorotrityl (2-Cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentaflurophenyl, and 2, 4, 5-trichlorophenyl.

In the crystalline compound of Formula (I) or its crystalline salt, $R_3$ can be, for example —H.

n

In the crystalline compound of Formula (I) or its crystalline salt, n can range, for example, from 1-20, from 3-11, or from 3-6. n can be, for example 3 or 6 or 11. n can be 3. n can be 6. n can be 11.

*

In the crystalline compound of Formula (I) or its crystalline salt, the stereocenter * can be (R). In the crystalline compound of Formula (I) or its crystalline salt, the stereocenter * can be (S).

In one embodiment, in the crystalline compound of Formula (I) or it crystalline salt, $R_1$ can be $C_1$-$C_3$ alkyl; $R_2$ can be 9-Fluorenylmethoxycarbonyl (Fmoc); $R_3$ can be selected from the group consisting of —H tert-Butyl (tBu), 2-Chlorotrityl (2-Cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentaflurophenyl, and 2, 4, 5-trichlorophenyl; n can be an integer ranging from 3 to 11; and the stereocenter * can be (R).

In one embodiment, in the crystalline compound of Formula (I) or it crystalline salt, $R_1$ can be $C_1$-$C_3$ alkyl; $R_2$ can be 9-Fluorenylmethoxycarbonyl (Fmoc); $R_3$ can be selected from the group consisting of —H tert-Butyl (tBu), 2-Chlorotrityl (2-Cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentaflurophenyl, and 2, 4, 5-trichlorophenyl; n can be an integer ranging from 3 to 11; and the stereocenter * can be (S).

In one embodiment, in the crystalline compound of Formula (I) or its crystalline salt, $R_1$ can be methyl, $R_2$ can be 9-Fluorenylmethoxycarbonyl (Fmoc); $R_3$ can be —H, n can be 3, 6, or 11, and the stereocenter * can be (R).

In one embodiment, in the crystalline compound of Formula (I) or its crystalline salt, $R_1$ can be methyl, $R_2$ can be 9-Fluorenylmethoxycarbonyl (Fmoc); $R_3$ can be —H, n can be 3, 6, or 11, and the stereocenter * can be (S).

Chemical Purity

Herein, unless otherwise indicated, any compound, its salt, crystalline compound, or crystalline salt of a compound, can have a chemical purity. Chemical purity can be defined, for example, as the degree to which a substance is undiluted or unmixed with extraneous material, and can be typically expressed as a percentage. Any compound, salt thereof, crystalline compound, or crystalline salt of a compound herein can have, for example, a chemical purity ranging from about 90% to 100%. The chemical purity can be, for example, about 92% to 100%, about 94% to 100%, about 96% to 100%, about 98% to 100%, about 90%, about 91%, about 92%, about 93%, about 94%, about 95%, about 96%, about 97%, about 98%, about 99%, or about 100%. The percentage can be, for example, based on the total weight of the compound, its salt, crystalline compound, or its salt. The percentage can be, for example, arrived at using HPLC. The percentage can be arrived at, for example, using NMR, for example proton NMR. The chemical purity can be arrived at, for example, using elemental analysis.

Enantiomeric Excess

Herein, unless otherwise indicated, any compound, salt thereof, crystalline compound, or crystalline salt of a compound, can have an enantiomeric excess. The enantiomeric excess can be, for example, from about 80% to 100%, from about 85% to 100%, from about 90% to 100%, from about 95% to 100%, from about 96% to 100%, from about 97% to 100%, from about 98% to 100%, from about 99% to 100%, about 95%, about 96%, about 97%, about 97.2%, about 98%, about 99%, or 100%. The enantiomeric excess can be, for example, greater than 95%, greater than 96%, greater than 97%, greater than 98%, or greater than 99%. Herein, unless otherwise indicated, enantiomeric excess can be calculated, for example, by the formula: enantiomeric excess (ee)=((P−S)/(P+S))×100%, where P and S represent the moles, respectively, of the predominant and subdominant enantiomer produced or present in a sample. For example, if the more moles of the (R) enantiomer are produced than moles of the (S) enantiomer, moles of (R) enantiomer are designated as R, and moles of the (S) enantiomer are designated as S, then the enantiomeric excess formula becomes: ee (%)=((R−S)/(R+S))×100%. Herein, unless otherwise indicated, the amount (e.g., moles) or enantiomer produced can be determined, for example, by chiral HPLC, by chiral GC, or via a chiral NMR shift reagent using NMR spectroscopy.

Optical Purity

Herein, unless otherwise indicated, any compound, its salt, crystalline compound, or crystalline salt of a compound, can have an optical purity. The optical purity can be, for example, from about 80% to 100%, from about 85% to 100%, from about 90% to 100%, from about 95% to 100%, about 95%, about 96%, about 97%, about 98%, about 99%, or 100%. Herein, unless otherwise indicated, optical purity can be calculated using the formula: optical purity (%)=([α]observed/[α]maximal)*100%, where [α]observed is the specific rotation of the sample, and [α]maximal is the specific rotation of the pure enantiomer. Herein, unless otherwise indicated, specific rotation can be defined as the observed angle of optical rotation, α, when plane-polarized light is passed through a sample with a path length of 1 decimeter and a sample concentration of 1 gram per 1 milliliter. The specific rotation can be obtained, for example, at 20° C. and at a wavelength of light of 589 nanometers (e.g., the sodium D line). Herein, unless otherwise indicated, the specific rotation can be obtained, for example, with a polarimeter. Herein, unless otherwise indicated, the solvent the sample is dissolved in can be any suitable solvent or solvent combination, for example, ethanol, methanol, chloroform, dichloromethane, carbon tetrachloride, water, DMSO, N,N-DMF, diethyl ether, tetrahydrofuran, hexane, pentane, acetone, or any combination thereof.

Diastereomeric Excess

Herein, unless otherwise indicated, the compounds, salts, crystalline compounds, or crystalline salts of compounds herein can be diastereomers. When this is so, the compounds, crystalline compounds, or crystalline salts of compounds herein can have a diastereomeric excess of, for example, from about 80% to 100%, from about 85% to 100%, from about 90% to 100%, from about 95% to 100%, about 95%, about 96%, about 97%, about 98%, about 99%, or 100%. Herein, unless otherwise indicated, the diastereomeric excess, for example, in a mixture of two diastereomers, can be calculated, for example, by the formula: diastereomeric excess de %=((D1−D2)/(D1+D2))*100%, wherein D1 represents, for example, the mole or percent weight of a first and most abundant diastereomer, and D2 represents, for example, the mole or percent weight of a second and least abundant diastereomer, where mole percent is used consistently (e.g., alone) E the calculation, or where percent weight is used consistently (e.g., alone) in the calculation.

Converted Enantiomeric Excess or Optical Purity

Unless otherwise indicated, any compound, salt thereof, crystalline compound, or crystalline salt thereof, herein, that is a diastereomer, can be converted to an enantiomer or enantiomeric mixture having one stereocenter (e.g., * in Formula (I)) by, for example, removal of a nitrogen protecting group (e.g., removal of the nitrogen protecting group $R_2$ in the crystalline compound of Formula (I) or its crystalline salt that, together with the stereocenter *, creates a diastereomer), and the resulting enantiomer or enantiomeric mixture can then have its enantiomeric excess or optical purity determined as described herein. The resulting enantiomeric excess or optical purity, in these circumstances, is termed a converted enantiomeric excess or converted optical purity. The converted enantiomeric excess can be, for example, from about 80% to 100%, from about 85% to 100%, from about 90% to 100%, from about 95% to 100%, from about 96% to 100%, from about 97% to 100%, from about 98% to 100%, from about 99% to 100%, about 95%, about 96%, about 97%, about 97.2%, about 98%, about 99%, or 100%. The converted enantiomeric excess can be, for example, greater than 95%, greater than 96%, greater than 97%, greater than 98%, or greater than 99%. The converted optical purity can be, for example, from about 80% to 100%, from about 85% to 100%, from about 90% to 100%, from about 95% to 100%, about 95%, about 96%, about 97%, about 98%, about 99%, or 100%. Thus, any optionally crystalline diastereomer or its optionally crystalline salt herein, unless otherwise indicated, can have a converted enantiomeric excess or converted optical purity.

Specifically Exemplified Crystalline Compounds and Crystalline Salts Thereof

Herein, unless otherwise indicated, the crystalline compound of Formula (I) or its crystalline salt can be a compound of Formula (IIa) or its crystalline salt:

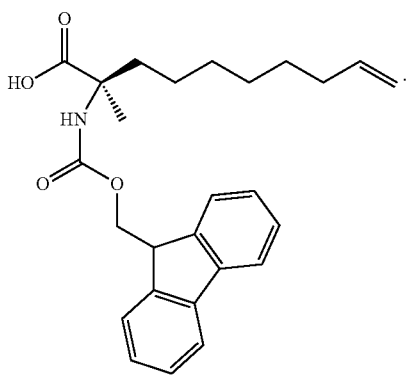

(IIa)

Herein, unless otherwise indicated, the crystalline compound of Formula (I) or its crystalline salt can be a compound of Formula (IIb) or its crystalline salt:

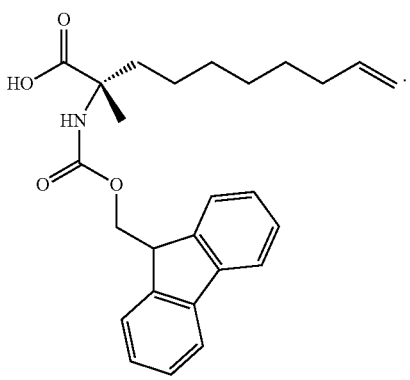

(IIb)

Herein, unless otherwise indicated, the crystalline compound of Formula (I) or its crystalline salt can be a compound of Formula (IIIa) or its crystalline salt:

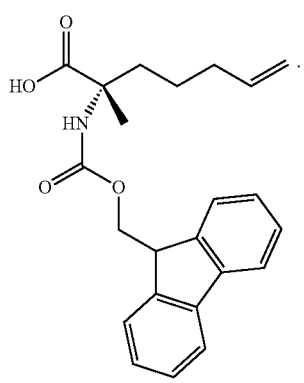

(IIIa)

Herein, unless otherwise indicated, the crystalline compound of Formula (I) or its crystalline salt can be a compound of Formula (IIIb) or its crystalline salt:

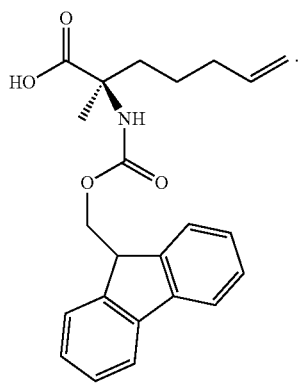

(IIIb)

Deuterated and Halogenated Compounds and their Salts

Also provided herein, unless otherwise indicated, are optionally crystalline compounds and their optionally crystalline salts of Formula (IV):

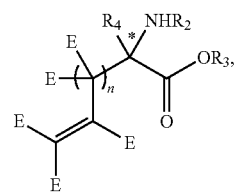

Formula (IV)

wherein $R_2$, $R_3$, n, and * are the same as in the crystalline compound or its crystalline salt of Formula (I), each E is independently selected from the group consisting of deuterium and halogen, and $R_4$ is selected from the group consisting of $C_1$-$C_3$ alkyl, $C_1$-$C_3$ deuteroalkyl and $C_1$-$C_3$ haloalkyl.

Deuterium

Herein, unless otherwise indicated, for any deuterated: compound, its salt, crystalline compound, or its crystalline salt; greater than 90%, greater than 92%, greater than 94%, greater than 96%, or greater than 98%, of the deuterated: compound, its salt, crystalline compound, or its crystalline salt; has a deuterium atom at each position designated as deuterium (D) in the deuterated: compound, its salt, the crystalline compound, or its crystalline salt.

Methods of Making

The compounds and their salts herein can be advantageously made by methods disclosed herein that result in at least one of the following advantages:
- the compounds or their salts that are produced are crystalline;
- the compounds and their salts (both of which can be crystalline) are advantageously produced in high yield;
- the compounds and their salts (both of which can be crystalline) are advantageously produced in high chemical purities;
- the compounds and their salts (both of which can be crystalline) are advantageously produced in high enantiomeric excess, optical purity, diastereomeric excess, high converted enantiomeric excess, or high converted optical purity; or
- the compounds and their salts (both of which can be crystalline) are produced without chromatographic purification (e.g., without chromatography).

Unless otherwise indicated, the compounds, their salts, crystalline compounds, and their crystalline salts, herein can be produced using for example exemplary Scheme I (with modifications that would be readily apparent to a skilled artisan). Scheme I depicts formation of the crystalline N-Fmoc-(R)-α-methyl-α-aminodec-9-enoic acid (i.e., the crystalline compound of Formula (IIa)). Sequence I starts with Boc-D-proline (i.e., the compound of Formula (V)). It is understood that by starting with Boc-L-proline, compounds with the opposite stereochemistry of the compound of Formula (IIa) can be produced (e.g., the compound of Formula (IIb) can be produced). It is also understood that the stereochemistry of the amino acid used to form the metal complex (e.g., alanine used to form the metal complex of Formula (XI) in Scheme I) is not dispositive of the stereochemistry in the resulting crystalline compound (e.g., of Formula (IIa)) or its crystalline salt.

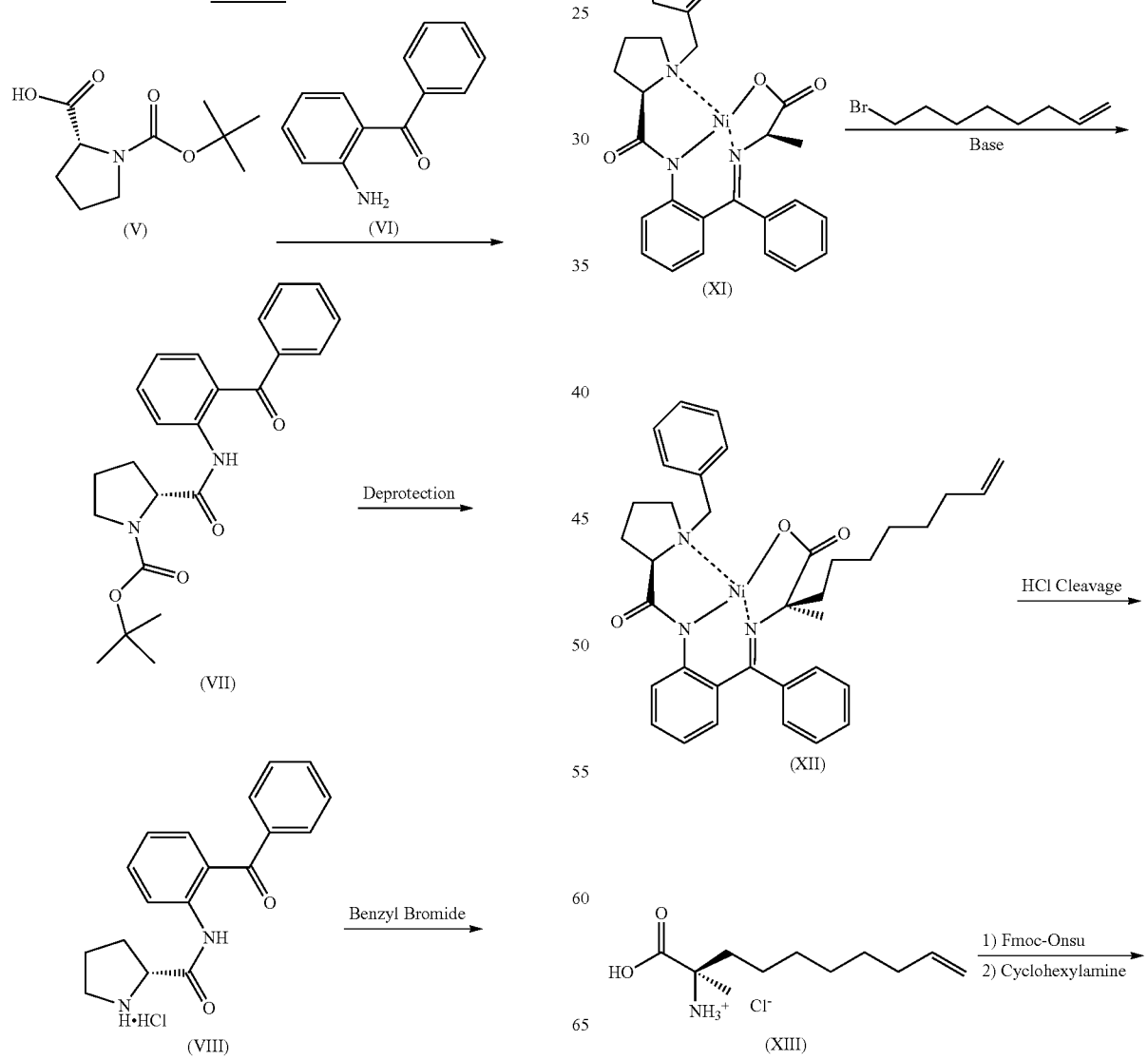
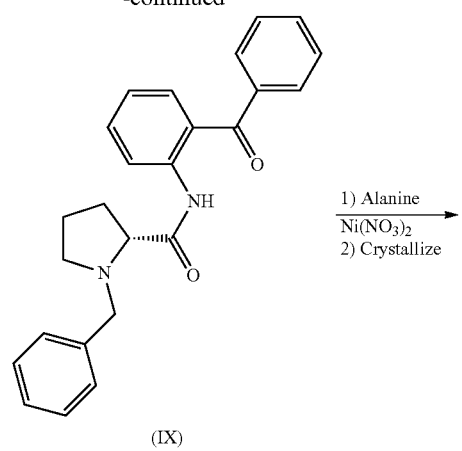

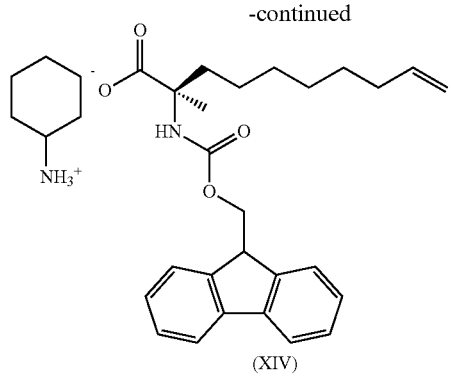

(XIV)

1) Crystallize
2) H$_2$SO$_4$
3) Crystallize

Crystalline Compound of Formula (IIa)

In Scheme I, Boc-D-proline (Compound of Formula (V)) is first reacted with 2-aminobenzophenone (compound of Formula (VI)) to form the compound of Formula (VII). Next, the compound of Formula (VII) is deprotected to form the HCl salt of the compound of Formula (VIII). A skilled artisan would readily understand that the synthetic scheme contemplates use of acids other than HCl, including organic acids and inorganic acids, for example, nitric acid, phosphoric acid, sulfuric acid, boric acid, hydrofloric acid, hydrobromic acid, and perchloric acid.

The salt of the compound of Formula (VIII) is next reacted with benzyl bromide, and for example, a base, to form the compound of Formula (IX). A skilled artisan would readily understand that substituted benzyl halides could be employed in place of benzyl bromide. For example, the following benzyl halides, where X=Cl, Br, or I, could be employed:

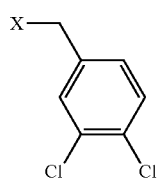

(X$_a$)

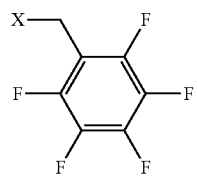

(X$_b$)

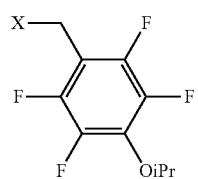

(X$_c$)

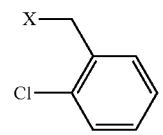

(X$_d$)

Representative benzyl halides are found in Belokon, Y. N., et al., "Halo-substituted (S)—N-(2-benzoylphenyl)-1-benzylpyrrolidine-2-carboxamides as new chiral auxiliaries for the asymmetric synthesis of (S)-α-amino acids,"*Russian Chemical Bulletin, International Edition,* 51(8): 1593-1599 (2002). Further and different benzyl halides could also be employed:

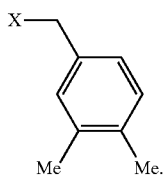

(X$_e$)

(X$_f$)

These representative benzyl halides are found in Saghiyan, A. S., et al., "New chiral NiII complexes of Schiff's bases of glycine and alanine for efficient asymmetric synthesis of α-amino acids," *Tedrahedron: Asymmetry* 17: 455-467 (2006).

Next, the compound of Formula (IX) is reacted with L-alanine and Ni(NO$_3$)$_2$ to form the metal complex of Formula (XI). The skilled artisan would understand that other amino acids other than alanine could be employed in Scheme I. For example, glycine; 2-aminobutanoic acid, 2-aminopentanoic acid, and valine, for example in their D or L forms, could be employed. The Ni(NO$_3$)$_2$ can be a hydrate, for example, a hexahydrate. The reaction can be run in an alcoholic solvent, for example, methanol. The reaction can be run at an elevated temperature, for example, from about 40° C. to about 60° C. The reaction can be run in the presence of a base, for example, a hydroxide, for example an inorganic hydroxide, for example, potassium hydroxide. Other hydroxides are contemplated, including sodium hydroxide, cesium hydroxide, lithium hydroxide, magnesium hydroxide, and ammonium hydroxide.

To increase purity of the final product from Scheme I, the metal complex of Formula (XI) can be crystallized one or more times from one or more solvents, for example a cyclic ether and a non-cyclic ether. In one embodiment, the solvent is tetrahydrofuran and methyl tert-butyl ether. In some cases the ratio of the cyclic ether to the non-cyclic ether is at most 0.5:10, 1.0:10, 1.5:10, 2.0:10, 2.5:10, 3.0:10, 3.5:10, 4.0:10, 4.5:10 or 5:10. In other cases the ratio of the cyclic ether to the non-cyclic ether is at least 0.5:10, 1.0:10, 1.5:10, 2.0:10, 2.5:10, 3.0:10, 3.5:10, 4.0:10, 4.5:10 or 5:10. For example, some cases the metal complex of Formula (XI) is crystallized from a mixture of tetrahydrofuran and methyl tert-butyl ether in ratio of at most 0.5:10, 1.0:10, 1.5:10, 2.0:10, 2.5:10, 3.0:10, 3.5:10, 4.0:10, 4.5:10 or 5:10. In other cases the ratio of and tetrahydrofuran and methyl tert-butyl ether is at least 0.5:10, 1.0:10, 1.5:10, 2.0:10, 2.5:10, 3.0:10, 3.5:10, 4.0:10, 4.5:10 or 5:10. In some cases the ratio of tetrahydrofuran and methyl tert-butyl ether is 1.5:10. The metal complex of Formula (XI) may also be crystallized with esters, for example with ethyl acetate or isopropyl acetate. The product or crystallized product of Formula (IX) can alternatively or additionally be crystallized or recrystallized from a solvent, for example an alcohol, for example isopropyl alcohol. Other alcohols are contemplated, including methanol, ethanol, n-propanol, a butanol, n-butanol, iso-butanol, sec-butanol, and tert-butanol.

The metal complex of Formula (XI) is then alkylated with 8-bromooct-1-ene to form the alkylated metal complex of Formula (XII). The skilled artisan would understand that other alkylating agents, including other halo alkyl olefins, could be used in place of 8-bromooct-1-ene. For example, alkylating agents of the Formula (XV) could be used:

(XV)

wherein X is Cl, Br, or I, and n is an integer from 1 to 20. For example, n can be from 3 to 11, from 3 to 6, or 3 or 6. Some or all of the hydrogen atoms present in the compound of Formula (XV) can be replaced with deuterium atoms or halogen atoms. The alkylation can be performed in one or more solvents, for example a polar aprotic solvent, for example N, N-dimethyl formamide (DMF). The alkylation can be performed, for example, at a temperature of less than 20° C., for example, from less than 20° C. to 5° C., from less than 20° C. to 10° C., or at about 10° C. The skilled artisan would also understand that when glycine is used to form the metal complex, two alkylations could be performed one after the other. For example, the first alkylation could be performed using a $C_1$-$C_3$ alkane with a leaving group such as a halogen (e.g., methyl bromide, ethyl bromide, n-propyl bromide), or a $C_1$-$C_3$ deuteroalkane with a leaving group such as a halogen (e.g., $CD_3Br$, $CD_3CD_2Br$, $CD_3CD_2CD_2Br$), or a $C_1$-$C_3$ haloalkane with a leaving group such as a more reactive halogen than the other halogens in the haloalkane (e.g., $CF_3Br$, $CF_3CF_2Br$, $CF_3CF_2CF_2Br$). Then, the second alkylation could be performed using the alkylating agent of Formula (XV). The order of the first and second alkylations can be reversed.

Purification of Formula (XII) may be achieved by crystallization one or more times from one or more solvents including cyclic and non-cyclic ethers, esters, hexanes and heptanes. For example crystallization may be achieved using a combination of ethyl acetate and hexanes, ethyl acetate and heptanes, isopropyl acetate and hexanes, isopropyl acetate and heptanes, methyl tertiary-butyl ether and hexanes, methyl tertiary-butyl ether and heptanes or isopropyl acetate and methyl tertiary-butyl ether.

The metal complex of Formula (XII) is then cleaved with an acid, for example HCl, using one or more solvents, for example an ether, for example a cyclic ether, for example tetrahydrofuran, to form the amino acid HCl salt of Formula (XIII). The skilled artisan would understand that other acids in addition to HCl are contemplated, for example organic or inorganic acids, for example, nitric acid, phosphoric acid, sulfuric acid, boric acid, hydrofloric acid, hydrobromic acid, or perchloric acid. The salt of Formula (XIII) may be further purified by crystallization one or more times with one or more solvents. The solvent may be any suitable solvent including tetrahydrofuran, methyl tertiary-butyl ether, ethyl acetate, isopropyl acetate, ethanol, methanol, isopropanol, acetonitrile, or a combination thereof. In one embodiment, the solvent is acetonitrile.

The amino acid salt of Formula (XIII) is then nitrogen protected with a nitrogen protecting group, in this case an Fmoc group, and the cyclohexylamine addition salt of the protected amino acid is formed, yielding the protected amino acid cyclohexylamine salt of Formula (XIV). Formation of the salt of Formula (XIV) can be achieved in any suitable solvent including acetonitrile, methyl tertiary-butyl ether, tetrahydrofuran or a combination thereof. In one embodiment, the solvent is methyl tertiary-butyl ether. A skilled artisan would understand that other amines, for example other cyclic amines, for example cyclopropylamine, cyclobutyl amine, cyclopentylamine, cycloheptylamine, and cyclooctylamine, are contemplated. One of skill in the art would also readily understand that other nitrogen protecting groups are contemplated, for example the nitrogen protecting groups for $R_2$ in the crystalline compound of Formula (I) or its crystalline salt herein.

The protected amino acid cyclohexylamine salt of Formula (XIV) can then be crystallized from one or more ethers, for example, two ethers, for example a cyclic ether and a non cyclic ether, for example tetrahydrofuran and methyl tert-butyl ether.

The crystallized amino acid cyclohexylamine salt of Formula (XIV) is then treated with sulfuric acid, and subsequently crystallized to form the crystalline compound of Formula (IIa). The skilled artisan would understand that acids other than sulfuric acid are contemplated, for example organic or inorganic acids, for example, nitric acid, phosphoric acid, sulfuric acid, boric acid, hydrofloric acid, hydrobromic acid, or perchloric acid. The crystallization can be performed using one or more solvents, for example two solvents, for example an alkane and haloalkane, for example hexanes and chloroform. In some cases the ratio of the alkane to the haloalkane is at least 6:1, 5:1, 4:1, 3:1, 2:1, or 1:10. In some cases the ratio of the alkane to the haloalkane is at most 6:1, 5:1, 4:1, 3:1, 2:1, or 1:10. For example, the crystalline compound of Formula (IIa) may be obtained by crystallization from a mixture of hexanes and chloroform in the ratio of at least 6:1, 5:1, 4:1, 3:1, 2:1, or 1:1. The crystalised IIa may also obtained by crystallization from a mixture of hexanes and chloroform in the ratio of at most 6:1, 5:1, 4:1, 3:1, 2:1, or 1:1. In some cases the ratio of hexanes and chloroform is 3:1.

The crystallization can be performed at a temperature ranging from, for example, about −5° C. to about −20° C., about −10° C. to about −20° C., or about −15° C. to −20° C.

The skilled artisan would understand, for example, that the crystalline compound of Formula (IIa) could be further activated or protected at its carboxylic acid function with, for example, a protecting or activating group $R_3$ of the crystalline compound of Formula (I) or its crystalline salt. Unless otherwise indicated, the compounds, their salts, crystalline compounds, and their crystalline salts, herein can be produced using exemplary Scheme II (with modifications that would be readily apparent to a skilled artisan). Scheme II depicts formation of the crystalline N-Fmoc-(S)-α-methyl-α-aminohept-6-enoic acid (i.e., the crystalline compound of Formula (IIIa)). Sequence II starts with Boc-L-Proline (i.e., the compound of Formula (Va)). It is understood that by starting with Boc-D-proline, compounds with the opposite stereochemistry of the compound of Formula (IIIa) can be produced (e.g., the compound of Formula (IIIb) can be produced). It is also understood that the stereochemistry of the amino acid used to form the metal complex, and whose alpha carbon atom is subsequently alkylated by the haloolefin (e.g., alanine in Formula (XIa)) is not dispositive of the stereochemistry in the resulting crystalline compound (e.g., of Formula (IIIa)) or its crystalline salt.

Scheme II

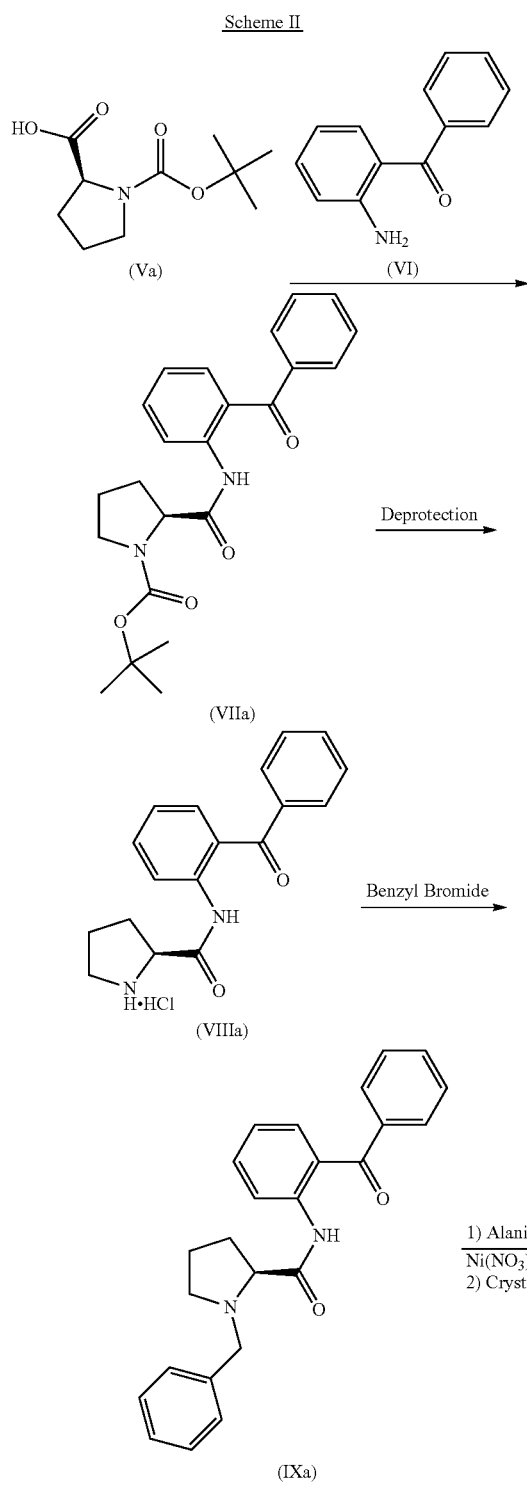

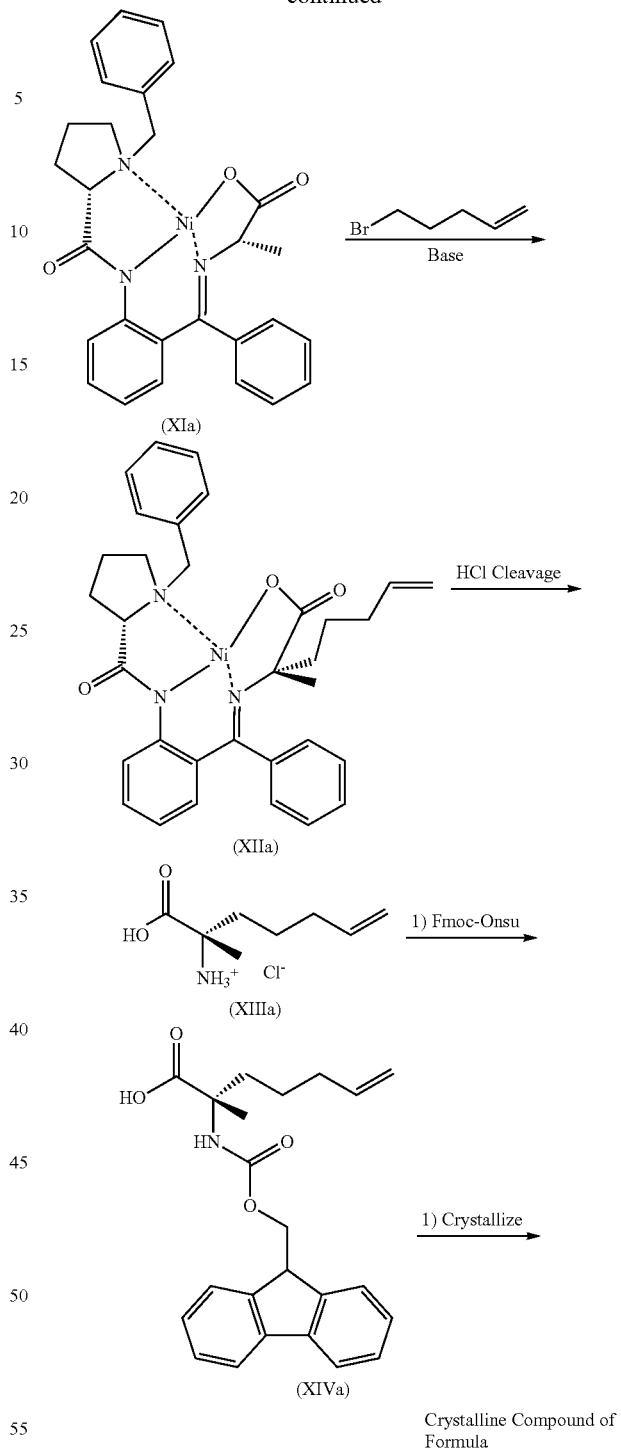

In Scheme II, Boc-L-proline (Compound of Formula (Va)) is first reacted with 2-aminobenzophenone (compound of Formula (VI)) to form the compound of Formula (VIIa). Next, the compound of Formula (VIIa) is deprotected to form the HCl salt of the compound of Formula (VIIIa). A skilled artisan would readily understand that the synthetic scheme contemplates use of acids other than HCl, including organic acids and inorganic acids, for example, nitric acid, phosphoric acid, sulfuric acid, boric acid, hydrofloric acid, hydrobromic acid, and perchloric acid.

The salt of the compound of Formula (VIIIa) is next reacted with benzyl bromide, and for example a base, to form the compound of Formula (IXa). A skilled artisan would readily understand that substituted benzyl halides could be employed in place of benzyl bromide. For example, the following benzyl halides, where X=Cl, Br, or I, could be employed:

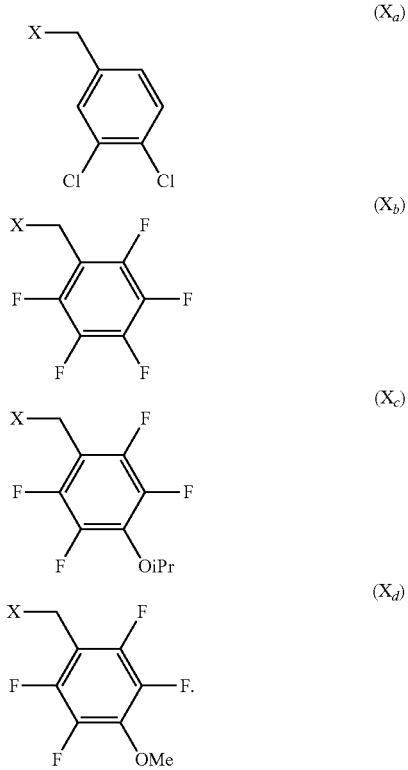

Representative benzyl halides are found in Belokon, Y. N., et al., "Halo-substituted (S)—N-(2 benzoylphenyl)-1-benzylpyrolidine-2-carboxamides as new chiral auxiliaries for the asymmetric synthesis of (S)-α-amino acids,"*Russian Chemical Bulletin, International Edition,* 51(8): 1593-1599 (2002). Further and different benzyl halides could also be employed:

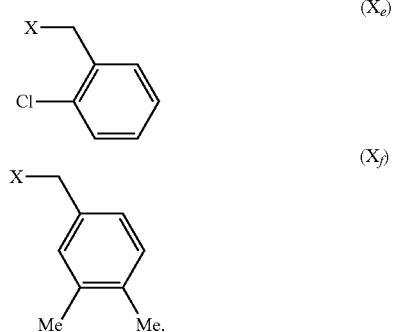

These representative benzyl halides are found in Saghiyan, A. S., et al., "New chiral NiII complexes of Schiff's bases of glycine and alanine for efficient asymmetric synthesis of α-amino acids," *Tedrahedron: Asymmetry* 17: 455-467 (2006).

Next, the compound of Formula (IXa) is reacted with L-alanine and $Ni(NO_3)_2$ to form the metal complex of Formula (XIa). The skilled artisan would understand that other amino acids other than alanine could be employed in Scheme II. For example, glycine; 2-aminobutanoic acid, 2-aminopentanoic acid, and valine could be employed, for example in their D or L forms. The $Ni(NO_3)_2$ can be a hydrate, for example, a hexahydrate. The reaction can be run in an alcoholic solvent, for example, methanol. The reaction can be run at an elevated temperature, for example, from about 40° C. to about 60° C. The reaction can be run in the presence of a base, for example, a hydroxide, for example an inorganic hydroxide, for example, potassium hydroxide. Other hydroxides are contemplated, including sodium hydroxide, lithium hydroxide, cesium hydroxide, and magnesium hydroxide.

To increase purity of the final product from Scheme II, the metal complex of Formula (XIa) can be crystallized one or more times from one or more solvents, for example a cyclic ether and a non-cyclic ether, for example tetrahydrofuran and methyl tert-butyl ether. In some cases the ratio of the cyclic ether to the non-cyclic ether is at most 0.5:10, 1.0:10, 1.5:10, 2.0:10, 2.5:10, 3.0:10, 3.5:10, 4.0:10, 4.5:10 or 5:10. In other cases the ratio of the cyclic ether to the non-cyclic ether is at least 0.5:10, 1.0:10, 1.5:10, 2.0:10, 2.5:10, 3.0:10, 3.5:10, 4.0:10, 4.5:10 or 5:10. For example, some cases the metal complex of Formula (XIa) is crystallized from a mixture of tetrahydrofuran and methyl tert-butyl ether in ratio of at most 0.5:10, 1.0:10, 1.5:10, 2.0:10, 2.5:10, 3.0:10, 3.5:10, 4.0:10, 4.5:10 or 5:10. In other cases the ratio of and tetrahydrofuran and methyl tert-butyl ether is at least 0.5:10, 1.0:10, 1.5:10, 2.0:10, 2.5:10, 3.0:10, 3.5:10, 4.0:10, 4.5:10 or 5:10. In some cases the ratio of tetrahydrofuran and methyl tert-butyl ether is 1.5:10. The product or crystallized product of Formula (IXa) can be crystallized or recrystallized from a solvent, for example an alcohol, for example isopropyl alcohol. Other alcohols are contemplated, including methanol, ethanol, n-propanol, a butanol, n-butanol, iso-butanol, sec-butanol, and t-butanol. Other solvents suitable for crystallization or recrystallization of Formula (XIa) include esters, for example ethyl acetate or isopropyl acetate.

The metal complex of Formula (XIa) is then alkylated with 5-bromopent-1-ene to form the alkylated metal complex of Formula (XIIa). The skilled artisan would understand that other alkylating agents, including other halo alkyl olefins, could be used in place of 5-bromopent-1-ene. For example, alkylating agents of the Formula (XV) could be used:

wherein X is Cl, Br, or I, and n is an integer from 1 to 20. For example, n can be from 3 to 11, from 3 to 6, or 3 or 6. Some or all of the hydrogen atoms present in the compound of Formula (XV) can be replaced with deuterium atoms or halogen atoms. The alkylation can be performed in one or more solvents, for example a polar aprotic solvent, for example N, N-dimethyl formamide (DMF). The alkylation can be performed, for example, at a temperature of less than 20° C., for example, from less than 20° C. to 5° C., from less than 20° C. to 10° C., or at about 10° C. The skilled artisan would also understand that when glycine is used to form the metal complex, two alkylations could be performed one after the other. For example, the first alkylation could be performed using a $C_1$-$C_3$ alkane with a leaving group such as a halogen (e.g., methyl bromide, ethyl bromide, n-propyl bromide), or a $C_1$-$C_3$ deuteroalkane with a leaving group such as a halogen (e.g., $CD_3Br$, $CD_3CD_2Br$, $CD_3CD_2CD_2Br$), or a $C_1$-$C_3$ haloalkane with a leaving group such as a more reactive halogen than the other halogens in the haloalkane (e.g., $CF_3Br$, $CF_3CF_2Br$, $CF_3CF_2CF_2Br$). Then, the second alkylation could be performed using the alkylating agent of Formula (XV). The order of the first and second alkylations can be reversed.

Purification of Formula (XIIa) may be achieved by crystallization one or more times from one or more solvents including cyclic and non-cyclic ethers, esters, hexanes and heptanes. For example crystallization may be achieved by using a combination of ethyl acetate and hexanes, ethyl acetate and heptanes, isopropyl acetate and hexanes, isopropyl acetate and heptanes, methyl tertiary-butyl ether and hexanes, methyl tertiary-butyl ether and heptanes or isopropyl acetate and methyl tertiary-butyl ether.

The metal complex of Formula (XIIa) is then cleaved with an acid, for example HCl, using one or more solvents, for example an ether, for example a cyclic ether, for example tetrahydrofuran, to form the amino acid HCl salt of Formula (XIIIa). The skilled artisan would understand that other acids in addition to HCl are contemplated, for example organic or inorganic acids, for example, nitric acid, phosphoric acid, sulfuric acid, boric acid, hydrofloric acid, hydrobromic acid, or perchloric acid.

The salt of Formula (XIIIa) may be further purified by crystallization one or more times with one or more solvents. The solvent may be any suitable solvent including tetrahydrofuran, methyl tertiary-butyl ether, ethyl acetate, isopropyl acetate, ethanol, methanol, isopropanol, acetonitrile, or a combination thereof. In one embodiment, the solvent is acetonitrile.

The amino acid salt of Formula (XIIIa) is then nitrogen protected with a nitrogen protecting group, in this case an Fmoc group, yielding the protected amino acid of Formula (XIVa). In some embodiments, the compound of Formula (XIVa) is taken on to the crystallization step as is. In other embodiments, the compound of Formula (XIVa) is converted to a salt prior to crystallization. Formation of the salt of Formula (XIVa) may be achieved in any suitable solvent including acetonitrile, methyl tertiary-butyl ether, tetrahydrofuran or a combination thereof. One of skill in the art would also readily understand that other nitrogen protecting groups are contemplated, for example the nitrogen protecting groups for $R_2$ in the crystalline compound of Formula (I) or its crystalline salt herein. For example, a protected amino acid cyclohexylamine salt of Formula (XIVa) can then be crystallized from one or more ethers, for example, two ethers, for example a cyclic ether and a non cyclic ether, for example tetrahydrofuran and methyl tert-butyl ether.

The protected amino acid cyclohexylamine salt of Formula (XIVa) can then be crystallized to form the crystalline compound of Formula (IIIa).

The crystallization can be performed using one or more solvents, for example two solvents, for example an alkane and haloalkane, for example hexanes and chloroform. In some cases the ratio of the alkane to the haloalkane is at least 6:1, 5:1, 4:1, 3:1, 2:1, or 1:10. In some cases the ratio of the alkane to the haloalkane is at most 6:1, 5:1, 4:1, 3:1, 2:1, or 1:10. For example, the crystalline compound of Formula (IIIa) may be obtained by crystallization from a mixture of hexanes and chloroform in the ratio of at least 6:1, 5:1, 4:1, 3:1, 2:1, or 1:1. The crystalised IIIa may also obtained by crystallization from a mixture of hexanes and chloroform in the ratio of at most 6:1, 5:1, 4:1, 3:1, 2:1, or 1:1. In some cases the ratio of hexanes and chloroform is 2:1.

The crystallization can be performed at a temperature ranging from, for example, about −5° C. to about −20° C., about −10° C. to about −20° C., or about −15° C. to −20° C. Herein, unless otherwise indicated, any compound or its salt may be crystalline. Herein, unless otherwise indicated, any compound or its salt may be crystalline at a temperature, for example, of about 0° C. or less, about −5° C. or less, about −10° C. or less, about −15° C. or less, about −20° C. or less, about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., or about −20° C.

The skilled artisan would understand, for example, that the crystalline compound of Formula (IIIa) could be further activated or protected at its carboxylic acid function with, for example, a protecting or activating group $R_3$ of the crystalline compound of Formula (I) or its crystalline salt.

Stapled and Stitched Polypeptides

The crystalline compounds and their crystalline salts of Formula (I), including the crystalline compounds and their crystalline salts of Formulae (IIa), (IIb), (IIIa) and (IIIb), as well as the optionally crystalline compounds and their optionally crystalline salts of Formula (IV), can be used to synthesize peptides, polypeptides, and crosslinked polypeptides that are useful for treating and preventing diseases.

The crosslinked polypeptides can contain secondary structures such as a helix, for example, an alpha helix. The crosslinker can stabilize the secondary structures relative to an otherwise identical but uncrosslinked polypeptide. And the crosslinker can be formed by, for example, joining the terminal alkene side chains of, for example, two crystalline alkene α, α-disubstituted amino acids or their crystalline salts herein that are incorporated into a polypeptide through, for example, a metal catalyzed olefin metathesis reaction (e.g., forming a stapled peptide). This process is depicted in Scheme III, below:

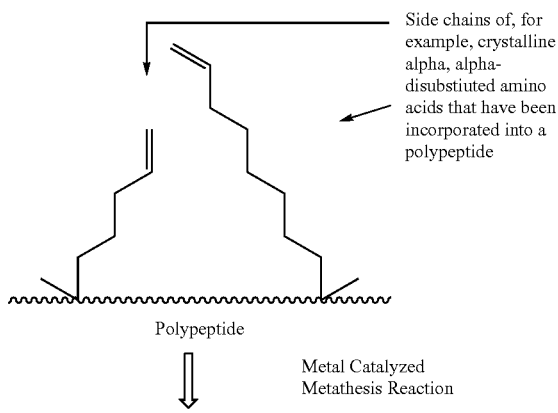

Scheme III

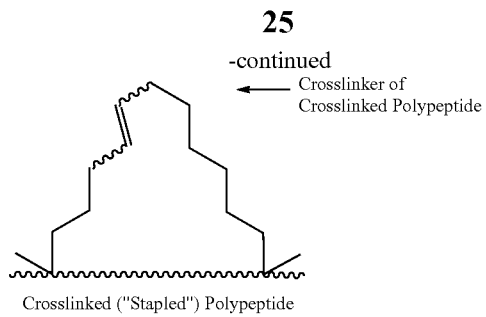

Crosslinked ("Stapled") Polypeptide

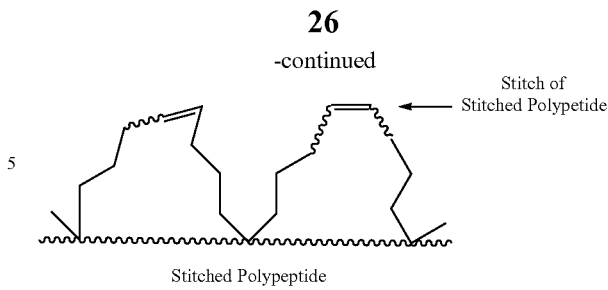

Stitched Polypeptide

Examples of stapled polypeptides are found, inter alia, for example, in International Application No. PCT/US2004/038403.

The crystalline compounds and their crystalline salts of Formula (I), including the crystalline compounds and their crystalline salts of Formulae (IIa), (IIb), (IIIa) and (IIIb), as well as the optionally crystalline compounds and their optionally crystalline salts of Formula (IV), can be used to synthesize peptides, polypeptides, and stitched polypeptides that are useful for treating and preventing diseases.

For example, two of the crystalline compounds and their crystalline salts of Formula (I), can be incorporated into a polypeptide backbone along with an α, α-disubstituted amino acid having terminal olefins on each of its side chains, for example the compound of Formula (XVI):

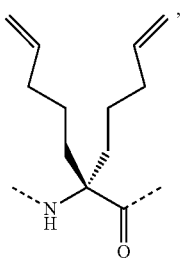 (XVI)

as shown in scheme IV. Metal catalyzed metathesis reaction of the olefins yields a stitched peptide.

Scheme IV

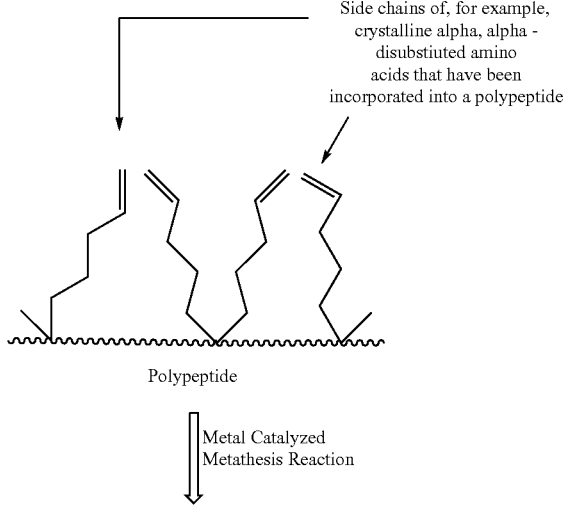

Examples of stitched polypeptides are found, for example, in International Application Publication No. WO2008/121767.

Methods to effect formation of peptidomimetic macrocycles which are known in the art can be employed. For example, the preparation of peptidomimetic macrocycles are described in Schafmeister et al., *J. Am. Chem. Soc.* 122: 5891-5892 (2000); Schafmeister & Verdine, *J. Am. Chem. Soc.* 122:5891 (2005); Walensky et al., *Science* 305:1466-1470 (2004); U.S. Pat. No. 7,192,713 and International Pat. App. Pub. No. WO 2008/121767.

Herein, unless otherwise indicated, the term "peptide synthesis" encompasses coupling of two or more amino acids with the aid of a coupling reagent. Peptide synthesis may be performed in "liquid" or "solution" phase where the coupling of the amino acids is performed in a solvent system. Peptide synthesis may also, or alternatively, be performed on "solid phase" where an amino acid is attached to a polymeric or solid support by a covalent bond at the N- or C-terminus of an amino acid. Peptides can be made, for example, by chemical synthesis methods, such as those described in Fields et al., Chapter 3 in *Synthetic Peptides: A User's Guide*, ed. Grant, W. H. Freeman & Co., New York, N.Y., 1992, p. 77; and Goodman, M., et al., Houben-Weyl Methods in Organic Chemistry: Synthesis of Peptides and Peptidomimetics, *Thieme Publishers, Volumes* 1-5, (1994). For example, peptides can be synthesized using automated Merrifield techniques of solid phase synthesis with the amino groups of the amino acids employed in the synthesis protected, for example by t-Boc or Fmoc protecting groups. An automated peptide synthesizer (e.g., Applied Biosystems (Foster City, Calif.), Model 430A, 431, or 433) can be employed in making peptides.

Herein unless otherwise indicated, peptidomimetic precursors and peptidomimetic macrocycles and their salts described herein can be produced using solid phase peptide synthesis (SPPS), where for example, a C-terminal amino acid is attached to a cross-linked polystyrene resin via an acid or base labile bond with a linker. The resin can be, for example, insoluble in the solvents used for synthesis, making it relatively simple and fast to wash away excess reagents and by-products. The N-terminus of each amino acid added to the growing peptide chain can be protected, for example, with an Fmoc group, which is stable in acid, but removable by base. Side chain functional groups can be protected, as necessary or desirable, for example, with base stable, acid labile groups.

Herein, unless otherwise indicated, the peptidomimetic precursors can be made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

Herein, unless otherwise indicated, solution peptide synthesis can be performed in a manner wherein reagents are fully or partially dissolved in, for example, an appropriate solvent, for example, a polar aprotic solvent. In a representative case employing, for example, a solid crystalline N-terminally protected olefinic amino acid with a removable protecting group (e.g., t-Butyloxycarbonyl, Benzyloxycarbonyl, Fluorenylmethoxycarbonyl) and a C-protected amino acid with a selectively removable ester (e.g., methyl, benzyl, t-butyl), the amino acids can be fully or partially dissolved in a solvent and an activating agent is added to accomplish peptide bond formation between the amino acids. Solution peptide synthesis can also utilize first formation of active esters of N-protected olefinic amino acids (e.g., N-hydroxysuccinamide, p-nitrophenyl, 2, 4, 6-trichlorophenyl, pentafluorophenyl) and then subsequent reaction of the activated amino acid with an unprotected or C-protected amino acid. The active esters of olefinic amino acids can be prepared, for example, by reacting a solid N-protected olefinic amino acid with an appropriate alcohol with help of the condensing agent (e.g., dicyclohexylcarbodiimide). These same procedures can also be used, for example, when one or both of the amino acids to be reacted are part of, and incorporated into, respectively, for example, one or two peptides.

Formation of C-terminally protected olefinic amino acids can easily be facilitated by reacting dry solid olefinic amino acid(s) with an appropriate alcohol (e.g., methyl, ethyl, benzyl) under, for example, anhydrous conditions. Formation of a peptide where olefinic amino acid is located in the C-terminal position can accomplished, for example, in the similar way. Solution methods of peptide preparation can be easily adapted to process scale. The starting materials and reagents used herein in preparing any compound herein and as above-and-below disclosed, unless otherwise indicated, for example, can be available from commercial sources such as Aldrich, Sigma or Bachem, or can be prepared by methods known to those skilled in the art following procedures set forth, for example, in references such as: Fieser and Fieser's Reagents for Org. Syn. Vol. 1-17, Organic Reactions Vol. 1-40, March's Advanced Organic Synthesis, Larock's Comprehensive Organic Transformations, Bodansky and Bodansky's The Practice of Peptide Synthesis, Greene's Protective Groups in Organic Synthesis, Wei, Q., et al., *Tetrahedron* 56: 2577-2582 (2000), Belokon, Y. N., et al., *Tetrahedron: Asymmetry* 9: 4249-4252 (1998), Belokon, Y., *Pure & App. Chem.* 64(12): 1917-1924 (1992), Ueki, H., et al., *J. Org. Chem.* 68: 7104-7107 (2003).

These schemes herein are illustrative of some methods by which compounds herein and their salts (which can be crystalline) can be synthesized, and various modifications to these schemes can be made and will be suggested to one skilled in the art having referred to this disclosure.

The starting materials and intermediates of the reactions of any embodiment herein, herein and as-above disclosed, unless otherwise indicated, may be isolated and purified if desired using conventional techniques, including, but not limited to filtration, distillation, crystallization, chromatogram, flash chromotography, HPLC, MPLC, Chromatotron®, ion exchange chromatography, crystallization with Mosher acids or Mosher esters, and the like. Such materials may be characterized using conventional means, including physical constructs and spectral data, for example proton NMR, carbon NMR, IR spectroscopy, polarimetry, atomic absorption, elemental analysis, UV spectroscopy, FTIR spectroscopy, and the like. In any embodiment here and as-above described, unless otherwise indicated, chromatography can be excluded in making any of the compounds or their salts.

Unless specified to the contrary, the reactions described herein can take place at, for example, from about 0.001 to about 100 atmospheres (atm), for example, about 0.001 atm, about 0.01 atm, about 0.1 atm, about 1 atm, about 2 atm, about 3 atm, about 4 atm, about 5 atm, about 10 atm, about 20 atm, about 50 atm, or about 100 atm.

Reactions in any embodiment herein, unless otherwise indicated, can be run, unless otherwise specified, for example, open to the atmosphere, or under an inert gas atmosphere such as, for example, nitrogen or argon.

Reactions in any embodiment herein, unless otherwise indicated, can be run, unless otherwise specified, for example, at temperatures from about −78° C. to about 150° C., for example from about −78° C., about −50° C., about −20° C., about 0° C., about 10° C., about 20° C., about 23° C., about 25° C., about 27° C., about 30° C., about 40° C., about 50° C., about 100° C., about 125° C., about 150° C., at about ambient temperature, or at about room temperature.

Reactions herein, unless otherwise indicated, can have a yield, unless otherwise explicitly stated, based on the theoretical yield, for example, ranging from about 1% to about 99%. The yield can be, for example, about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%.

Reactions herein, unless otherwise indicated, can be run, unless otherwise specified, for example, for a time ranging from about 0.1 to about 96 hours, e.g., for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, about 72 hours, or about 96 hours, Selective Uses of Crosslinked Peptidomimetic Macrocycles (Stitched and Stapled Peptides)

Crosslinked peptidomimetic macrocycles (stitched or stapled peptides), made with for example at least one of the crystalline compounds and their crystalline salts of Formula (I), including the crystalline compounds and their salts of Formulae (IIa), (IIb), (IIIa) and (IIIb), as well as the optionally crystalline compounds and their optionally crystalline salts of Formula (IV), can be used to treat or prevent diseases. For example, the crosslinked peptidomimetic macrocycles (stitched or stapled peptides) can be used to treat or prevent cancers. Selected examples of cancers include, for example, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Diseases which can be treated by stitched or stapled peptides can be found, for example, in International Application No. PCT/US2004/038403 ("the '403 application") and International Application Publication No. WO2008/121767 ("the '767 publication").

While inventive embodiments have been shown and described herein, such embodiments are provided by way of example only. Numerous variations, changes, and substitutions will now occur to those skilled in the art without departing from the inventive disclosure herein. The following Examples are illustrative and should not be construed as limiting.

EXAMPLES

Example 1: Preparation of crystalline N-Fmoc-(R)-α-methyl-α-aminodec-9-enoic acid

Example 1a: Preparation of (R)-2-[N—(N'-Boc-prolyl)amino]benzophenone

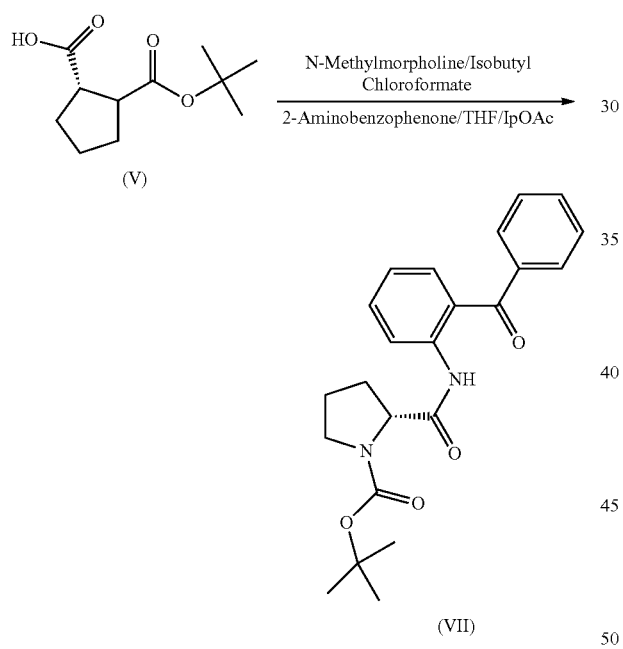

Tetrahydrofuran and 9.6 kg (1.0 equivs.) of Boc-D-proline (V) were added to a reactor and cooled to −5° C. 5.3 kg (1.15 equivs.) of N-methylmorpholine were charged followed by a slow addition of 6.1 kg (1.0 equivs.) of isobutyl chloroformate in tetrahydrofuran while maintaining the internal temperature at <5° C. The mixture was allowed to agitate at 20-25° C. for 45-60 minutes and then was analyzed by TLC for completion. A solution of 8.2 kg (0.9 equivs.) of 2-aminobenzophenone/tetrahydrofuran was charged and the mixture was allowed to agitate at 20-25° C. until the reaction is deemed complete. The mixture was concentrated to ½ volume and isopropyl acetate was charged. The organic product layer was then washed with a 5% sodium bicarbonate solution, water was charged, then the pH was adjusted to 2.0-2.5 with 25% sulfuric acid. The layers were split and the organic product layer was washed again with water. The organic product solution was then concentrated and crystallized from isopropyl acetate and washed with methyl tert-butyl ether. Product (VII) was isolated and dried under heat and vacuum. Yield: 12 kg, 66.7%.

Example 1b: Preparation of D-Proline-2-Aminobenzophenone amide

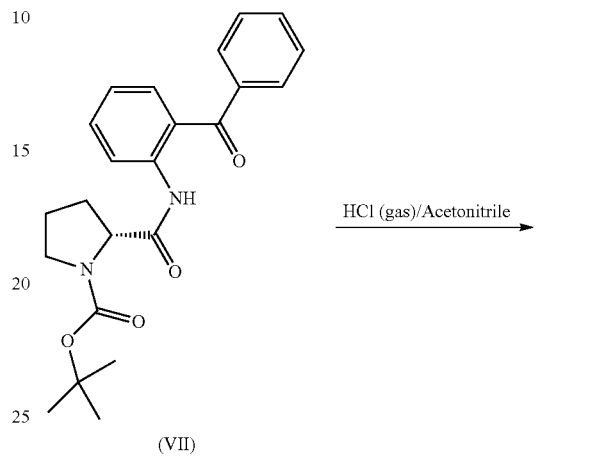

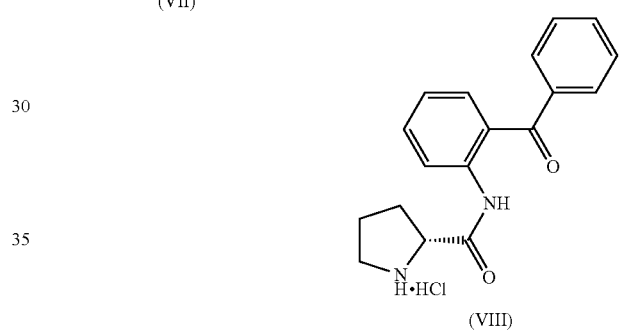

12.0 kg (1.0 equivs.) of Boc-D-proline-2-aminobenzophenone (VII) amide was dissolved into acetonitrile. 2.2 kg (2.0 equivs.) of hydrogen chloride gas was then charged/bubbled into the solution. The resulting mixture was then allowed to agitate at 20-25° C. until the reaction was complete. Methyl tert-butyl ether was added and the solid product was isolated out of the reaction solution and washed with additional methyl tert-butyl ether. The product (VIII) was dried under heat and vacuum. Yield: 9.1 kg, 100%.

Example 1c: Preparation of (R)-2-[N—(N'-benzyl-prolyl)amino]benzophenone (D-BPB)

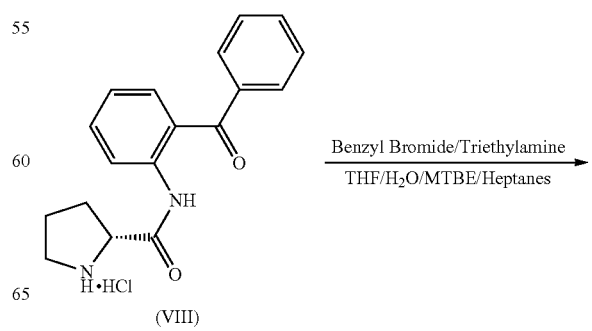

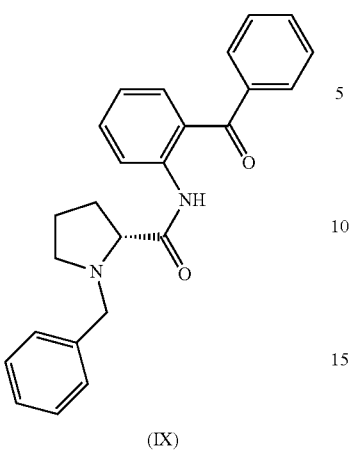

(IX)

9.1 kg (1.0 equivs.) of D-proline-2-aminobenzophenone amide.HCl (VIII) was dissolved into tetrahydrofuran and water. 8.1 kg (2.4 equivs.) of triethylamine was then charged, followed by a slow addition of 7.9 kg (1.4 equivs.) of benzyl bromide. The mixture was then allowed to agitate at 20-25° C. until the reaction was complete. Methyl tert-butyl ether and water were added and the resulting solution was pH adjusted to 2.0-2.5 with a 1N hydrochloric acid solution. The mixture was concentrated to remove all the tetrahydrofuran. The product slurry was then isolated and washed with methyl tert-butyl ether. The product (IX) was dried under heat and vacuum Yield: 10.5 kg, 82.7%.

Example 1d: Preparation of (R)-Ala-Ni-BPB

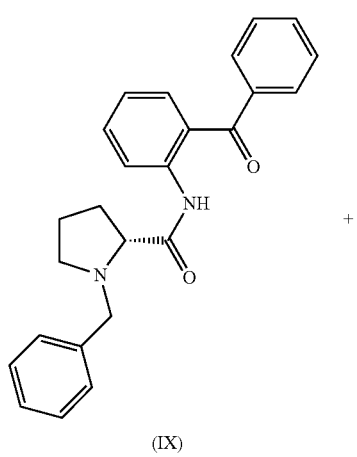

(IX)

+

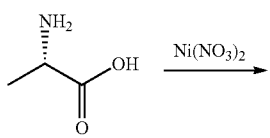

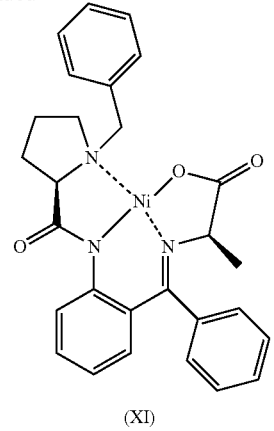

(XI)

10.5 kg (1.0 equivs.) of D-BPB (IX), 14.1 kg (1.78 equivs.) nickel (II) nitrate hexahydrate, 4.9 kg (2.0 equivs) of L-alanine, and methanol were charged to a reactor. The mixture was heated to 40° C. and a solution of 12.2 kg (8.0 equivs.) of potassium hydroxide/methanol was slowly added while maintaining the internal temperature of <50° C. The reaction mixture was then heated up to 60° C. and allowed to agitate at temperature until the reaction was complete. The mixture was then cooled to 20-25° C. and 8.2 kg (5.0 equivs.) of acetic acid was slowly charged while maintaining an internal temperature of <35° C. The reaction solution was concentrated to a solid. Tetrahydrofuran and isopropyl acetate were then added to dissolve the solid(s) and the organic product layer was washed 2× with water. The solution was then concentrated again and material was subsequently crystallized out of tetrahydrofuran and methyl tert-butyl ether. The product was isolated, rinsed with additional methyl tert-butyl ether and analyzed for purity. To improve purity the product (XI) was recrystallized out of isopropyl alcohol and then isolated, and dried under heat and vacuum. Yield: 6.8 kg, 48.6%.

Recrystallization Procedure

THF was added to the crude product (15 mL per 10 g of starting material (D-BPB)) and the resulting mixture was heated to 50° C. The mixture was maintained at 50° C. for 1 h, then methyl tertiary-butyl ether was added (50 mL per 10 g of starting material (D-BPB)). The mixture was maintained at 50° C. for additional 1 h after which it was cooled to 35° C. The mixture was filtered and the resulting solid was washed with methyl tertiary-butyl ether (20 mL per 10 g of starting material (D-BPB)) to obtain the crystalline product XI.

Alternate Recrystallization Procedure

Isopropyl acetate was added to the crude product (40 mL per 4 g of starting material (D-BPB)) and the resulting mixture was maintained at room temperature for 30 min. The mixture was then filtered to obtain the crystalline product XI.

Example 1e: Preparation of R8-Ni-BPB

Example 1f: Preparation of (R)-2-Amino-2-methyl-dec-9-enoic acid

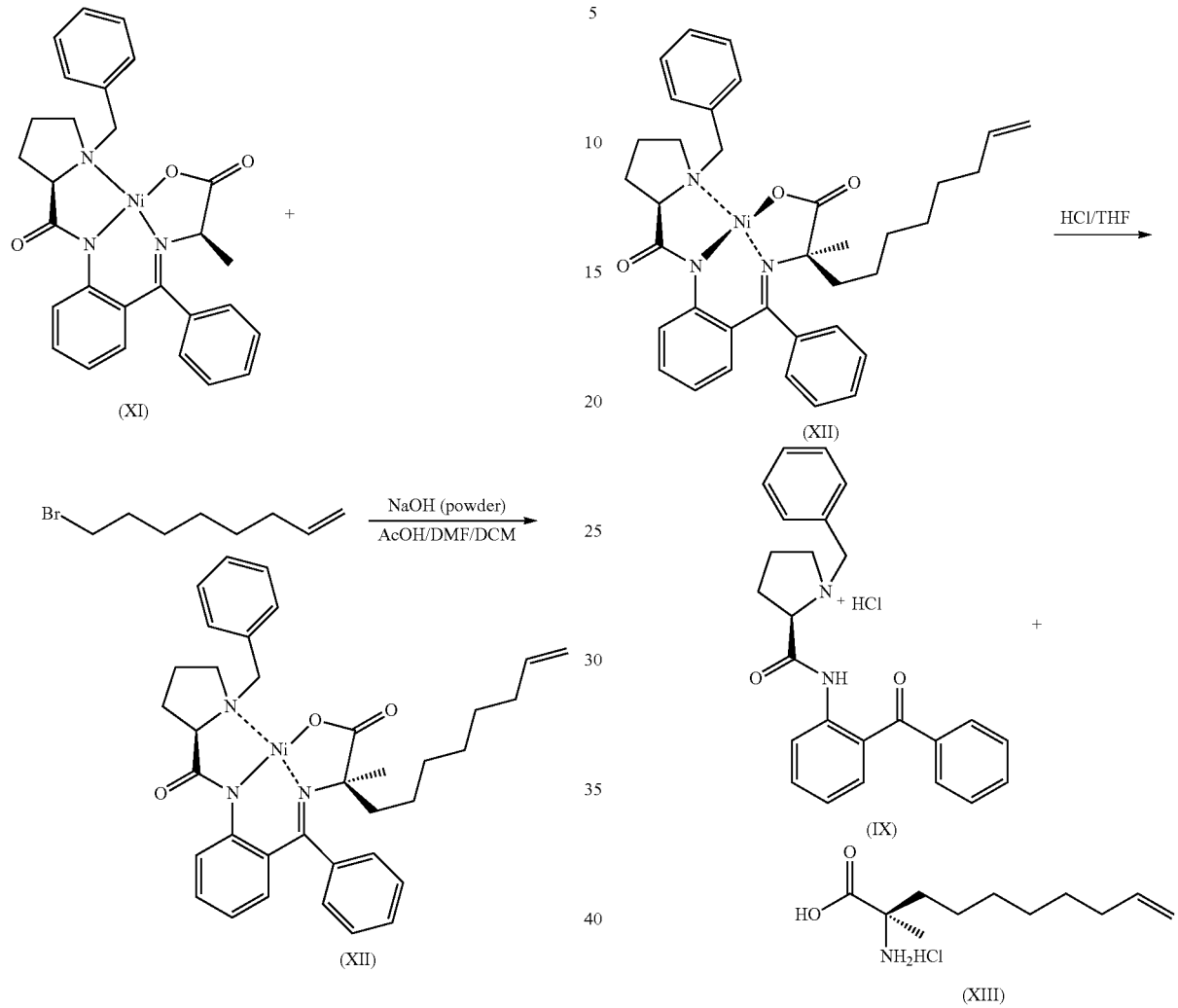

6.8 kg (1.0 equivs.) of (R)-Ala-Ni-BPB (XI) was charged to a reactor and dissolved up into dimethylformamide and cooled to 10° C. 1.4 kg (2.5 equivs.) of sodium hydroxide (powder) was then charged to the same reactor and the mixture was sparged with nitrogen and agitated until a solution formed at 10° C. 5.2 kg (2.0 equivs.) of 8-bromo-1-octene was charged to the reactor while maintaining an internal temperature of <20° C. The mixture was then allowed to agitate at 20-25° C. until the reaction was complete. Once the reaction was complete, the solution was cooled to 10° C. and 0.5 kg (0.6 equivs.) of acetic acid was charged maintaining the internal temperature <25° C. Water was then charged followed by methyl tert-butyl ether and the organic layer was washed. The organic layer was then washed 2 more times with water and then concentrated. The product oil was then co-stripped with methylene chloride and dissolved up in additional methylene chloride. The product (XII) solution was taken on into the next processing step.

The R8-Ni-BPB (XII)/DCM solution was charged to a 50-L chem-glass reactor and stripped to an oil. Tetrahydrofuran was then added and the mixture was agitated at 20-25° C. until a solution formed. 7.8 kg (5.0 equivs.) of 32% hydrochloric acid was charged slowly while maintaining an internal temperature of <30° C. The mixture was then allowed to agitate for 6-8 hours at ambient temperature. The mixture was then concentrated to remove tetrahydrofuran to yield a slurry. Additional water was added and the slurry was agitated at ambient temperature for 1-2 hours. The solid BPB salts were isolated by filtration and rinsed with additional water followed by methyl tert-butyl ether. The product filtrates were then re-charged to the reactor yielding a tri-phased solution. The lower-most layer was split from the upper two layers. The combined two organic layers were then washed 3× with water and concentrated to an oil. Acetonitrile was then added and the mixture was warmed to 70° C. for 30 minutes. The mixture was then cooled to 25-30° C. and the solid product was isolated. The solid filter-cake was washed with acetonitrile and methyl tert-butyl ether, then analyzed for purity. The product was then re-slurried out of additional acetonitrile and washed with acetonitrile and methyl tert-butyl ether. The material (XIII) was isolated and dried under heat and vacuum. Yield: 1.55 kg, 48%.

Recrystallization Procedure

Acetonitrile (23 mL per 10 g of starting material (oil of (R)-Ala-Ni-BPB (XI))) was added to the crude product and the resulting mixture was heated to 70° C. for 30 min after which it was cooled to 20° C. The mixture was filtered and the resulting solid was washed with acetonitrile (5 mL) and methyl tertiary-butyl ether (8.5 mL) to obtain the crystalline product XIII.

Alternate Recrystallization Procedure to Prepare XIII-I

Acetonitrile (30 mL per 10 g of starting material (oil of (R)-Ala-Ni-BPB (XI))) was added to the crude product and the resulting mixture was heated at 60° C. for 30 min followed by cooling to 30° C. The mixture was then filtered and washed with 5 mL acetonitrile to obtain the crystalline product XIII.

Alternate Recrystallization Procedure to Prepare XIII-II

Acetonitrile (23 mL per 10 g of starting material (oil of (R)-Ala-Ni-BPB (XI))) was added to the crude product and the resulting mixture was heated at 40° C. for 30 min followed by cooling to room temperature. The mixture was then filtered and washed twice with 5 mL acetonitrile to obtain the crystalline product XIII.

Example 1g: Preparation of Crystalline N-Fmoc-(R)-α-methyl-α-aminodec-9-enoic acid

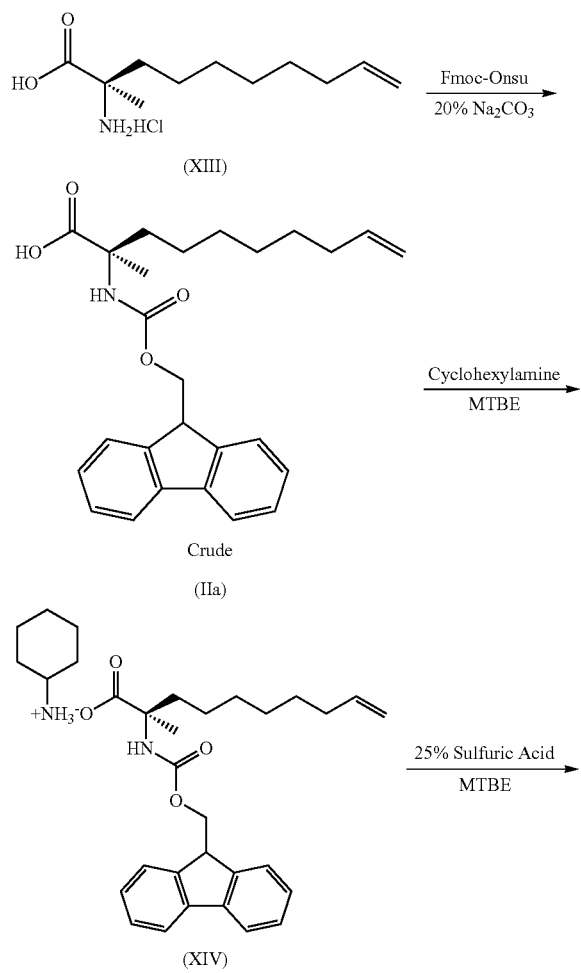

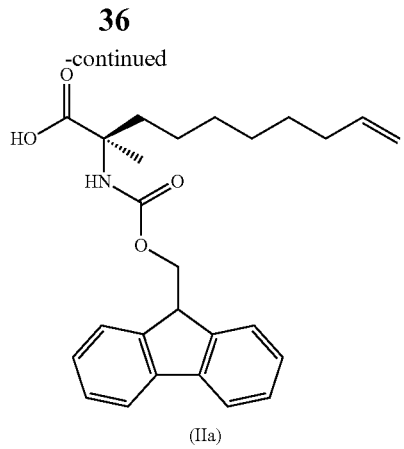

1.55 kg (1.0 equiv.) of 2-amino-2-methyl-dec-9-enoic acid.HCl (XIII) was suspended in water and polished filtered to remove trace amounts of D-BPB.HCl from the solution. Methyl tert-butyl ether was added and the aqueous product layer was extracted once with methyl tert-butyl ether. The aqueous product layer was re-charged and tetrahydrofuran was added. A 20% aqueous sodium carbonate solution (2.75 equiv.) was charged to the mixture followed by Fmoc-OSu (0.89 equiv.). The mixture was allowed to react at 20-25° C. while maintaining the pH between 8.5-9.0 with additional amounts of the 20% sodium carbonate solution until the reaction was complete. The mixture was pH adjusted down to pH 2.0-2.5 with conc. hydrochloric acid. Tetrahydrofuran was distilled off and methyl tert-butyl ether was charged. The layers were separated and the organic layer was washed 3 more times with additional water. The organic layer was then concentrated under vacuum and co-stripped with methyl tert-butyl ether. The resulting crude oil was re-dissolved in methyl tert-butyl ether and cyclohexylamine (1.10 equiv.) was added slowly to obtain a pH range of 8.5-9.0. The slurry was agitated at ambient temperature (20-25° C.) for 3 hours and the solid product salt (XIV) was isolated by filtration. The solids were rinsed twice with additional methyl tert-butyl ether and the solid wetcake was recharged to a clean reactor. The wetcake was recrystallized from tetrahydrofuran and methyl tert-butyl ether to improve the purity. The solid salt was suspended in methyl tert-butyl ether and water and the pH adjusted to 2.0-2.5 with 25% sulfuric acid. The organic product layer was washed with water until all of the cyclohexylamine was removed. The organic product layer was concentrated and co-stripped with hexanes to a loose oil. The product (IIa) was then crystallized out of chloroform and hexanes and dried at <0° C. under a 1.0 cfm nitrogen sweep. Yield: 1.12 kg, 41.5%

Recrystallization Procedure

Methyl tertiary-butyl ether (800 mL per 36 g of starting material XIII) was added to the crude product and the pH of the resulting mixture was adjusted to 8-9 using CHA at 20° C. The mixture was mixed at 20° C. and after 1 h crystals started forming. Additional methyl tertiary-butyl ether was added (200 mL) and the resulting slurry was mixed for 18 h. The mixture was filtered and the resulting solid was washed with twice methyl tertiary-butyl ether (200 mL and 8.5 mL) to obtain the crystalline product XIII. The product was analyzed for chiral purity, and if the results were less than 95% Fmoc-R8 vs. Fmoc-S8 then crystallization was performed to upgrade the chiral purity by dissolving dry FmocR/S (50 g) in THF (50 mL). Once FmocR/S was dissolved, methyl tertiary-butyl ether was added (900 mL) and the mixture was mixed at 20° C. for 18 h. The mixture was then filtered and washed twice with methyl tertiary-butyl ether (100 mL each). The chiral purity of the resulting crystalline product XIV was about 97.8%

Alternate Recrystallization Procedure for XIV-I

Methyl tertiary-butyl ether (1500 mL per 47 g of starting material XIII) was added to the crude product and the pH of the resulting mixture was adjusted to 8-9 using CHA at 20° C. The mixture was mixed at this temperature for 3 h after which it was filtered and the resulting solid was washed with methyl tertiary-butyl ether (250 mL).

Alternate Recrystallization Procedure for XIV-II

Methyl tertiary-butyl ether (400 mL per 20 g of starting material XIII) was added to the crude product and the pH of the resulting mixture was adjusted to 8-9 using CHA at 20° C. Additional 200 mL methyl tertiary-butyl ether was added and the mixture was mixed at this temperature for 2 h after which it was filtered and the resulting solid was washed with methyl tertiary-butyl ether (10 mL).

Alternate Recrystallization Procedure for XIV-III

Methyl tertiary-butyl ether (50 mL per 4 g of starting material XIII) was added to the crude product and the pH of the resulting mixture was adjusted to 8-9 using CHA at 20° C. The mixture was mixed at this temperature for 45 min after which it was filtered and the resulting solid was washed with methyl tertiary-butyl ether (10 mL).

Recrystallization Procedure for IIa

Chloroform (70 mL) was added to the crude product (25 g) and the resulting mixture was cooled to 0° C. Hexanes (210 mL) were then slowly added so as to maintain the temperature at 0° C. The mixture was further maintained at this temperature for 1 h after which it was filtered cooled and the resulting solid was dried under vacuum at 0° C.

Alternate Recrystallization Procedure for IIa-I

Chloroform (2200 m L) was added to the crude product (1100 g). Hexanes (6600 L) were then added slowly and the resulting mixture was cooled to less than 0° C. The mixture was further mixed at temperature below 0° C. for 1 h after which it was filtered at less than 0° C. and the resulting solid was dried under vacuum at temperature below 0° C.

Example 2: Preparation of crystalline N-Fmoc-(S)-α-methyl-α-aminohept-6-enoic acid Example 2a: Preparation of (S)-2-[N—(N'-Boc-prolyl)amino]benzophenone

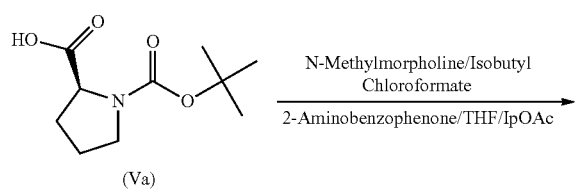

(Va)

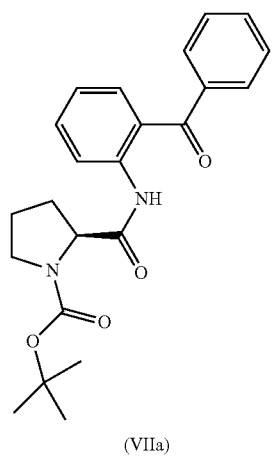

(VIIa)

Tetrahydrofuran and 7.5 kg (1.0 equivs.) of Boc-L-proline (Va) were added to a reactor and the resulting solution was cooled to −5° C. 4.2 kg (1.05 equivs.) of N-methylmorpholine were charged, followed by slow addition of 5.3 kg (1.0 equivs.) of isobutyl chloroformate in tetrahydrofuran while maintaining an internal temperature of <5° C. The mixture was allowed to agitate at 20-25° C. for 45-60 minutes and then was analyzed by TLC for completion. A solution of 6.2 kg (0.9 equivs.) of 2-aminobenzophenone/tetrahydrofuran was charged and the mixture was allowed to agitate at 20-25° C. until the reaction was shown to be complete by TLC. The mixture was concentrated to ½ volume and isopropyl acetate was charged. The organic product layer was then washed with a 5% sodium bicarbonate solution, water was charged, and then pH adjusted to 2.0-2.5 with 25% sulfuric acid. Layers were split and the organic product layer was washed again with water. The organic product solution/layer was then concentrated and crystallized from isopropyl acetate and washed with methyl tert-butyl ether. Product (VIIa) was then isolated and dried under heat and vacuum. Yield: 9.3 kg, 75%.

Example 2b: Preparation of L-Proline-2-Aminobenzophenone amide

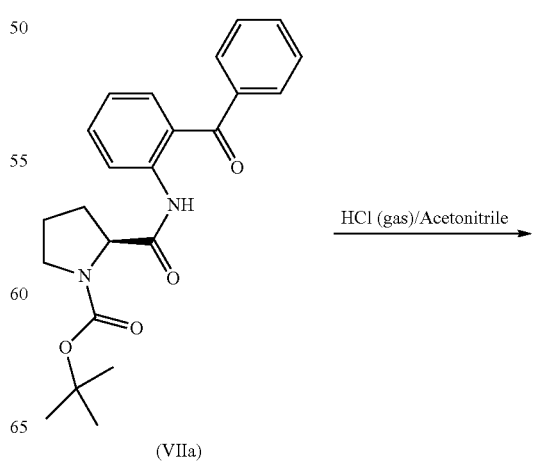

(VIIa)

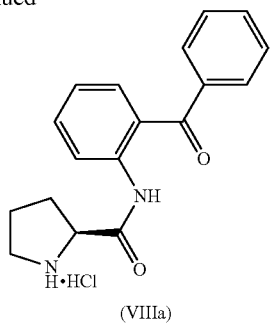

(VIIIa)

9.4 kg (1.0 equivs.) of Boc-L-proline-2-aminobenzophenone amide (VIIa) was dissolved into acetonitrile. 1.7 kg (2.0 equivs.) of hydrogen chloride gas were then charged/bubbled into the solution. This mixture was allowed to agitate at 20-25° C. until the reaction was demonstrated to be complete by TLC. Methyl tert-butyl ether was added and a solid product was isolated out of the reaction solution and washed with additional methyl tert-butyl ether. The product (VIIIa) was dried under heat and vacuum. Yield: 7.0 kg, 100%.

Example 2c: Preparation of (S)-2-[N—(N'-benzyl-prolyl)amino]benzophenone (L-BPB)

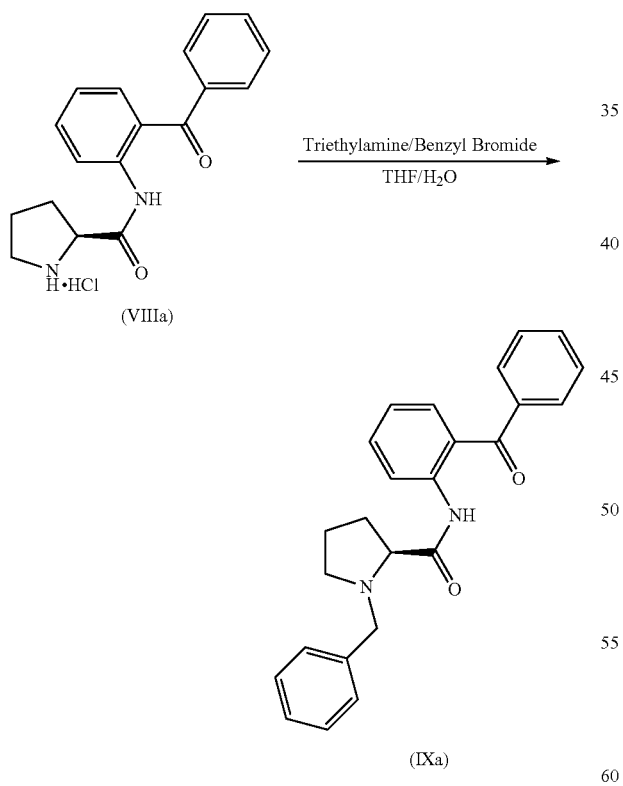

7.1 kg (1.0 equivs.) of L-proline-2-aminobenzophenone amide.HCl (VIIIa) was dissolved into tetrahydrofuran and water. 5.8 kg (2.4 equivs.) of triethylamine were then charged followed by a slow addition of 5.9 kg (1.4 equivs.) of benzyl bromide. The mixture was then allowed to agitate at 20-25° C. until the reaction was complete. Methyl tert-butyl ether and water were added and the solution pH was adjusted to 2.0-2.5 with a 1N hydrochloric acid solution. The mixture was concentrated to remove all the tetrahydrofuran. The product slurry was then isolated and washed with methyl tert-butyl ether. The product (IXa) was dried under heat and vacuum. Yield 7.7 kg, 84.0%.

Example 2d: Preparation of (S)-Ala-Ni-BPB

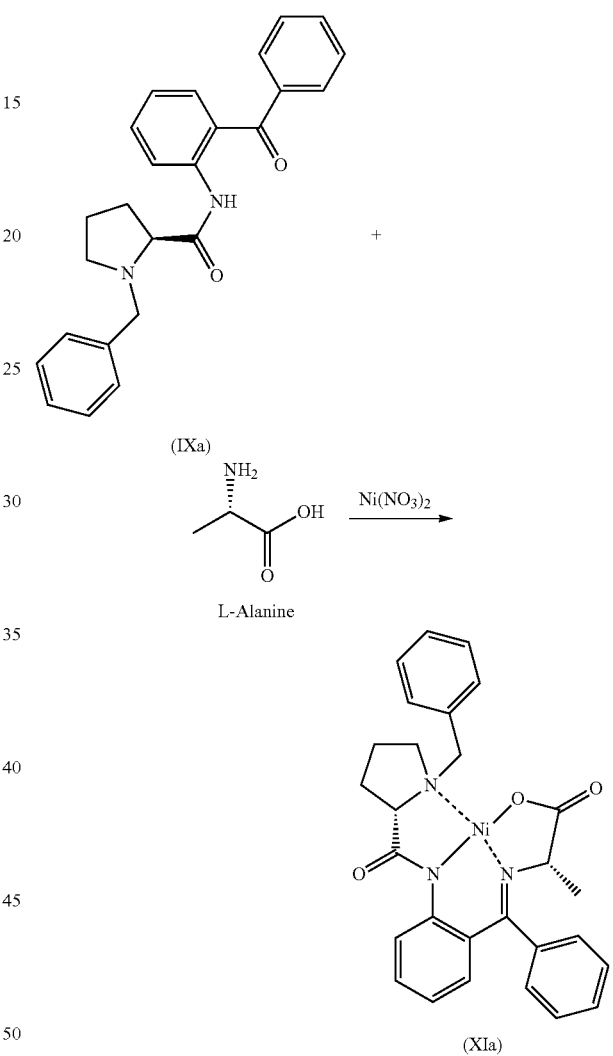

7.9 kg (1.0 equivs.) of L-BPB (IXa), 12.1 kg (1.78 equivs.) nickel (II) nitrate hexahydrate, 3.7 kg (2.0 equivs) of L-alanine, and methanol were charged to a reactor. The mixture was heated to 40° C. and a solution of 8.2 kg (8.0 equivs.) of potassium hydroxide/methanol was slowly added while maintaining the internal temperature at <50° C. The reaction mixture was then heated up to 60° C. and allowed to agitate at temperature until the reaction was complete. The mixture was subsequently cooled to 20-25° C. and 8.9 kg (5.0 equivs.) of acetic acid was slowly charged while maintaining the internal temperature at <35° C. The reaction solution was then concentrated to a solid. Tetrahydrofuran and isopropyl acetate were added to dissolve the solids and the organic product layer was washed twice with water. The solution was concentrated again and material crystallized out of tetrahydrofuran and methyl tert-butyl ether. The product was isolated, rinsed with additional methyl tert-butyl ether and analyzed for purity. To improve purity the product (XIa) was recrystallized out of isopropyl alcohol and then isolated, and dried under heat and vacuum. Yield: 6.0 kg, 56.0%.

Recrystallization Procedure for XIa

Methyl tertiary-butyl ether (550 mL per 50 g of starting material L-BPB) was added to the crude product (S)-Ala-Ni-BPB and the slurry was then heated to 50° C. before cooling it to 20° C. The mixture was mixed at 20° C. for 16 h. The mixture was filtered and the resulting solid was washed with methyl tertiary-butyl ether (100 mL) to obtain the crystalline product XIa.

Alternate Recrystallization Procedure for XIa

Methyl tertiary-butyl ether (600 mL per 50 g of starting material L-BPB) was added to the crude product (S)-Ala-Ni-BPB and the slurry was then heated to 50-60° C. and maintained at this temperature for 1 h. The mixture was then filtered at 35° C. and washed with methyl tertiary-butyl ether (100 mL) to obtain the crystalline product XIa.

Alternate Recrystallization Procedure for XIa

Methyl tertiary-butyl ether (500 mL per 50 g of starting material L-BPB) was added to the crude product (S)-Ala-Ni-BPB and the slurry was then heated to 45-50° C. and maintained at this temperature for 1 h. The mixture was then filtered at 35° C. and washed with methyl tertiary-butyl ether (100 mL) to obtain the crystalline product XIa.

Alternate Recrystallization Procedure-III

Methyl tertiary-butyl ether (2000 mL per 280 g of starting material L-BPB) was added to the crude product (S)-Ala-Ni-BPB and the slurry was then heated to 45-50° C. and maintained at this temperature for 30 min. The mixture was then cooled to 20° C. and mixed at this temperature for 8 h. The resulting solid was then filtered and washed with methyl tertiary-butyl ether (100 mL).

(S)-Ala-Ni-BPB (300 g) was recrystallized by dissolving in THF (450 mL). The mixture was heated to 50° C. for 1 h followed by the addition of methyl tertiary-butyl ether (1500 mL) at 50° C. The resulting mixture was mixed at this temperature for additional 1 h. The slurry was then cooled to 20° C. and mixed at 20° C. for 1 h. The resulting solid was then filtered and washed with methyl tertiary-butyl ether (300 mL) to obtain the crystalline product XIa.

Example 2e: Preparation of S5-Ni-BPB

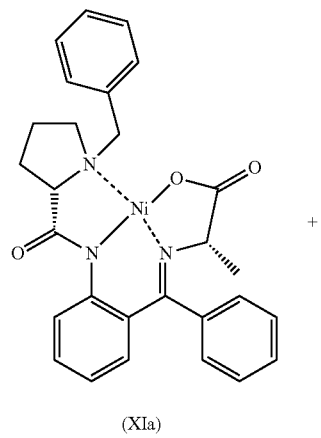

(XIa)

+

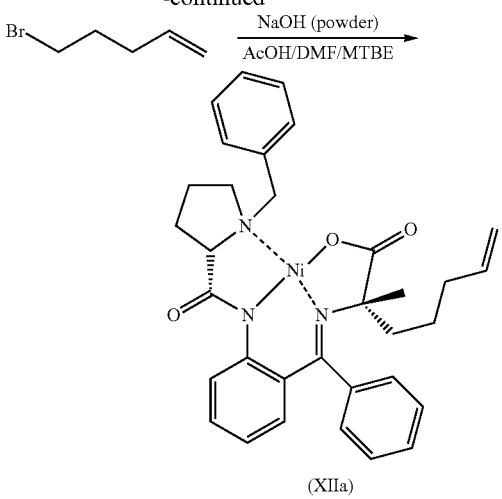

(XIIa)

5.8 kg (1.0 equivs.) of (S)-Ala-Ni-BPB (XIa) was charged to a reactor and dissolved up into dimethylformamide and cooled to 10° C. 1.2 kg (2.5 equivs.) of sodium hydroxide (powder) was then charged to the same reactor and the mixture was sparged with nitrogen and agitated until a solution formed at 10° C. 3.3 kg (2.0 equivs.) of 5-bromo-1-pentene was then charged to the reactor maintaining the internal temperature of <20° C. The mixture was then allowed to agitate at 20-25° C. until the reaction was complete. Once the reaction was complete, the solution was cooled to 10° C. and 0.4 kg (1.5 equivs.) of acetic acid was charged maintaining an internal temperature of <25° C. Water was then charged, followed by methyl tert-butyl ether, and the organic layer was washed. The organic layer was then washed 2 more times with water and then concentrated. The product (XIIa) was crystallized out of isopropyl acetate, isolated and dried under heat and vacuum. Yield: 2.2 kg, 32.4%.

Recrystallization Procedure

Isopropyl acetate (200 mL per 12.5 g of starting material XIa) was added to the crude product S5-Ni-BPB and the mixture was mixed at 20° C. for 30 min then hexanes (500 mL) were added. The mixture was further mixed for 30 min following which it was filtered to obtain the crystalline product XIIa.

Alternate Recrystallization Procedure-I

Isopropyl acetate (80 mL per 39 g of starting material XIa) was added to the crude product S5-Ni-BPB and the mixture was mixed at 20° C. for 2 h. The mixture was filtered and washed with isopropyl acetate (35 mL). The filtrate and the washed were combined and heptanes (170 mL) were added. The resulting slurry was mixed for 1 h, then filtered and washed with heptanes (360 mL) to obtain the crystalline product XIIa.

Alternate Recrystallization Procedure-II

Isopropyl acetate (1000 mL per 205 g of starting material XIa) was added to the crude product S5-Ni-BPB and the mixture was dissolved at 70-80° C. The solution was cooled to 20° C. and the mixture was mixed at this temperature for 1 h during which no crystallization was observed. The mixture was filtered over celite and the solvent was removed under vacuum at 40° C. Methyl tertiary-butyl ether (1000 mL) was added and the mixture was heated to 60° C. then cooled to 20° C. and mixed for 24 h. The solid was filtered and washed with methyl tertiary-butyl ether (300 mL) and to obtain the crystalline product XIIa.

Alternate Recrystallization Procedure-III

Ethyl acetate (100 mL per 12.5 g of starting material XIa) was added to the crude product S5-Ni-BPB and the mixture was mixed at 20° C. for 30 min. hexanes (500 mL) were added and the resulting slurry was mixed for further 30 min after which it was filtered to obtain the crystalline product XIIa.

Alternate Recrystallization Procedure-IV

Methyl tertiary-butyl ether (100 mL per 12.5 g of starting material XIa) was added to the crude product S5-Ni-BPB and the mixture was heated to 45-50° C. Heptanes (400 mL) were added 45-50° C. The resulting slurry was cooled to 20° C. and filtered to obtain the crystalline product XIIa.

Example 2f: Preparation of (S)-2-Amino-2-methyl-hept-6-enoic acid

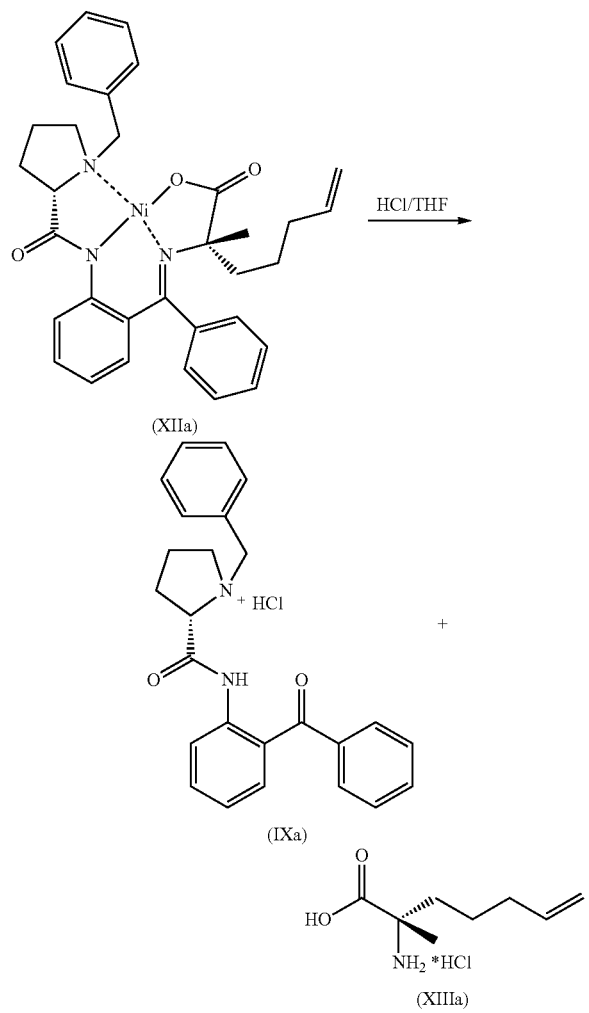

2.2 kg (1.0 equivs.) of S5-Ni-BPB (XIIa) was charged to a 15-L chem-glass reactor. Tetrahydrofuran was added and the mixture agitated at 20-25° C. until a solution formed. 1.8 kg (4.5 equivs.) of 32% hydrochloric acid was charged slowly while maintaining an internal temperature of <30° C. The mixture was then allowed to agitate for 6-8 hours at ambient temperature. The mixture was concentrated to remove tetrahydrofuran to yield a slurry. Additional water was added and the slurry was agitated at ambient temperature for 1-2 hours. The solid BPB salts were isolated by filtration and rinsed with additional water followed by methyl tert-butyl ether. The product filtrates were then re-charged to the reactor yielding a tri-phased solution. The lower-most layer was split from the upper two layers. The combined two organic layers were then washed 3× with water and concentrated to an oil. Acetonitrile was added and the mixture was warmed to 70° C. for 30 minutes. The mixture was then cooled to 25-30° C. and the solid product was isolated. The solid filter-cake was washed with acetonitrile and methyl tert-butyl ether, then analyzed for chemical purity. The product was then re-slurried out of additional acetonitrile and washed with acetonitrile and methyl tert-butyl ether. The material (XIIIa) was isolated and dried under heat and vacuum. Yield: 0.585 kg, 80.0%

Recrystallization Procedure for XIIIa

Acetonitrile (100 mL per 20 g of starting material S5-Ni-BPB (XIIa)) was added to the crude product and the mixture was mixed at 20° C. for 1 h. The mixture was then filtered and washed with acetonitrile (40 mL) to obtain the crystalline product XIIIa.

Alternate Recrystallization Procedure for XIIIa-I

Acetonitrile (500 mL per 185 g of starting material XIIa) was added to the crude product S5-Ni-BPB and the slurry was dissolved at 45-50° C. The solvent was removed under vacuum at 45-50° C., 500 mL acetonitrile was added and the resulting mixture was heated to 45-50° C. The mixture was then cooled to 35° C., filtered and washed with acetonitrile (50 mL) to obtain the crystalline product XIIIa.

Alternate Recrystallization Procedure for XIIIa-II

Acetonitrile (270 mL per 35 g of starting material XIIa) was added and the slurry was heated to 45-50° C. The mixture was then cooled to 20° C. and mixed at this temperature for 2 h. The mixture was then filtered and washed with acetonitrile (50 mL) and methyl tertiary-butyl ether (50 mL) to obtain the crystalline product XIIIa.

Alternate Recrystallization Procedure for XIIIa-III

Isopropyl acetate (60 mL per 15 g of XIIIa) was added and the mixture was heated to 70° C. Acetonitrile (180 mL) was added and the resulting mixture was cooled to 20° C. The mixture was filtered and the resulting solid was washed with acetonitrile (50 mL) to obtain the crystalline product XIIIa.

Example 2g: Preparation of N-Fmoc-(S)-α-methyl-α-aminohept-6-enoic acid

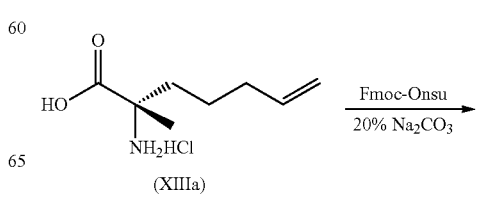

-continued

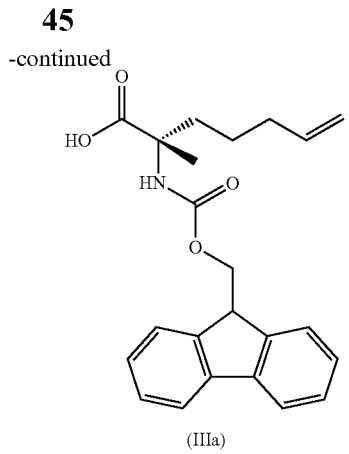

(IIIa)

0.585 kg (1.0 equiv.) of 2-amino-2-methyl-hept-6-enoic acid.HCl (XIIIa) was suspended in water and polished filtered to remove trace amounts of L-BPB.HCl from the solution. Methyl tert-butyl ether was added and the aqueous product layer extracted once with methyl tert-butyl ether. The aqueous product layer was re-charged and tetrahydrofuran was added. An aqueous 20% sodium carbonate solution (2.75 equiv.) was charged to the mixture, followed by Fmoc-Onsu (0.95 equiv.). The mixture was allowed to react at 20-25° C., while maintaining the pH between 8.5-9.0 with additional amounts of the 20% sodium carbonate solution until the reaction was complete. The mixture was pH adjusted down to pH 2.0-2.5 with conc. hydrochloric acid. Tetrahydrofuran was distilled off and methyl tert-butyl ether is charged. The layers were separated and the organic layer was washed 3 more times with additional water. The organic layer was then concentrated under vacuum and co-stripped with methyl tert-butyl ether. The organic product layer was concentrated and co-stripped with hexanes to a loose oil. The product (IIIa) was then crystallized out of chloroform and hexanes and dried at <0° C. under a 1.0 cfm nitrogen sweep. Yield: 0.831 kg, 76.0%.

Recrystallization Procedure for IIIa

Chloroform (30 mL per 9 g of starting material XIIIa) was added to the crude product. Hexanes (100 mL) were added and the mixture was cooled to 0° C. The resulting solid was filtered at 0° C. and washed with cold hexanes to obtain the crystalline product IIIa.

Recrystallization Procedure for Cyclohexylamine Salt of IIIa

Acetonitrile (300 mL per 19.04 g of starting material XIIIa) was added to the crude product and the pH was adjusted to 8-9 using cyclohexylamine at 20° C. The resulting mixture was mixed at 20° C. for 2 h and then filtered and washed with acetonitrile (50 mL) to obtain the crystalline cyclohexylamine salt of IIIa.

Alternate Recrystallization Procedure for Cyclohexylamine Salt of IIIa-I

Methyl tertiary-butyl ether (200 mL per 5 g of starting material XIIIa) was added to the crude product and the pH was adjusted to 8-9 using cyclohexylamine at 20° C. The resulting mixture was mixed at 20° C. for 1 h and then filtered and washed with methyl tertiary-butyl ether (50 mL) to obtain the crystalline cyclohexylamine salt of IIIa.

What is claimed is:

1. A crystalline composition comprising a crystalline compound of Formula (I):

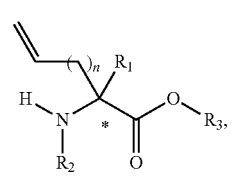

Formula (I)

wherein:
R$_1$ is C$_1$-C$_3$ alkyl, C$_1$-C$_3$ deuteroalkyl, or C$_1$-C$_3$ haloalkyl;
\* is a stereocenter;
n is an integer from 3 to 11;
R$_2$ is 9-Fluorenylmethoxycarbonyl (Fmoc); and
R$_3$ is —H;
and wherein the crystalline composition further comprises hexane and chloroform.

2. The crystalline composition of claim 1, wherein R$_1$ is C$_1$-C$_3$ alkyl.

3. The crystalline composition claim of 1, wherein R$_1$ is methyl.

4. The crystalline composition of claim 1, wherein n is selected from the group consisting of: 3 and 6.

5. The crystalline composition of claim 1, wherein the stereocenter \* is (S).

6. The crystalline composition of claim 1, wherein the stereocenter \* is (R).

7. The crystalline composition of claim 1, wherein the crystalline compound has a chemical purity ranging from about 90% to 100%.

8. The crystalline composition of claim 1, wherein the crystalline compound has an optical purity ranging from about 90% to 100%.

9. The crystalline composition of claim 1, wherein the crystalline compound has an optical purity ranging from about 95% to 100%.

10. The crystalline composition of claim 1, wherein the crystalline compound has an enantiomeric excess ranging from about 90% to 100%.

11. The crystalline composition of claim 1, wherein the crystalline compound has an enantiomeric excess ranging from about 95% to 100%.

12. The crystalline composition of claim 1, wherein the crystalline compound has a Formula (IIa):

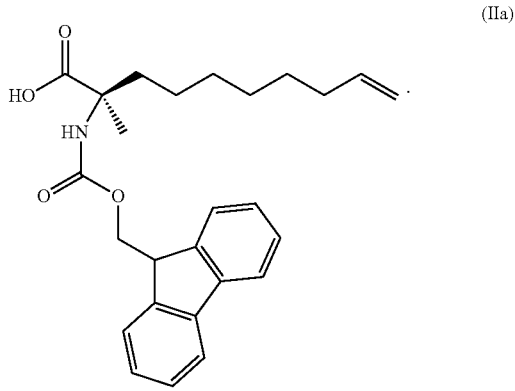 [SMILES: C=CCCCCCC[C@@](C)(NC(=O)OCC1c2ccccc2-c2ccccc21)C(=O)O]

(IIa)

13. The crystalline composition of claim 1, wherein the crystalline compound has a Formula (IIb):

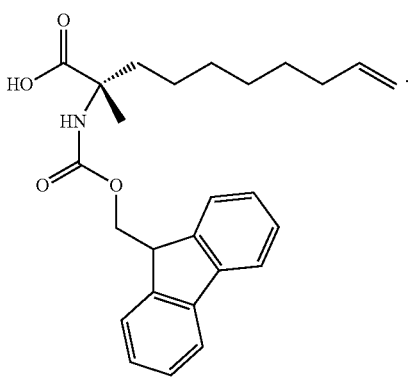

14. The crystalline composition of claim 1, wherein the crystalline compound has a Formula (IIIa):

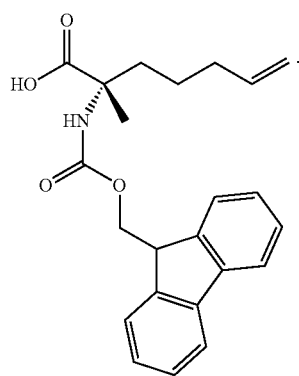

15. The crystalline composition of claim 1, wherein the crystalline compound has a Formula (IIIb):

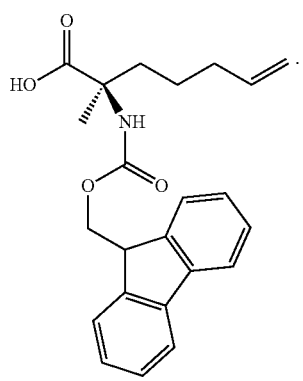

16. The crystalline composition of claim 12, wherein the crystalline compound has an enantiomeric excess ranging from about 95% to 100%.

17. The crystalline composition of claim 13, wherein the crystalline compound has an enantiomeric excess ranging from about 95% to 100%.

18. The crystalline composition of claim 14, wherein the crystalline compound has an enantiomeric excess ranging from about 95% to 100%.

19. The crystalline composition of claim 15, wherein the compound or its crystalline salt has an enantiomeric excess ranging from about 95% to 100%.

20. The crystalline composition of claim 1, wherein n is 3.

21. A crystalline compound of Formula (I):

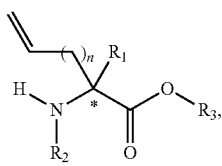

Formula (I)

wherein:
$R_1$ is $C_1$-$C_3$ alkyl, $C_1$-$C_3$ deuteroalkyl, or $C_1$-$C_3$ haloalkyl;

* is a stereocenter;

n is an integer from 3 to 11;

$R_2$ is 9-Fluorenylmethoxycarbonyl (Fmoc); and $R_3$ is —H;

wherein the crystalline compound is obtained by crystallization of a compound of Formula (I) with a solvent comprising hexane and chloroform.

22. A method of making a peptide, the method comprising reacting the crystalline composition of claim 1 with an amino acid building block in presence of a coupling agent, thereby forming a peptide bond.

23. The method of claim 1, wherein the peptide comprises an α-helix.

24. The method of claim 1, further comprising crosslinking a pair of terminal alkene side chains of at least two amino acids of the peptide.

25. The method of claim 24, wherein the crosslinking comprises a metal-catalyzed olefin metathesis reaction.

* * * * *